(12) United States Patent
Van Bergen et al.

(10) Patent No.: US 12,220,459 B2
(45) Date of Patent: Feb. 11, 2025

(54) IMMUNE-STIMULATORY COMPOSITIONS AND USE THEREOF

(71) Applicant: Nykode Therapeutics ASA, Oslo (NO)

(72) Inventors: Jeroen Van Bergen, Leiden (NL); Gerben Carolus Martinus Zondag, Leiden (NL)

(73) Assignee: Nykode Therapeutics ASA, Oslo (NO)

( * ) Notice: Subject to any disclaimer, the term of this patent is extended or adjusted under 35 U.S.C. 154(b) by 201 days.

(21) Appl. No.: 17/600,164

(22) PCT Filed: Apr. 2, 2020

(86) PCT No.: PCT/NL2020/050225
§ 371 (c)(1),
(2) Date: Sep. 30, 2021

(87) PCT Pub. No.: WO2020/204714
PCT Pub. Date: Oct. 8, 2020

(65) Prior Publication Data
US 2022/0211843 A1    Jul. 7, 2022

(30) Foreign Application Priority Data
Apr. 2, 2019   (EP) .................................. 19166877

(51) Int. Cl.
*A61K 39/39*      (2006.01)
*A61K 39/00*      (2006.01)

(52) U.S. Cl.
CPC .... *A61K 39/39* (2013.01); *A61K 2039/55516* (2013.01); *A61K 2039/55527* (2013.01)

(58) Field of Classification Search
CPC ........... A61K 2039/55511; A61K 2039/55516; A61K 2039/55527; A61K 2039/55522; A61K 2039/55505; C07K 2319/50; C12N 9/641
See application file for complete search history.

(56) References Cited

U.S. PATENT DOCUMENTS

| 6,379,950 B1 | 4/2002 | Alnemri |
| 6,916,917 B1 | 7/2005 | Baltimore et al. |
| 7,196,182 B2 * | 3/2007 | Reed .................. C07K 14/4702 435/6.16 |
| 2014/0037685 A1 | 2/2014 | Brojatsch et al. |
| 2014/0255360 A1 | 9/2014 | Spencer et al. |
| 2018/0311343 A1 | 11/2018 | Huang et al. |

FOREIGN PATENT DOCUMENTS

| JP | 2002500049 A | 1/2002 |
| JP | 2003528154 A | 9/2003 |
| JP | 2003528156 A | 9/2003 |
| WO | WO01/72336 A1 | 10/2001 |
| WO | WO2018/049014 A1 | 3/2018 |
| WO | WO2018/106753 A1 | 6/2018 |

OTHER PUBLICATIONS

Jia et al.; Specific tumoricidal activity of a secreted proapoptotic protein consisting of HER2 anitbody and constitutively active caspase-3; Cancer Research; 63; pp. 3257-3262; Jun. 2003.
Lee et al.; Purification of catalytically active caspase-12 and its biochemical characterization; Archives of Biochemistry and Biophysics; 502(1); pp. 68-73; Oct. 2010.
Park et al.; Expression and characterization of constitutively active human caspase-14; Biochemical and Biophysical research Communications; 347(4); pp. 941-948; Sep. 2006.
Sasaki et al.; Apoptosis-mediated enhancement of DNA-raised immune responses by mutant caspases; Nature biotechnology; 19(6); pp. 543-547; Jun. 2001.
Gui et al.; Expression of recombinant human caspase-8 genes and their effects on growth of HeLa cells; Journal of cellular and Molecular Immunology; (English Abstract); 18(2); 117-120; 2002 (the year of publication is sufficiently earlier than the effective U.S. filing date and any foreign priority date so that the particular month of publication is not in issue).

* cited by examiner

*Primary Examiner* — Bao Q Li
(74) *Attorney, Agent, or Firm* — Shay Glenn LLP

(57) ABSTRACT

The invention relates to a constitutively active pro-inflammatory caspase, comprising shuffled p10 and p20 domains, for use in a method of stimulating an immune response in an individual. The invention further relates to an immune-stimulating composition, comprising said constitutively active pro-inflammatory caspase, comprising shuffled p10 and p20 domains and a pharmacologically acceptable excipient, and its use in a method of treating an individual.

22 Claims, 12 Drawing Sheets

Figure 1:
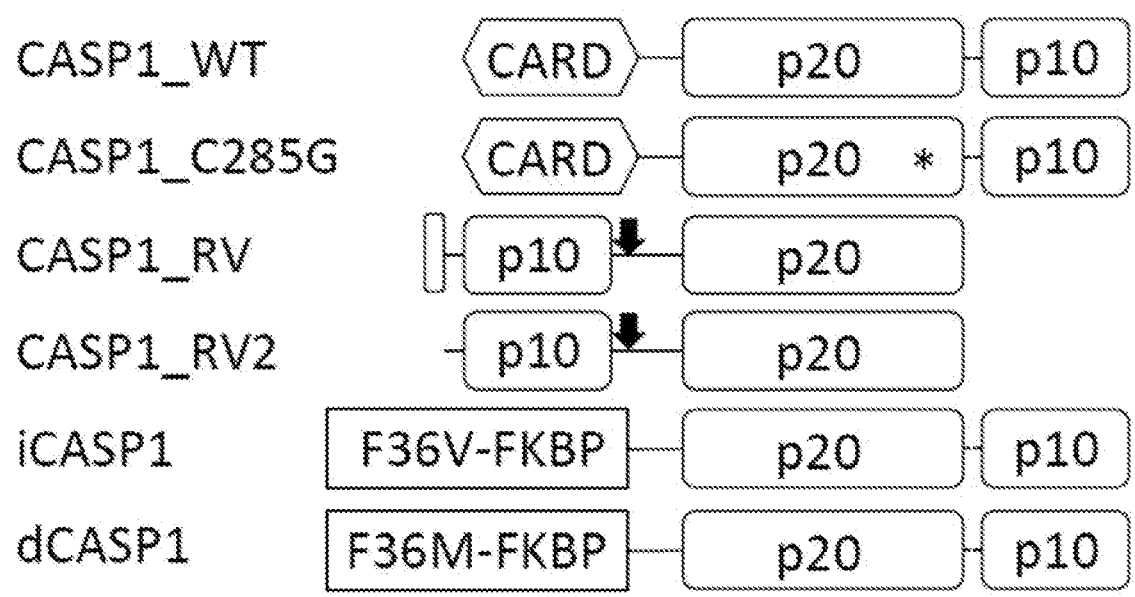

Specification includes a Sequence Listing.

A

B

C

A

B

A

B

A

SEQUENCE LISTING

```
<160> NUMBER OF SEQ ID NOS: 82

<210> SEQ ID NO 1
<211> LENGTH: 402
<212> TYPE: PRT
<213> ORGANISM: Mus musculus

<400> SEQUENCE: 1

Met Ala Asp Lys Ile Leu Arg Ala Lys Arg Lys Gln Phe Ile Asn Ser
1               5                   10                  15

Val Ser Ile Gly Thr Ile Asn Gly Leu Leu Asp Glu Leu Leu Glu Lys
            20                  25                  30

Arg Val Leu Asn Gln Glu Glu Met Asp Lys Ile Lys Leu Ala Asn Ile
        35                  40                  45

Thr Ala Met Asp Lys Ala Arg Asp Leu Cys Asp His Val Ser Lys Lys
    50                  55                  60

Gly Pro Gln Ala Ser Gln Ile Phe Ile Thr Tyr Ile Cys Asn Glu Asp
65                  70                  75                  80

Cys Tyr Leu Ala Gly Ile Leu Glu Leu Gln Ser Ala Pro Ser Ala Glu
                85                  90                  95

Thr Phe Val Ala Thr Glu Asp Ser Lys Gly Gly His Pro Ser Ser Ser
            100                 105                 110

Glu Thr Lys Glu Glu Gln Asn Lys Glu Asp Gly Thr Phe Pro Gly Leu
        115                 120                 125

Thr Gly Thr Leu Lys Phe Cys Pro Leu Glu Lys Ala Gln Lys Leu Trp
    130                 135                 140

Lys Glu Asn Pro Ser Glu Ile Tyr Pro Ile Met Asn Thr Thr Thr Arg
145                 150                 155                 160

Thr Arg Leu Ala Leu Ile Ile Cys Asn Thr Glu Phe Gln His Leu Ser
                165                 170                 175

Pro Arg Val Gly Ala Gln Val Asp Leu Arg Glu Met Lys Leu Leu Leu
            180                 185                 190

Glu Asp Leu Gly Tyr Thr Val Lys Val Lys Glu Asn Leu Thr Ala Leu
        195                 200                 205

Glu Met Val Lys Glu Val Lys Glu Phe Ala Ala Cys Pro Glu His Lys
    210                 215                 220

Thr Ser Asp Ser Thr Phe Leu Val Phe Met Ser His Gly Ile Gln Glu
225                 230                 235                 240

Gly Ile Cys Gly Thr Thr Tyr Ser Asn Glu Val Ser Asp Ile Leu Lys
                245                 250                 255

Val Asp Thr Ile Phe Gln Met Met Asn Thr Leu Lys Cys Pro Ser Leu
            260                 265                 270
```

Lys Asp Lys Pro Lys Val Ile Ile Ile Gln Ala Cys Arg Gly Glu Lys
            275                 280                 285

Gln Gly Val Val Leu Leu Lys Asp Ser Val Arg Asp Ser Glu Glu Asp
        290                 295                 300

Phe Leu Thr Asp Ala Ile Phe Glu Asp Asp Gly Ile Lys Lys Ala His
305                 310                 315                 320

Ile Glu Lys Asp Phe Ile Ala Phe Cys Ser Ser Thr Pro Asp Asn Val
                325                 330                 335

Ser Trp Arg His Pro Val Arg Gly Ser Leu Phe Ile Glu Ser Leu Ile
                340                 345                 350

Lys His Met Lys Glu Tyr Ala Trp Ser Cys Asp Leu Glu Asp Ile Phe
            355                 360                 365

Arg Lys Val Arg Phe Ser Phe Glu Gln Pro Glu Phe Arg Leu Gln Met
        370                 375                 380

Pro Thr Ala Asp Arg Val Thr Leu Thr Lys Arg Phe Tyr Leu Phe Pro
385                 390                 395                 400

Gly His

<210> SEQ ID NO 2
<211> LENGTH: 402
<212> TYPE: PRT
<213> ORGANISM: Artificial Sequence
<220> FEATURE:
<223> OTHER INFORMATION: CASP1_C285G

<400> SEQUENCE: 2

Met Ala Asp Lys Ile Leu Arg Ala Lys Arg Lys Gln Phe Ile Asn Ser
1               5                   10                  15

Val Ser Ile Gly Thr Ile Asn Gly Leu Leu Asp Glu Leu Leu Glu Lys
            20                  25                  30

Arg Val Leu Asn Gln Glu Glu Met Asp Lys Ile Lys Leu Ala Asn Ile
        35                  40                  45

Thr Ala Met Asp Lys Ala Arg Asp Leu Cys Asp His Val Ser Lys Lys
    50                  55                  60

Gly Pro Gln Ala Ser Gln Ile Phe Ile Thr Tyr Ile Cys Asn Glu Asp
65                  70                  75                  80

Cys Tyr Leu Ala Gly Ile Leu Glu Leu Gln Ser Ala Pro Ser Ala Glu
                85                  90                  95

Thr Phe Val Ala Thr Glu Asp Ser Lys Gly Gly His Pro Ser Ser Ser
            100                 105                 110

Glu Thr Lys Glu Glu Gln Asn Lys Glu Asp Gly Thr Phe Pro Gly Leu
        115                 120                 125

Thr Gly Thr Leu Lys Phe Cys Pro Leu Glu Lys Ala Gln Lys Leu Trp
130                 135                 140

Lys Glu Asn Pro Ser Glu Ile Tyr Pro Ile Met Asn Thr Thr Thr Arg
145                 150                 155                 160

Thr Arg Leu Ala Leu Ile Ile Cys Asn Thr Glu Phe Gln His Leu Ser
                165                 170                 175

Pro Arg Val Gly Ala Gln Val Asp Leu Arg Glu Met Lys Leu Leu Leu
            180                 185                 190

Glu Asp Leu Gly Tyr Thr Val Lys Val Lys Glu Asn Leu Thr Ala Leu
        195                 200                 205

Glu Met Val Lys Glu Val Lys Glu Phe Ala Ala Cys Pro Glu His Lys
    210                 215                 220

Thr Ser Asp Ser Thr Phe Leu Val Phe Met Ser His Gly Ile Gln Glu

-continued

```
            225                 230                 235                 240

Gly Ile Cys Gly Thr Thr Tyr Ser Asn Glu Val Ser Asp Ile Leu Lys
                        245                 250                 255

Val Asp Thr Ile Phe Gln Met Met Asn Thr Leu Lys Cys Pro Ser Leu
                        260                 265                 270

Lys Asp Lys Pro Lys Val Ile Ile Gln Ala Gly Arg Gly Glu Lys
                    275                 280                 285

Gln Gly Val Val Leu Leu Lys Asp Ser Val Arg Asp Ser Glu Glu Asp
                290                 295                 300

Phe Leu Thr Asp Ala Ile Phe Glu Asp Gly Ile Lys Lys Ala His
        305                 310                 315                 320

Ile Glu Lys Asp Phe Ile Ala Phe Cys Ser Thr Pro Asp Asn Val
                        325                 330                 335

Ser Trp Arg His Pro Val Arg Gly Ser Leu Phe Ile Glu Ser Leu Ile
                        340                 345                 350

Lys His Met Lys Glu Tyr Ala Trp Ser Cys Asp Leu Glu Asp Ile Phe
                        355                 360                 365

Arg Lys Val Arg Phe Ser Phe Glu Gln Pro Glu Phe Arg Leu Gln Met
                    370                 375                 380

Pro Thr Ala Asp Arg Val Thr Leu Thr Lys Arg Phe Tyr Leu Phe Pro
        385                 390                 395                 400

Gly His

<210> SEQ ID NO 3
<211> LENGTH: 326
<212> TYPE: PRT
<213> ORGANISM: Artificial Sequence
<220> FEATURE:
<223> OTHER INFORMATION: CASP1_RV

<400> SEQUENCE: 3

Met Val Leu Leu Lys Asp Ser Val Arg Asp Ser Glu Glu Asp Phe Leu
        1               5                   10                  15

Thr Asp Ala Ile Phe Glu Asp Gly Ile Lys Lys Ala His Ile Glu
                        20                  25                  30

Lys Asp Phe Ile Ala Phe Cys Ser Thr Pro Asp Asn Val Ser Trp
                        35                  40                  45

Arg His Pro Val Arg Gly Ser Leu Phe Ile Glu Ser Leu Ile Lys His
                    50                  55                  60

Met Lys Glu Tyr Ala Trp Ser Cys Asp Leu Glu Asp Ile Phe Arg Lys
        65                  70                  75                  80

Val Arg Phe Ser Phe Glu Gln Pro Glu Phe Arg Leu Gln Met Pro Thr
                        85                  90                  95

Ala Asp Arg Val Thr Leu Thr Lys Arg Phe Tyr Leu Phe Pro Gly His
                        100                 105                 110

Leu Leu Val Cys Asp Val Pro Ile Arg Ala Pro Ser Ala Glu Thr Phe
                    115                 120                 125

Val Ala Thr Glu Asp Ser Lys Gly Gly His Pro Ser Ser Ser Glu Thr
                130                 135                 140

Lys Glu Glu Gln Asn Lys Glu Asp Gly Thr Phe Pro Gly Leu Thr Gly
        145                 150                 155                 160

Thr Leu Lys Phe Cys Pro Leu Glu Lys Ala Gln Lys Leu Trp Lys Glu
                        165                 170                 175

Asn Pro Ser Glu Ile Tyr Pro Ile Met Asn Thr Thr Thr Arg Thr Arg
                        180                 185                 190
```

```
Leu Ala Leu Ile Ile Cys Asn Thr Glu Phe Gln His Leu Ser Pro Arg
            195                 200                 205

Val Gly Ala Gln Val Asp Leu Arg Glu Met Lys Leu Leu Leu Glu Asp
        210                 215                 220

Leu Gly Tyr Thr Val Lys Val Lys Glu Asn Leu Thr Ala Leu Glu Met
225                 230                 235                 240

Val Lys Glu Val Lys Glu Phe Ala Ala Cys Pro Glu His Lys Thr Ser
                245                 250                 255

Asp Ser Thr Phe Leu Val Phe Met Ser His Gly Ile Gln Glu Gly Ile
            260                 265                 270

Cys Gly Thr Thr Tyr Ser Asn Glu Val Ser Asp Ile Leu Lys Val Asp
        275                 280                 285

Thr Ile Phe Gln Met Met Asn Thr Leu Lys Cys Pro Ser Leu Lys Asp
    290                 295                 300

Lys Pro Lys Val Ile Ile Gln Ala Cys Arg Gly Glu Lys Gln Gly
305                 310                 315                 320

Val Val Leu Leu Lys Asp
            325

<210> SEQ ID NO 4
<211> LENGTH: 317
<212> TYPE: PRT
<213> ORGANISM: Artificial Sequence
<220> FEATURE:
<223> OTHER INFORMATION: CASP1_RV2

<400> SEQUENCE: 4

Met Ser Glu Glu Asp Phe Leu Thr Asp Ala Ile Phe Glu Asp Asp Gly
1               5                   10                  15

Ile Lys Lys Ala His Ile Glu Lys Asp Phe Ile Ala Phe Cys Ser Ser
            20                  25                  30

Thr Pro Asp Asn Val Ser Trp Arg His Pro Val Arg Gly Ser Leu Phe
        35                  40                  45

Ile Glu Ser Leu Ile Lys His Met Lys Glu Tyr Ala Trp Ser Cys Asp
    50                  55                  60

Leu Glu Asp Ile Phe Arg Lys Val Arg Phe Ser Phe Glu Gln Pro Glu
65                  70                  75                  80

Phe Arg Leu Gln Met Pro Thr Ala Asp Arg Val Thr Leu Thr Lys Arg
                85                  90                  95

Phe Tyr Leu Phe Pro Gly His Leu Leu Val Cys Asp Val Pro Ile Arg
            100                 105                 110

Ala Pro Ser Ala Glu Thr Phe Val Ala Thr Glu Asp Ser Lys Gly Gly
        115                 120                 125

His Pro Ser Ser Ser Glu Thr Lys Glu Glu Gln Asn Lys Glu Asp Gly
    130                 135                 140

Thr Phe Pro Gly Leu Thr Gly Thr Leu Lys Phe Cys Pro Leu Glu Lys
145                 150                 155                 160

Ala Gln Lys Leu Trp Lys Glu Asn Pro Ser Glu Ile Tyr Pro Ile Met
                165                 170                 175

Asn Thr Thr Thr Arg Thr Arg Leu Ala Leu Ile Ile Cys Asn Thr Glu
            180                 185                 190

Phe Gln His Leu Ser Pro Arg Val Gly Ala Gln Val Asp Leu Arg Glu
        195                 200                 205

Met Lys Leu Leu Leu Glu Asp Leu Gly Tyr Thr Val Lys Val Lys Glu
    210                 215                 220
```

```
Asn Leu Thr Ala Leu Glu Met Val Lys Glu Val Lys Glu Phe Ala Ala
225                 230                 235                 240

Cys Pro Glu His Lys Thr Ser Asp Ser Thr Phe Leu Val Phe Met Ser
                245                 250                 255

His Gly Ile Gln Glu Gly Ile Cys Gly Thr Thr Tyr Ser Asn Glu Val
            260                 265                 270

Ser Asp Ile Leu Lys Val Asp Thr Ile Phe Gln Met Met Asn Thr Leu
        275                 280                 285

Lys Cys Pro Ser Leu Lys Asp Lys Pro Lys Val Ile Ile Gln Ala
290                 295                 300

Cys Arg Gly Glu Lys Gln Gly Val Val Leu Leu Lys Asp
305                 310                 315

<210> SEQ ID NO 5
<211> LENGTH: 88
<212> TYPE: PRT
<213> ORGANISM: Artificial Sequence
<220> FEATURE:
<223> OTHER INFORMATION: Casp1 S, p10 (AA315-402)

<400> SEQUENCE: 5

Gly Ile Lys Lys Ala His Ile Glu Lys Asp Phe Ile Ala Phe Cys Ser
1               5                   10                  15

Ser Thr Pro Asp Asn Val Ser Trp Arg His Pro Val Arg Gly Ser Leu
            20                  25                  30

Phe Ile Glu Ser Leu Ile Lys His Met Lys Glu Tyr Ala Trp Ser Cys
        35                  40                  45

Asp Leu Glu Asp Ile Phe Arg Lys Val Arg Phe Ser Phe Glu Gln Pro
    50                  55                  60

Glu Phe Arg Leu Gln Met Pro Thr Ala Asp Arg Val Thr Leu Thr Lys
65                  70                  75                  80

Arg Phe Tyr Leu Phe Pro Gly His
                85

<210> SEQ ID NO 6
<211> LENGTH: 27
<212> TYPE: PRT
<213> ORGANISM: Mus musculus

<400> SEQUENCE: 6

Ala Pro Ser Ala Glu Thr Phe Val Ala Thr Glu Asp Ser Lys Gly Gly
1               5                   10                  15

His Pro Ser Ser Ser Glu Thr Lys Glu Glu Gln
            20                  25

<210> SEQ ID NO 7
<211> LENGTH: 9
<212> TYPE: PRT
<213> ORGANISM: Mus musculus

<400> SEQUENCE: 7

Leu Leu Val Cys Asp Val Pro Ile Arg
1               5

<210> SEQ ID NO 8
<211> LENGTH: 536
<212> TYPE: PRT
<213> ORGANISM: Artificial Sequence
<220> FEATURE:
<223> OTHER INFORMATION: iCASP1
```

<400> SEQUENCE: 8

Met Gly Ser Arg Gly Val Gln Val Glu Thr Ile Ser Pro Gly Asp Gly
1               5                   10                  15

Arg Thr Phe Pro Lys Arg Gly Gln Thr Cys Val Val His Tyr Thr Gly
            20                  25                  30

Met Leu Glu Asp Gly Lys Lys Val Asp Ser Ser Arg Asp Arg Asn Lys
        35                  40                  45

Pro Phe Lys Phe Met Leu Gly Lys Gln Glu Val Ile Arg Gly Trp Glu
    50                  55                  60

Glu Gly Val Ala Gln Met Ser Val Gly Gln Arg Ala Lys Leu Thr Ile
65              70                  75                  80

Ser Pro Asp Tyr Ala Tyr Gly Ala Thr Gly His Pro Gly Ile Ile Pro
                85                  90                  95

Pro His Ala Thr Leu Val Phe Asp Val Glu Leu Leu Lys Leu Glu Thr
            100                 105                 110

Arg Gly Val Gln Val Glu Thr Ile Ser Pro Gly Asp Gly Arg Thr Phe
        115                 120                 125

Pro Lys Arg Gly Gln Thr Cys Val Val His Tyr Thr Gly Met Leu Glu
    130                 135                 140

Asp Gly Lys Lys Val Asp Ser Ser Arg Asp Arg Asn Lys Pro Phe Lys
145                 150                 155                 160

Phe Met Leu Gly Lys Gln Glu Val Ile Arg Gly Trp Glu Glu Gly Val
                165                 170                 175

Ala Gln Met Ser Val Gly Gln Arg Ala Lys Leu Thr Ile Ser Pro Asp
            180                 185                 190

Tyr Ala Tyr Gly Ala Thr Gly His Pro Gly Ile Ile Pro Pro His Ala
        195                 200                 205

Thr Leu Val Phe Asp Val Glu Leu Leu Lys Leu Glu Ser Gly Gly Gly
210                 215                 220

Ser Ala Pro Ser Ala Glu Thr Phe Val Ala Thr Glu Asp Ser Lys Gly
225                 230                 235                 240

Gly His Pro Ser Ser Glu Thr Lys Glu Glu Gln Asn Lys Glu Asp
                245                 250                 255

Gly Thr Phe Pro Gly Leu Thr Gly Thr Leu Lys Phe Cys Pro Leu Glu
            260                 265                 270

Lys Ala Gln Lys Leu Trp Lys Glu Asn Pro Ser Glu Ile Tyr Pro Ile
        275                 280                 285

Met Asn Thr Thr Thr Arg Thr Arg Leu Ala Leu Ile Ile Cys Asn Thr
    290                 295                 300

Glu Phe Gln His Leu Ser Pro Arg Val Gly Ala Gln Val Asp Leu Arg
305                 310                 315                 320

Glu Met Lys Leu Leu Leu Glu Asp Leu Gly Tyr Thr Val Lys Val Lys
                325                 330                 335

Glu Asn Leu Thr Ala Leu Glu Met Val Lys Glu Val Lys Glu Phe Ala
            340                 345                 350

Ala Cys Pro Glu His Lys Thr Ser Asp Ser Thr Phe Leu Val Phe Met
        355                 360                 365

Ser His Gly Ile Gln Glu Gly Ile Cys Gly Thr Thr Tyr Ser Asn Glu
    370                 375                 380

Val Ser Asp Ile Leu Lys Val Asp Thr Ile Phe Gln Met Met Asn Thr
385                 390                 395                 400

Leu Lys Cys Pro Ser Leu Lys Asp Lys Pro Lys Val Ile Ile Ile Gln

```
                    405                 410                 415
Ala Cys Arg Gly Glu Lys Gln Gly Val Val Leu Leu Lys Asp Ser Val
                420                 425                 430

Arg Asp Ser Glu Glu Asp Phe Leu Thr Asp Ala Ile Phe Glu Asp Asp
            435                 440                 445

Gly Ile Lys Lys Ala His Ile Glu Lys Asp Phe Ile Ala Phe Cys Ser
        450                 455                 460

Ser Thr Pro Asp Asn Val Ser Trp Arg His Pro Val Arg Gly Ser Leu
465                 470                 475                 480

Phe Ile Glu Ser Leu Ile Lys His Met Lys Glu Tyr Ala Trp Ser Cys
                485                 490                 495

Asp Leu Glu Asp Ile Phe Arg Lys Val Arg Phe Ser Phe Glu Gln Pro
                500                 505                 510

Glu Phe Arg Leu Gln Met Pro Thr Ala Asp Arg Val Thr Leu Thr Lys
            515                 520                 525

Arg Phe Tyr Leu Phe Pro Gly His
        530                 535

<210> SEQ ID NO 9
<211> LENGTH: 5
<212> TYPE: PRT
<213> ORGANISM: Artificial Sequence
<220> FEATURE:
<223> OTHER INFORMATION: SGGGS linker

<400> SEQUENCE: 9

Ser Gly Gly Gly Ser
1               5

<210> SEQ ID NO 10
<211> LENGTH: 220
<212> TYPE: PRT
<213> ORGANISM: Artificial Sequence
<220> FEATURE:
<223> OTHER INFORMATION: F36V-FKBP

<400> SEQUENCE: 10

Met Gly Ser Arg Gly Val Gln Val Glu Thr Ile Ser Pro Gly Asp Gly
1               5                   10                  15

Arg Thr Phe Pro Lys Arg Gly Gln Thr Cys Val Val His Tyr Thr Gly
                20                  25                  30

Met Leu Glu Asp Gly Lys Lys Val Asp Ser Ser Arg Asp Arg Asn Lys
            35                  40                  45

Pro Phe Lys Phe Met Leu Gly Lys Gln Glu Val Ile Arg Gly Trp Glu
        50                  55                  60

Glu Gly Val Ala Gln Met Ser Val Gly Gln Arg Ala Lys Leu Thr Ile
65                  70                  75                  80

Ser Pro Asp Tyr Ala Tyr Gly Ala Thr Gly His Pro Gly Ile Ile Pro
                85                  90                  95

Pro His Ala Thr Leu Val Phe Asp Val Glu Leu Leu Lys Leu Glu Thr
            100                 105                 110

Arg Gly Val Gln Val Glu Thr Ile Ser Pro Gly Asp Gly Arg Thr Phe
        115                 120                 125

Pro Lys Arg Gly Gln Thr Cys Val Val His Tyr Thr Gly Met Leu Glu
    130                 135                 140

Asp Gly Lys Lys Val Asp Ser Ser Arg Asp Arg Asn Lys Pro Phe Lys
145                 150                 155                 160
```

```
Phe Met Leu Gly Lys Gln Glu Val Ile Arg Gly Trp Glu Glu Gly Val
                165                 170                 175

Ala Gln Met Ser Val Gly Gln Arg Ala Lys Leu Thr Ile Ser Pro Asp
            180                 185                 190

Tyr Ala Tyr Gly Ala Thr Gly His Pro Gly Ile Ile Pro Pro His Ala
        195                 200                 205

Thr Leu Val Phe Asp Val Glu Leu Leu Lys Leu Glu
    210                 215                 220

<210> SEQ ID NO 11
<211> LENGTH: 217
<212> TYPE: PRT
<213> ORGANISM: Artificial Sequence
<220> FEATURE:
<223> OTHER INFORMATION: F36M-FKBP

<400> SEQUENCE: 11

Met Gly Val Gln Val Glu Thr Ile Ser Pro Gly Asp Gly Arg Thr Phe
1               5                   10                  15

Pro Lys Arg Gly Gln Thr Cys Val Val His Tyr Thr Gly Met Leu Glu
            20                  25                  30

Asp Gly Lys Lys Met Asp Ser Ser Arg Asp Arg Asn Lys Pro Phe Lys
        35                  40                  45

Phe Met Leu Gly Lys Gln Glu Val Ile Arg Gly Trp Glu Glu Gly Val
    50                  55                  60

Ala Gln Met Ser Val Gly Gln Arg Ala Lys Leu Thr Ile Ser Pro Asp
65                  70                  75                  80

Tyr Ala Tyr Gly Ala Thr Gly His Pro Gly Ile Ile Pro Pro His Ala
                85                  90                  95

Thr Leu Val Phe Asp Val Glu Leu Leu Lys Leu Glu Thr Arg Gly Val
            100                 105                 110

Gln Val Glu Thr Ile Ser Pro Gly Asp Gly Arg Thr Phe Pro Lys Arg
        115                 120                 125

Gly Gln Thr Cys Val Val His Tyr Thr Gly Met Leu Glu Asp Gly Lys
    130                 135                 140

Lys Met Asp Ser Ser Arg Asp Arg Asn Lys Pro Phe Lys Phe Met Leu
145                 150                 155                 160

Gly Lys Gln Glu Val Ile Arg Gly Trp Glu Glu Gly Val Ala Gln Met
                165                 170                 175

Ser Val Gly Gln Arg Ala Lys Leu Thr Ile Ser Pro Asp Tyr Ala Tyr
            180                 185                 190

Gly Ala Thr Gly His Pro Gly Ile Ile Pro Pro His Ala Thr Leu Val
        195                 200                 205

Phe Asp Val Glu Leu Leu Lys Leu Glu
    210                 215

<210> SEQ ID NO 12
<211> LENGTH: 533
<212> TYPE: PRT
<213> ORGANISM: Artificial Sequence
<220> FEATURE:
<223> OTHER INFORMATION: dCASP1

<400> SEQUENCE: 12

Met Gly Val Gln Val Glu Thr Ile Ser Pro Gly Asp Gly Arg Thr Phe
1               5                   10                  15

Pro Lys Arg Gly Gln Thr Cys Val Val His Tyr Thr Gly Met Leu Glu
            20                  25                  30
```

```
Asp Gly Lys Lys Met Asp Ser Ser Arg Asp Arg Asn Lys Pro Phe Lys
         35                  40                  45
Phe Met Leu Gly Lys Gln Glu Val Ile Arg Gly Trp Glu Glu Gly Val
 50                  55                  60
Ala Gln Met Ser Val Gly Gln Arg Ala Lys Leu Thr Ile Ser Pro Asp
 65                  70                  75                  80
Tyr Ala Tyr Gly Ala Thr Gly His Pro Gly Ile Ile Pro Pro His Ala
                 85                  90                  95
Thr Leu Val Phe Asp Val Glu Leu Leu Lys Leu Glu Thr Arg Gly Val
            100                 105                 110
Gln Val Glu Thr Ile Ser Pro Gly Asp Gly Arg Thr Phe Pro Lys Arg
            115                 120                 125
Gly Gln Thr Cys Val Val His Tyr Thr Gly Met Leu Glu Asp Gly Lys
        130                 135                 140
Lys Met Asp Ser Ser Arg Asp Arg Asn Lys Pro Phe Lys Phe Met Leu
145                 150                 155                 160
Gly Lys Gln Glu Val Ile Arg Gly Trp Glu Glu Gly Val Ala Gln Met
                165                 170                 175
Ser Val Gly Gln Arg Ala Lys Leu Thr Ile Ser Pro Asp Tyr Ala Tyr
            180                 185                 190
Gly Ala Thr Gly His Pro Gly Ile Ile Pro Pro His Ala Thr Leu Val
            195                 200                 205
Phe Asp Val Glu Leu Leu Lys Leu Glu Ser Gly Gly Gly Ser Ala Pro
        210                 215                 220
Ser Ala Glu Thr Phe Val Ala Thr Glu Asp Ser Lys Gly His Pro
225                 230                 235                 240
Ser Ser Ser Glu Thr Lys Glu Glu Gln Asn Lys Glu Asp Gly Thr Phe
                245                 250                 255
Pro Gly Leu Thr Gly Thr Leu Lys Phe Cys Pro Leu Glu Lys Ala Gln
            260                 265                 270
Lys Leu Trp Lys Glu Asn Pro Ser Glu Ile Tyr Pro Ile Met Asn Thr
        275                 280                 285
Thr Thr Arg Thr Leu Ala Leu Ile Ile Cys Asn Thr Glu Phe Gln
        290                 295                 300
His Leu Ser Pro Arg Val Gly Ala Gln Val Asp Leu Arg Glu Met Lys
305                 310                 315                 320
Leu Leu Leu Glu Asp Leu Gly Tyr Thr Val Lys Val Lys Glu Asn Leu
                325                 330                 335
Thr Ala Leu Glu Met Val Lys Glu Val Lys Glu Phe Ala Ala Cys Pro
            340                 345                 350
Glu His Lys Thr Ser Asp Ser Thr Phe Leu Val Phe Met Ser His Gly
            355                 360                 365
Ile Gln Glu Gly Ile Cys Gly Thr Thr Tyr Ser Asn Glu Val Ser Asp
        370                 375                 380
Ile Leu Lys Val Asp Thr Ile Phe Gln Met Met Asn Thr Leu Lys Cys
385                 390                 395                 400
Pro Ser Leu Lys Asp Lys Pro Lys Val Ile Ile Gln Ala Cys Arg
                405                 410                 415
Gly Glu Lys Gln Gly Val Val Leu Leu Lys Asp Ser Val Arg Asp Ser
            420                 425                 430
Glu Glu Asp Phe Leu Thr Asp Ala Ile Phe Glu Asp Asp Gly Ile Lys
        435                 440                 445
```

```
Lys Ala His Ile Glu Lys Asp Phe Ile Ala Phe Cys Ser Ser Thr Pro
    450                 455                 460

Asp Asn Val Ser Trp Arg His Pro Val Arg Gly Ser Leu Phe Ile Glu
465                 470                 475                 480

Ser Leu Ile Lys His Met Lys Glu Tyr Ala Trp Ser Cys Asp Leu Glu
                485                 490                 495

Asp Ile Phe Arg Lys Val Arg Phe Ser Phe Glu Gln Pro Glu Phe Arg
                500                 505                 510

Leu Gln Met Pro Thr Ala Asp Arg Val Thr Leu Thr Lys Arg Phe Tyr
            515                 520                 525

Leu Phe Pro Gly His
        530
```

<210> SEQ ID NO 13
<211> LENGTH: 236
<212> TYPE: PRT
<213> ORGANISM: Artificial Sequence
<220> FEATURE:
<223> OTHER INFORMATION: dasher GFP

<400> SEQUENCE: 13

```
Met Thr Ala Leu Thr Glu Gly Ala Lys Leu Phe Glu Lys Glu Ile Pro
1               5                   10                  15

Tyr Ile Thr Glu Leu Glu Gly Asp Val Glu Gly Met Lys Phe Ile Ile
            20                  25                  30

Lys Gly Glu Gly Thr Gly Asp Ala Thr Thr Gly Thr Ile Lys Ala Lys
        35                  40                  45

Tyr Ile Cys Thr Thr Gly Asp Leu Pro Val Pro Trp Ala Thr Leu Val
    50                  55                  60

Ser Thr Leu Ser Tyr Gly Val Gln Cys Phe Ala Lys Tyr Pro Ser His
65                  70                  75                  80

Ile Lys Asp Phe Phe Lys Ser Ala Met Pro Glu Gly Tyr Thr Gln Glu
                85                  90                  95

Arg Thr Ile Ser Phe Glu Gly Asp Gly Val Tyr Lys Thr Arg Ala Met
            100                 105                 110

Val Thr Tyr Glu Arg Gly Ser Ile Tyr Asn Arg Val Thr Leu Thr Gly
        115                 120                 125

Glu Asn Phe Lys Lys Asp Gly His Ile Leu Arg Lys Asn Val Ala Phe
    130                 135                 140

Gln Cys Pro Pro Ser Ile Leu Tyr Ile Leu Pro Asp Thr Val Asn Asn
145                 150                 155                 160

Gly Ile Arg Val Glu Phe Asn Gln Ala Tyr Asp Ile Glu Gly Val Thr
                165                 170                 175

Glu Lys Leu Val Thr Lys Cys Ser Gln Met Asn Arg Pro Leu Ala Gly
            180                 185                 190

Ser Ala Ala Val His Ile Pro Arg Tyr His His Ile Thr Tyr His Thr
        195                 200                 205

Lys Leu Ser Lys Asp Arg Asp Glu Arg Arg Asp His Met Cys Leu Val
    210                 215                 220

Glu Val Val Lys Ala Val Asp Leu Asp Thr Tyr Gln
225                 230                 235
```

<210> SEQ ID NO 14
<211> LENGTH: 276
<212> TYPE: PRT
<213> ORGANISM: Mus musculus -continued

```
<400> SEQUENCE: 14

Met Pro Ser Ala Phe Glu Lys Val Val Lys Asn Val Ile Lys Glu Val
1               5                   10                  15

Ser Gly Ser Arg Gly Asp Leu Ile Pro Val Asp Ser Leu Arg Asn Ser
            20                  25                  30

Thr Ser Phe Arg Pro Tyr Cys Leu Leu Asn Arg Lys Phe Ser Ser Ser
        35                  40                  45

Arg Phe Trp Lys Pro Arg Tyr Ser Cys Val Asn Leu Ser Ile Lys Asp
    50                  55                  60

Ile Leu Glu Pro Ser Ala Pro Glu Pro Glu Pro Glu Cys Phe Gly Ser
65                  70                  75                  80

Phe Lys Val Ser Asp Val Val Asp Gly Asn Ile Gln Gly Arg Val Met
                85                  90                  95

Leu Ser Gly Met Gly Glu Gly Lys Ile Ser Gly Gly Ala Ala Val Ser
            100                 105                 110

Asp Ser Ser Ser Ala Ser Met Asn Val Cys Ile Leu Arg Val Thr Gln
        115                 120                 125

Lys Thr Trp Glu Thr Met Gln His Glu Arg His Leu Gln Gln Pro Glu
    130                 135                 140

Asn Lys Ile Leu Gln Gln Leu Arg Ser Arg Gly Asp Asp Leu Phe Val
145                 150                 155                 160

Val Thr Glu Val Leu Gln Thr Lys Glu Val Gln Ile Thr Glu Val
                165                 170                 175

His Ser Gln Glu Gly Ser Gly Gln Phe Thr Leu Pro Gly Ala Leu Cys
            180                 185                 190

Leu Lys Gly Glu Gly Lys Gly His Gln Ser Arg Lys Lys Met Val Thr
        195                 200                 205

Ile Pro Ala Gly Ser Ile Leu Ala Phe Arg Val Ala Gln Leu Leu Ile
    210                 215                 220

Gly Ser Lys Trp Asp Ile Leu Leu Val Ser Asp Glu Lys Gln Arg Thr
225                 230                 235                 240

Phe Glu Pro Ser Ser Gly Asp Arg Lys Ala Val Gly Gln Arg His His
                245                 250                 255

Gly Leu Asn Val Leu Ala Ala Leu Cys Ser Ile Gly Lys Gln Leu Ser
            260                 265                 270

Leu Leu Ser Asp
        275

<210> SEQ ID NO 15
<211> LENGTH: 284
<212> TYPE: PRT
<213> ORGANISM: Artificial Sequence
<220> FEATURE:
<223> OTHER INFORMATION: GSDMD_NTER_FLAG

<400> SEQUENCE: 15

Met Pro Ser Ala Phe Glu Lys Val Val Lys Asn Val Ile Lys Glu Val
1               5                   10                  15

Ser Gly Ser Arg Gly Asp Leu Ile Pro Val Asp Ser Leu Arg Asn Ser
            20                  25                  30

Thr Ser Phe Arg Pro Tyr Cys Leu Leu Asn Arg Lys Phe Ser Ser Ser
        35                  40                  45

Arg Phe Trp Lys Pro Arg Tyr Ser Cys Val Asn Leu Ser Ile Lys Asp
    50                  55                  60

Ile Leu Glu Pro Ser Ala Pro Glu Pro Glu Pro Glu Cys Phe Gly Ser
```

```
                65                  70                  75                  80
Phe Lys Val Ser Asp Val Val Asp Gly Asn Ile Gln Gly Arg Val Met
                    85                  90                  95

Leu Ser Gly Met Gly Glu Gly Lys Ile Ser Gly Gly Ala Ala Val Ser
            100                 105                 110

Asp Ser Ser Ala Ser Met Asn Val Cys Ile Leu Arg Val Thr Gln
        115                 120                 125

Lys Thr Trp Glu Thr Met Gln His Glu Arg His Leu Gln Gln Pro Glu
    130                 135                 140

Asn Lys Ile Leu Gln Gln Leu Arg Ser Arg Gly Asp Asp Leu Phe Val
145                 150                 155                 160

Val Thr Glu Val Leu Gln Thr Lys Glu Glu Val Gln Ile Thr Glu Val
                165                 170                 175

His Ser Gln Glu Gly Ser Gly Gln Phe Thr Leu Pro Gly Ala Leu Cys
            180                 185                 190

Leu Lys Gly Glu Gly Lys Gly His Gln Ser Arg Lys Lys Met Val Thr
        195                 200                 205

Ile Pro Ala Gly Ser Ile Leu Ala Phe Arg Val Ala Gln Leu Leu Ile
    210                 215                 220

Gly Ser Lys Trp Asp Ile Leu Val Ser Asp Glu Lys Gln Arg Thr
225                 230                 235                 240

Phe Glu Pro Ser Ser Gly Asp Arg Lys Ala Val Gly Gln Arg His His
                245                 250                 255

Gly Leu Asn Val Leu Ala Ala Leu Cys Ser Ile Gly Lys Gln Leu Ser
            260                 265                 270

Leu Leu Ser Asp Asp Tyr Lys Asp Asp Asp Lys
        275                 280

<210> SEQ ID NO 16
<211> LENGTH: 472
<212> TYPE: PRT
<213> ORGANISM: Artificial Sequence
<220> FEATURE:
<223> OTHER INFORMATION: MLKL_FLAG_MT

<400> SEQUENCE: 16

Met Asp Lys Leu Gly Gln Ile Ile Lys Leu Gly Gln Leu Ile Tyr Glu
1               5                   10                  15

Gln Cys Glu Lys Met Lys Tyr Cys Arg Lys Gln Cys Gln Arg Leu Gly
                20                  25                  30

Asn Arg Val His Gly Leu Leu Gln Pro Leu Gln Arg Leu Gln Ala Gln
            35                  40                  45

Gly Lys Lys Asn Leu Pro Asp Asp Ile Thr Ala Ala Leu Gly Arg Phe
        50                  55                  60

Asp Glu Val Leu Lys Glu Ala Asn Gln Gln Ile Glu Lys Phe Ser Lys
65                  70                  75                  80

Lys Ser His Ile Trp Lys Phe Val Ser Val Gly Asn Asp Lys Ile Leu
                85                  90                  95

Phe His Glu Val Asn Glu Lys Leu Arg Asp Val Trp Glu Glu Leu Leu
            100                 105                 110

Leu Leu Leu Gln Val Tyr His Trp Asn Thr Val Ser Asp Val Ser Gln
        115                 120                 125

Pro Ala Ser Trp Gln Gln Glu Asp Arg Gln Asp Ala Glu Glu Asp Gly
    130                 135                 140

Asn Glu Asn Met Lys Val Ile Leu Met Gln Leu Gln Ile Ser Val Glu
```

```
            145                 150                 155                 160
    Glu Ile Asn Lys Thr Leu Lys Gln Cys Ser Leu Lys Pro Thr Gln Glu
                    165                 170                 175

Ile Pro Gln Asp Leu Gln Ile Lys Glu Ile Pro Lys Glu His Leu Gly
                    180                 185                 190

Pro Pro Trp Thr Lys Leu Lys Thr Ser Lys Met Ser Thr Ile Tyr Arg
                    195                 200                 205

Gly Glu Tyr His Arg Ser Pro Val Thr Ile Lys Val Phe Asn Asn Pro
                    210                 215                 220

Gln Ala Glu Ser Val Gly Ile Val Arg Phe Thr Phe Asn Asp Glu Ile
    225                 230                 235                 240

Lys Thr Met Lys Lys Phe Asp Ser Pro Asn Ile Leu Arg Ile Phe Gly
                    245                 250                 255

Ile Cys Ile Asp Gln Thr Val Lys Pro Pro Glu Phe Ser Ile Val Met
                    260                 265                 270

Glu Tyr Cys Glu Leu Gly Thr Leu Arg Glu Leu Leu Asp Arg Glu Lys
                    275                 280                 285

Asp Leu Thr Met Ser Val Arg Ser Leu Leu Val Leu Arg Ala Ala Arg
                    290                 295                 300

Gly Leu Tyr Arg Leu His His Ser Glu Thr Leu His Arg Asn Ile Ser
    305                 310                 315                 320

Ser Ser Ser Phe Leu Val Ala Gly Gly Tyr Gln Val Lys Leu Ala Gly
                    325                 330                 335

Phe Glu Leu Ser Lys Thr Ala Asn Ser Ile Ser Arg Thr Ala Lys Ser
                    340                 345                 350

Thr Lys Ala Glu Arg Ser Ser Ser Thr Ile Tyr Val Ser Pro Glu Arg
                    355                 360                 365

Leu Lys Asn Pro Phe Cys Leu Tyr Asp Ile Lys Ala Glu Ile Tyr Ser
                    370                 375                 380

Phe Gly Ile Val Leu Trp Glu Ile Ala Thr Gly Lys Ile Pro Phe Glu
    385                 390                 395                 400

Gly Cys Asp Ser Lys Lys Ile Arg Glu Leu Val Ala Glu Asp Lys Lys
                    405                 410                 415

Gln Glu Pro Val Gly Gln Asp Cys Pro Glu Leu Leu Arg Glu Ile Ile
                    420                 425                 430

Asn Glu Cys Arg Ala His Glu Pro Ser Gln Arg Pro Ser Val Asp Gly
                    435                 440                 445

Ile Leu Glu Arg Leu Ser Ala Val Glu Glu Ser Thr Asp Lys Lys Val
                    450                 455                 460

Asp Tyr Lys Asp Asp Asp Lys
    465                 470

<210> SEQ ID NO 17
<211> LENGTH: 173
<212> TYPE: PRT
<213> ORGANISM: Mus musculus

<400> SEQUENCE: 17

Met Asn Asn Arg Trp Ile Leu His Ala Ala Phe Leu Leu Cys Phe Ser
    1               5                   10                  15

Thr Thr Ala Leu Ser Val Pro Ile Arg Gln Leu His Tyr Arg Leu Arg
                    20                  25                  30

Asp Glu Gln Gln Lys Ser Leu Val Leu Ser Asp Pro Tyr Glu Leu Lys
                    35                  40                  45
```

```
Ala Leu His Leu Asn Gly Gln Asn Ile Asn Gln Gln Val Ile Phe Ser
    50                  55                  60

Met Ser Phe Val Gln Gly Glu Pro Ser Asn Asp Lys Ile Pro Val Ala
 65                  70                  75                  80

Leu Gly Leu Lys Gly Lys Asn Leu Tyr Leu Ser Cys Val Met Lys Asp
                 85                  90                  95

Gly Thr Pro Thr Leu Gln Leu Glu Ser Val Asp Pro Lys Gln Tyr Pro
             100                 105                 110

Lys Lys Lys Met Glu Lys Arg Phe Val Phe Asn Lys Ile Glu Val Lys
             115                 120                 125

Ser Lys Val Glu Phe Glu Ser Ala Glu Phe Pro Asn Trp Tyr Ile Ser
130                 135                 140

Thr Ser Gln Ala Glu His Lys Pro Val Phe Leu Gly Asn Asn Ser Gly
145                 150                 155                 160

Gln Asp Ile Ile Asp Phe Thr Met Glu Ser Val Ser Ser
                165                 170

<210> SEQ ID NO 18
<211> LENGTH: 182
<212> TYPE: PRT
<213> ORGANISM: Mus musculus

<400> SEQUENCE: 18

Met Asn Asn Arg Trp Ile Leu His Ala Ala Phe Leu Leu Cys Phe Ser
 1               5                  10                  15

Thr Thr Ala Leu Ser Ile Asn Tyr Lys Gln Leu Gln Leu Gln Glu Arg
             20                  25                  30

Thr Asn Ile Arg Lys Cys Gln Glu Leu Leu Glu Gln Leu Asn Gly Lys
         35                  40                  45

Ile Asn Leu Thr Tyr Arg Ala Asp Phe Lys Ile Pro Met Glu Met Thr
    50                  55                  60

Glu Lys Met Gln Lys Ser Tyr Thr Ala Phe Ala Ile Gln Glu Met Leu
 65                  70                  75                  80

Gln Asn Val Phe Leu Val Phe Arg Asn Asn Phe Ser Ser Thr Gly Trp
                 85                  90                  95

Asn Glu Thr Ile Val Val Arg Leu Leu Asp Glu Leu His Gln Gln Thr
             100                 105                 110

Val Phe Leu Lys Thr Val Leu Glu Glu Lys Gln Glu Glu Arg Leu Thr
             115                 120                 125

Trp Glu Met Ser Ser Thr Ala Leu His Leu Lys Ser Tyr Tyr Trp Arg
130                 135                 140

Val Gln Arg Tyr Leu Lys Leu Met Lys Tyr Asn Ser Tyr Ala Trp Met
145                 150                 155                 160

Val Val Arg Ala Glu Ile Phe Arg Asn Phe Leu Ile Ile Arg Arg Leu
                165                 170                 175

Thr Arg Asn Phe Gln Asn
            180

<210> SEQ ID NO 19
<211> LENGTH: 292
<212> TYPE: PRT
<213> ORGANISM: Artificial Sequence
<220> FEATURE:
<223> OTHER INFORMATION: Ddx58_FLAG_RIGI_NTER

<400> SEQUENCE: 19

Met Asp Tyr Lys Asp Asp Asp Asp Lys Thr Ala Glu Gln Arg Gln Asn
```

```
                1               5                  10                  15
            Leu Gln Ala Phe Arg Asp Tyr Ile Lys Lys Ile Leu Asp Pro Thr Tyr
                            20                  25                  30
            Ile Leu Ser Tyr Met Ser Ser Trp Leu Glu Asp Glu Glu Val Gln Tyr
                            35                  40                  45
            Ile Gln Ala Glu Lys Asn Asn Lys Gly Pro Met Glu Ala Ala Ser Leu
                    50                  55                  60
            Phe Leu Gln Tyr Leu Leu Lys Leu Gln Ser Glu Gly Trp Phe Gln Ala
            65                  70                  75                  80
            Phe Leu Asp Ala Leu Tyr His Ala Gly Tyr Cys Gly Leu Cys Glu Ala
                            85                  90                  95
            Ile Glu Ser Trp Asp Phe Gln Lys Ile Glu Lys Leu Glu Glu His Arg
                            100                 105                 110
            Leu Leu Leu Arg Arg Leu Glu Pro Glu Phe Lys Ala Thr Val Asp Pro
                    115                 120                 125
            Asn Asp Ile Leu Ser Glu Leu Ser Glu Cys Leu Ile Asn Gln Glu Cys
                    130                 135                 140
            Glu Glu Ile Arg Gln Ile Arg Asp Thr Lys Gly Arg Met Ala Gly Ala
            145                 150                 155                 160
            Glu Lys Met Ala Glu Cys Leu Ile Arg Ser Asp Lys Glu Asn Trp Pro
                            165                 170                 175
            Lys Val Leu Gln Leu Ala Leu Glu Lys Asp Asn Ser Lys Phe Ser Glu
                            180                 185                 190
            Leu Trp Ile Val Asp Lys Gly Phe Lys Arg Ala Glu Ser Lys Ala Asp
                    195                 200                 205
            Glu Asp Asp Gly Ala Glu Ala Ser Ser Ile Gln Ile Phe Ile Gln Glu
                    210                 215                 220
            Glu Pro Glu Cys Gln Asn Leu Ser Gln Asn Pro Gly Pro Pro Ser Glu
            225                 230                 235                 240
            Ala Ser Ser Asn Asn Leu His Ser Pro Leu Lys Pro Arg Asn Tyr Gln
                            245                 250                 255
            Leu Glu Leu Ala Leu Pro Ala Lys Lys Gly Lys Asn Thr Ile Ile Cys
                            260                 265                 270
            Ala Pro Thr Gly Cys Gly Lys Thr Phe Val Ser Leu Leu Ile Cys Glu
                    275                 280                 285
            His His Leu Lys
                    290

<210> SEQ ID NO 20
<211> LENGTH: 41
<212> TYPE: PRT
<213> ORGANISM: Artificial Sequence
<220> FEATURE:
<223> OTHER INFORMATION: Reps1 non relevant protein

<400> SEQUENCE: 20

Met Lys Lys Val Val Asn Gly Arg Val Leu Glu Leu Phe Arg Ala
            1               5                   10                  15

Ala Gln Leu Ala Asn Asp Val Val Leu Gln Ile Met Glu Leu Cys Gly
                        20                  25                  30

Ala Thr Arg Leu Gly Tyr Phe Gly Arg
                        35                  40

<210> SEQ ID NO 21
<211> LENGTH: 269
<212> TYPE: PRT
```

<213> ORGANISM: Mus musculus

<400> SEQUENCE: 21

Met Ala Thr Val Pro Glu Leu Asn Cys Glu Met Pro Pro Phe Asp Ser
1               5                   10                  15

Asp Glu Asn Asp Leu Phe Phe Glu Val Asp Gly Pro Gln Lys Met Lys
            20                  25                  30

Gly Cys Phe Gln Thr Phe Asp Leu Gly Cys Pro Asp Glu Ser Ile Gln
        35                  40                  45

Leu Gln Ile Ser Gln Gln His Ile Asn Lys Ser Phe Arg Gln Ala Val
    50                  55                  60

Ser Leu Ile Val Ala Val Glu Lys Leu Trp Gln Leu Pro Val Ser Phe
65                  70                  75                  80

Pro Trp Thr Phe Gln Asp Glu Asp Met Ser Thr Phe Phe Ser Phe Ile
                85                  90                  95

Phe Glu Glu Glu Pro Ile Leu Cys Asp Ser Trp Asp Asp Asp Asn
            100                 105                 110

Leu Leu Val Cys Asp Val Pro Ile Arg Gln Leu His Tyr Arg Leu Arg
        115                 120                 125

Asp Glu Gln Gln Lys Ser Leu Val Leu Ser Asp Pro Tyr Glu Leu Lys
    130                 135                 140

Ala Leu His Leu Asn Gly Gln Asn Ile Asn Gln Gln Val Ile Phe Ser
145                 150                 155                 160

Met Ser Phe Val Gln Gly Glu Pro Ser Asn Asp Lys Ile Pro Val Ala
                165                 170                 175

Leu Gly Leu Lys Gly Lys Asn Leu Tyr Leu Ser Cys Val Met Lys Asp
            180                 185                 190

Gly Thr Pro Thr Leu Gln Leu Glu Ser Val Asp Pro Lys Gln Tyr Pro
        195                 200                 205

Lys Lys Lys Met Glu Lys Arg Phe Val Phe Asn Lys Ile Glu Val Lys
    210                 215                 220

Ser Lys Val Glu Phe Glu Ser Ala Glu Phe Pro Asn Trp Tyr Ile Ser
225                 230                 235                 240

Thr Ser Gln Ala Glu His Lys Pro Val Phe Leu Gly Asn Asn Ser Gly
                245                 250                 255

Gln Asp Ile Ile Asp Phe Thr Met Glu Ser Val Ser Ser
            260                 265

<210> SEQ ID NO 22
<211> LENGTH: 173
<212> TYPE: PRT
<213> ORGANISM: Mus musculus

<400> SEQUENCE: 22

Met Asn Asn Arg Trp Ile Leu His Ala Ala Phe Leu Leu Cys Phe Ser
1               5                   10                  15

Thr Thr Ala Leu Ser Val Pro Ile Arg Gln Leu His Tyr Arg Leu Arg
            20                  25                  30

Asp Glu Gln Gln Lys Ser Leu Val Leu Ser Asp Pro Tyr Glu Leu Lys
        35                  40                  45

Ala Leu His Leu Asn Gly Gln Asn Ile Asn Gln Gln Val Ile Phe Ser
    50                  55                  60

Met Ser Phe Val Gln Gly Glu Pro Ser Asn Asp Lys Ile Pro Val Ala
65                  70                  75                  80

Leu Gly Leu Lys Gly Lys Asn Leu Tyr Leu Ser Cys Val Met Lys Asp

```
                85                  90                  95
Gly Thr Pro Thr Leu Gln Leu Glu Ser Val Asp Pro Lys Gln Tyr Pro
            100                 105                 110
Lys Lys Lys Met Glu Lys Arg Phe Val Phe Asn Lys Ile Glu Val Lys
            115                 120                 125
Ser Lys Val Glu Phe Glu Ser Ala Glu Phe Pro Asn Trp Tyr Ile Ser
130                 135                 140
Thr Ser Gln Ala Glu His Lys Pro Val Phe Leu Gly Asn Asn Ser Gly
145                 150                 155                 160
Gln Asp Ile Ile Asp Phe Thr Met Glu Ser Val Ser Ser
                165                 170
```

<210> SEQ ID NO 23
<211> LENGTH: 189
<212> TYPE: PRT
<213> ORGANISM: Artificial Sequence
<220> FEATURE:
<223> OTHER INFORMATION: polyepitope vaccine

<400> SEQUENCE: 23

```
Met Ala Glu Ala Gly Gln Ser Leu Val Ile Ser Ala Ser Ile Ile Val
1               5                   10                  15
Phe Asn Leu Leu Glu Leu Glu Gly Asp Tyr Arg Asp Asp His Ile Phe
                20                  25                  30
Ser Leu Tyr Phe Met Ala Ala Lys Val Val Val Asn Gly Arg Val
            35                  40                  45
Leu Glu Leu Phe Arg Ala Ala Gln Leu Ala Asn Asp Val Val Leu Gln
50                  55                  60
Ile Met Glu Leu Cys Gly Ala Thr Arg Leu Gly Ala Ala Ala Asp Ile
65                  70                  75                  80
Pro Thr Gly Ile Pro Val His Leu Glu Leu Ala Ser Met Thr Asn Met
                85                  90                  95
Glu Leu Met Ser Ser Ile Val His Gln Gln Val Phe Pro Thr Val Ala
            100                 105                 110
Ser Ala Ala Gly Ile Ser Ser Ala Glu Ser Leu Lys Ile Ser Gln
            115                 120                 125
Ala Val His Ala Ala His Ala Glu Ile Asn Glu Ala Gly Arg Glu Val
            130                 135                 140
Val Gly Ser Ala Glu Ala Gly Ala Ala Ala Leu Leu Pro Asp Glu Val
145                 150                 155                 160
Ser Gly Leu Glu Gln Leu Glu Ser Ile Ile Asn Phe Glu Lys Leu Thr
                165                 170                 175
Glu Trp Thr Ser Ser Asn Val Met Glu Glu Arg Lys Ile
            180                 185
```

<210> SEQ ID NO 24
<211> LENGTH: 141
<212> TYPE: PRT
<213> ORGANISM: Mus musculus

<400> SEQUENCE: 24

```
Met Trp Leu Gln Asn Leu Leu Phe Leu Gly Ile Val Val Tyr Ser Leu
1               5                   10                  15
Ser Ala Pro Thr Arg Ser Pro Ile Thr Val Thr Arg Pro Trp Lys His
                20                  25                  30
Val Glu Ala Ile Lys Glu Ala Leu Asn Leu Leu Asp Asp Met Pro Val
            35                  40                  45
```

```
Thr Leu Asn Glu Glu Val Glu Val Val Ser Asn Glu Phe Ser Phe Lys
 50                  55                  60

Lys Leu Thr Cys Val Gln Thr Arg Leu Lys Ile Phe Glu Gln Gly Leu
 65                  70                  75                  80

Arg Gly Asn Phe Thr Lys Leu Lys Gly Ala Leu Asn Met Thr Ala Ser
                 85                  90                  95

Tyr Tyr Gln Thr Tyr Cys Pro Pro Thr Pro Glu Thr Asp Cys Glu Thr
                100                 105                 110

Gln Val Thr Thr Tyr Ala Asp Phe Ile Asp Ser Leu Lys Thr Phe Leu
            115                 120                 125

Thr Asp Ile Pro Phe Glu Cys Lys Lys Pro Gly Gln Lys
130                 135                 140

<210> SEQ ID NO 25
<211> LENGTH: 35
<212> TYPE: PRT
<213> ORGANISM: Artificial Sequence
<220> FEATURE:
<223> OTHER INFORMATION: Dpagt1 tumor specific adjuvant

<400> SEQUENCE: 25

Glu Ala Gly Gln Ser Leu Val Ile Ser Ala Ser Ile Ile Val Phe Asn
1                   5                  10                  15

Leu Leu Glu Leu Glu Gly Asp Tyr Arg Asp Asp His Ile Phe Ser Leu
                20                  25                  30

Tyr Phe Met
        35

<210> SEQ ID NO 26
<211> LENGTH: 35
<212> TYPE: PRT
<213> ORGANISM: Artificial Sequence
<220> FEATURE:
<223> OTHER INFORMATION: Reps1 tumor specific adjuvant

<400> SEQUENCE: 26

Lys Val Val Val Asn Gly Arg Val Leu Glu Leu Phe Arg Ala Ala Gln
1                   5                  10                  15

Leu Ala Asn Asp Val Val Leu Gln Ile Met Glu Leu Cys Gly Ala Thr
                20                  25                  30

Arg Leu Gly
        35

<210> SEQ ID NO 27
<211> LENGTH: 35
<212> TYPE: PRT
<213> ORGANISM: Artificial Sequence
<220> FEATURE:
<223> OTHER INFORMATION: Adpgk tumor-specific adjuvant

<400> SEQUENCE: 27

Asp Ile Pro Thr Gly Ile Pro Val His Leu Glu Leu Ala Ser Met Thr
1                   5                  10                  15

Asn Met Glu Leu Met Ser Ser Ile Val His Gln Gln Val Phe Pro Thr
                20                  25                  30

Val Ala Ser
        35

<210> SEQ ID NO 28
<211> LENGTH: 35
```

```
<212> TYPE: PRT
<213> ORGANISM: Gallus gallus

<400> SEQUENCE: 28

Gly Ile Ser Ser Ala Glu Ser Leu Lys Ile Ser Gln Ala Val His Ala
1               5                   10                  15

Ala His Ala Glu Ile Asn Glu Ala Gly Arg Glu Val Val Gly Ser Ala
            20                  25                  30

Glu Ala Gly
        35

<210> SEQ ID NO 29
<211> LENGTH: 35
<212> TYPE: PRT
<213> ORGANISM: Gallus gallus

<400> SEQUENCE: 29

Leu Leu Pro Asp Glu Val Ser Gly Leu Glu Gln Leu Glu Ser Ile Ile
1               5                   10                  15

Asn Phe Glu Lys Leu Thr Glu Trp Thr Ser Ser Asn Val Met Glu Glu
            20                  25                  30

Arg Lys Ile
        35

<210> SEQ ID NO 30
<211> LENGTH: 3
<212> TYPE: PRT
<213> ORGANISM: Artificial Sequence
<220> FEATURE:
<223> OTHER INFORMATION: spacer

<400> SEQUENCE: 30

Ala Ala Ala
1

<210> SEQ ID NO 31
<211> LENGTH: 312
<212> TYPE: PRT
<213> ORGANISM: Mus musculus

<400> SEQUENCE: 31

Met Gly Ser Thr Ala Arg Thr Gly His Phe Val Asp Gln His Arg Gln
1               5                   10                  15

Ala Leu Ile Ala Arg Val Thr Glu Val Asp Gly Val Leu Asp Ala Leu
            20                  25                  30

His Gly Ser Val Leu Thr Glu Gly Gln Tyr Gln Ala Val Arg Ala Glu
        35                  40                  45

Thr Thr Ser Gln Asp Lys Met Arg Lys Leu Phe Ser Phe Val Pro Ser
    50                  55                  60

Trp Asn Leu Thr Cys Lys Asp Ser Leu Leu Gln Ala Leu Lys Glu Ile
65              70                  75                  80

His Pro Tyr Leu Val Met Asp Leu Glu Gln Ser Gly Gly Gly Gly Ser
            85                  90                  95

Gly Val Gln Val Glu Thr Ile Ser Pro Gly Asp Gly Arg Thr Phe Pro
            100                 105                 110

Lys Arg Gly Gln Thr Cys Val Val His Tyr Thr Gly Met Leu Glu Asp
        115                 120                 125

Gly Lys Lys Met Asp Ser Ser Arg Asp Arg Asn Lys Pro Phe Lys Phe
    130                 135                 140
```

```
Met Leu Gly Lys Gln Glu Val Ile Arg Gly Trp Glu Glu Gly Val Ala
145                 150                 155                 160

Gln Met Ser Val Gly Gln Arg Ala Lys Leu Thr Ile Ser Pro Asp Tyr
            165                 170                 175

Ala Tyr Gly Ala Thr Gly His Pro Gly Ile Ile Pro Pro His Ala Thr
        180                 185                 190

Leu Val Phe Asp Val Glu Leu Leu Lys Leu Glu Thr Arg Gly Val Gln
    195                 200                 205

Val Glu Thr Ile Ser Pro Gly Asp Gly Arg Thr Phe Pro Lys Arg Gly
210                 215                 220

Gln Thr Cys Val Val His Tyr Thr Gly Met Leu Glu Asp Gly Lys Lys
225                 230                 235                 240

Met Asp Ser Ser Arg Asp Arg Asn Lys Pro Phe Lys Phe Met Leu Gly
            245                 250                 255

Lys Gln Glu Val Ile Arg Gly Trp Glu Glu Gly Val Ala Gln Met Ser
        260                 265                 270

Val Gly Gln Arg Ala Lys Leu Thr Ile Ser Pro Asp Tyr Ala Tyr Gly
    275                 280                 285

Ala Thr Gly His Pro Gly Ile Ile Pro Pro His Ala Thr Leu Val Phe
290                 295                 300

Asp Val Glu Leu Leu Lys Leu Glu
305                 310

<210> SEQ ID NO 32
<211> LENGTH: 495
<212> TYPE: PRT
<213> ORGANISM: Artificial Sequence
<220> FEATURE:
<223> OTHER INFORMATION: GSDMD_WT_FLAG

<400> SEQUENCE: 32

Met Pro Ser Ala Phe Glu Lys Val Val Lys Asn Val Ile Lys Glu Val
1               5                   10                  15

Ser Gly Ser Arg Gly Asp Leu Ile Pro Val Asp Ser Leu Arg Asn Ser
            20                  25                  30

Thr Ser Phe Arg Pro Tyr Cys Leu Leu Asn Arg Lys Phe Ser Ser Ser
        35                  40                  45

Arg Phe Trp Lys Pro Arg Tyr Ser Cys Val Asn Leu Ser Ile Lys Asp
    50                  55                  60

Ile Leu Glu Pro Ser Ala Pro Glu Pro Glu Pro Glu Cys Phe Gly Ser
65                  70                  75                  80

Phe Lys Val Ser Asp Val Val Asp Gly Asn Ile Gln Gly Arg Val Met
                85                  90                  95

Leu Ser Gly Met Gly Glu Gly Lys Ile Ser Gly Gly Ala Ala Val Ser
            100                 105                 110

Asp Ser Ser Ser Ala Ser Met Asn Val Cys Ile Leu Arg Val Thr Gln
        115                 120                 125

Lys Thr Trp Glu Thr Met Gln His Glu Arg His Leu Gln Gln Pro Glu
    130                 135                 140

Asn Lys Ile Leu Gln Gln Leu Arg Ser Arg Gly Asp Asp Leu Phe Val
145                 150                 155                 160

Val Thr Glu Val Leu Gln Thr Lys Glu Glu Val Gln Ile Thr Glu Val
                165                 170                 175

His Ser Gln Glu Gly Ser Gly Gln Phe Thr Leu Pro Gly Ala Leu Cys
            180                 185                 190
```

```
Leu Lys Gly Glu Gly Lys Gly His Gln Ser Arg Lys Met Val Thr
            195                 200                 205
Ile Pro Ala Gly Ser Ile Leu Ala Phe Arg Val Ala Gln Leu Leu Ile
210                 215                 220
Gly Ser Lys Trp Asp Ile Leu Leu Val Ser Asp Glu Lys Gln Arg Thr
225                 230                 235                 240
Phe Glu Pro Ser Ser Gly Asp Arg Lys Ala Val Gly Gln Arg His His
                245                 250                 255
Gly Leu Asn Val Leu Ala Ala Leu Cys Ser Ile Gly Lys Gln Leu Ser
            260                 265                 270
Leu Leu Ser Asp Gly Ile Asp Glu Glu Glu Leu Ile Glu Ala Ala Asp
            275                 280                 285
Phe Gln Gly Leu Tyr Ala Glu Val Lys Ala Cys Ser Ser Glu Leu Glu
290                 295                 300
Ser Leu Glu Met Glu Leu Arg Gln Gln Ile Leu Val Asn Ile Gly Lys
305                 310                 315                 320
Ile Leu Gln Asp Gln Pro Ser Met Glu Ala Leu Glu Ala Ser Leu Gly
                325                 330                 335
Gln Gly Leu Cys Ser Gly Gly Gln Val Glu Pro Leu Asp Gly Pro Ala
            340                 345                 350
Gly Cys Ile Leu Glu Cys Leu Val Leu Asp Ser Gly Glu Leu Val Pro
            355                 360                 365
Glu Leu Ala Ala Pro Ile Phe Tyr Leu Leu Gly Ala Leu Ala Val Leu
            370                 375                 380
Ser Glu Thr Gln Gln Gln Leu Leu Ala Lys Ala Leu Glu Thr Thr Val
385                 390                 395                 400
Leu Ser Lys Gln Leu Glu Leu Val Lys His Val Leu Glu Gln Ser Thr
                405                 410                 415
Pro Trp Gln Glu Gln Ser Ser Val Ser Leu Pro Thr Val Leu Leu Gly
            420                 425                 430
Asp Cys Trp Asp Glu Lys Asn Pro Thr Trp Val Leu Leu Glu Glu Cys
            435                 440                 445
Gly Leu Arg Leu Gln Val Glu Ser Pro Gln Val His Trp Glu Pro Thr
450                 455                 460
Ser Leu Ile Pro Thr Ser Ala Leu Tyr Ala Ser Leu Phe Leu Leu Ser
465                 470                 475                 480
Ser Leu Gly Gln Lys Pro Cys Asp Tyr Lys Asp Asp Asp Lys
                485                 490                 495

<210> SEQ ID NO 33
<211> LENGTH: 173
<212> TYPE: PRT
<213> ORGANISM: Artificial Sequence
<220> FEATURE:
<223> OTHER INFORMATION: IL1B_CALRSP

<400> SEQUENCE: 33

Met Gly Leu Leu Ser Val Pro Leu Leu Leu Gly Leu Leu Gly Leu Ala
1               5                   10                  15
Ala Ala Asp Pro Ala Val Pro Ile Arg Gln Leu His Tyr Arg Leu Arg
            20                  25                  30
Asp Glu Gln Gln Lys Ser Leu Val Leu Ser Asp Pro Tyr Glu Leu Lys
        35                  40                  45
Ala Leu His Leu Asn Gly Gln Asn Ile Asn Gln Gln Val Ile Phe Ser
    50                  55                  60
```

Met Ser Phe Val Gln Gly Glu Pro Ser Asn Asp Lys Ile Pro Val Ala
65                  70                  75                  80

Leu Gly Leu Lys Gly Lys Asn Leu Tyr Leu Ser Cys Val Met Lys Asp
                85                  90                  95

Gly Thr Pro Thr Leu Gln Leu Glu Ser Val Asp Pro Lys Gln Tyr Pro
            100                 105                 110

Lys Lys Lys Met Glu Lys Arg Phe Val Phe Asn Lys Ile Glu Val Lys
        115                 120                 125

Ser Lys Val Glu Phe Glu Ser Ala Glu Phe Pro Asn Trp Tyr Ile Ser
    130                 135                 140

Thr Ser Gln Ala Glu His Lys Pro Val Phe Leu Gly Asn Asn Ser Gly
145                 150                 155                 160

Gln Asp Ile Ile Asp Phe Thr Met Glu Ser Val Ser Ser
                165                 170

<210> SEQ ID NO 34
<211> LENGTH: 178
<212> TYPE: PRT
<213> ORGANISM: Mus musculus

<400> SEQUENCE: 34

Met Asn Asn Arg Trp Ile Leu His Ala Ala Phe Leu Leu Cys Phe Ser
1               5                   10                  15

Thr Thr Ala Leu Ser Asn Phe Gly Arg Leu His Cys Thr Thr Ala Val
            20                  25                  30

Ile Arg Asn Ile Asn Asp Gln Val Leu Phe Val Asp Lys Arg Gln Pro
        35                  40                  45

Val Phe Glu Asp Met Thr Asp Ile Asp Gln Ser Ala Ser Glu Pro Gln
    50                  55                  60

Thr Arg Leu Ile Ile Tyr Met Tyr Lys Asp Ser Glu Val Arg Gly Leu
65                  70                  75                  80

Ala Val Thr Leu Ser Val Lys Asp Ser Lys Met Ser Thr Leu Ser Cys
                85                  90                  95

Lys Asn Lys Ile Ile Ser Phe Glu Glu Met Asp Pro Pro Glu Asn Ile
            100                 105                 110

Asp Asp Ile Gln Ser Asp Leu Ile Phe Phe Gln Lys Arg Val Pro Gly
        115                 120                 125

His Asn Lys Met Glu Phe Glu Ser Ser Leu Tyr Glu Gly His Phe Leu
    130                 135                 140

Ala Cys Gln Lys Glu Asp Asp Ala Phe Lys Leu Ile Leu Lys Lys Lys
145                 150                 155                 160

Asp Glu Asn Gly Asp Lys Ser Val Met Phe Thr Leu Thr Asn Leu His
                165                 170                 175

Gln Ser

<210> SEQ ID NO 35
<211> LENGTH: 318
<212> TYPE: PRT
<213> ORGANISM: Artificial Sequence
<220> FEATURE:
<223> OTHER INFORMATION: hCASP1_RV2

<400> SEQUENCE: 35

Met Gly Asn Leu Ser Leu Pro Thr Thr Glu Glu Phe Glu Asp Asp Ala
1               5                   10                  15

Ile Lys Lys Ala His Ile Glu Lys Asp Phe Ile Ala Phe Cys Ser Ser
            20                  25                  30

```
Thr Pro Asp Asn Val Ser Trp Arg His Pro Thr Met Gly Ser Val Phe
            35                  40                  45

Ile Gly Arg Leu Ile Glu His Met Gln Glu Tyr Ala Cys Ser Cys Asp
     50                  55                  60

Val Glu Glu Ile Phe Arg Lys Val Arg Phe Ser Phe Glu Gln Pro Asp
65                  70                  75                  80

Gly Arg Ala Gln Met Pro Thr Thr Glu Arg Val Thr Leu Thr Arg Cys
                85                  90                  95

Phe Tyr Leu Phe Pro Gly His Ala Tyr Val His Asp Ala Pro Val Arg
            100                 105                 110

Asp Gln Thr Ser Gly Asn Tyr Leu Asn Met Gln Asp Ser Gln Gly Val
            115                 120                 125

Leu Ser Ser Phe Pro Ala Pro Gln Ala Val Gln Asp Asn Pro Ala Met
            130                 135                 140

Pro Thr Ser Ser Gly Ser Glu Gly Asn Val Lys Leu Cys Ser Leu Glu
145                 150                 155                 160

Glu Ala Gln Arg Ile Trp Lys Gln Lys Ser Ala Glu Ile Tyr Pro Ile
                165                 170                 175

Met Asp Lys Ser Ser Arg Thr Arg Leu Ala Leu Ile Ile Cys Asn Glu
            180                 185                 190

Glu Phe Asp Ser Ile Pro Arg Arg Thr Gly Ala Glu Val Asp Ile Thr
            195                 200                 205

Gly Met Thr Met Leu Leu Gln Asn Leu Gly Tyr Ser Val Asp Val Lys
            210                 215                 220

Lys Asn Leu Thr Ala Ser Asp Met Thr Thr Glu Leu Glu Ala Phe Ala
225                 230                 235                 240

His Arg Pro Glu His Lys Thr Ser Asp Ser Thr Phe Leu Val Phe Met
                245                 250                 255

Ser His Gly Ile Arg Glu Gly Ile Cys Gly Lys Lys His Ser Glu Gln
            260                 265                 270

Val Pro Asp Ile Leu Gln Leu Asn Ala Ile Phe Asn Met Leu Asn Thr
            275                 280                 285

Lys Asn Cys Pro Ser Leu Lys Asp Lys Pro Lys Val Ile Ile Ile Gln
            290                 295                 300

Ala Cys Arg Gly Asp Ser Pro Gly Val Val Trp Phe Lys Asp
305                 310                 315

<210> SEQ ID NO 36
<211> LENGTH: 174
<212> TYPE: PRT
<213> ORGANISM: Homo sapiens

<400> SEQUENCE: 36

Met Thr Asn Lys Cys Leu Leu Gln Ile Ala Leu Leu Leu Cys Phe Ser
1               5                   10                  15

Thr Thr Ala Leu Ser Ala Pro Val Arg Ser Leu Asn Cys Thr Leu Arg
            20                  25                  30

Asp Ser Gln Gln Lys Ser Leu Val Met Ser Gly Pro Tyr Glu Leu Lys
            35                  40                  45

Ala Leu His Leu Gln Gly Gln Asp Met Glu Gln Gln Val Val Phe Ser
            50                  55                  60

Met Ser Phe Val Gln Gly Glu Glu Ser Asn Asp Lys Ile Pro Val Ala
65                  70                  75                  80

Leu Gly Leu Lys Glu Lys Asn Leu Tyr Leu Ser Cys Val Leu Lys Asp
```

```
                    85                  90                  95

Asp Lys Pro Thr Leu Gln Leu Glu Ser Val Asp Pro Lys Asn Tyr Pro
            100                 105                 110

Lys Lys Lys Met Glu Lys Arg Phe Val Phe Asn Lys Ile Glu Ile Asn
            115                 120                 125

Asn Lys Leu Glu Phe Glu Ser Ala Gln Phe Pro Asn Trp Tyr Ile Ser
        130                 135                 140

Thr Ser Gln Ala Glu Asn Met Pro Val Phe Leu Gly Gly Thr Lys Gly
145                 150                 155                 160

Gly Gln Asp Ile Thr Asp Phe Thr Met Gln Phe Val Ser Ser
                    165                 170

<210> SEQ ID NO 37
<211> LENGTH: 269
<212> TYPE: PRT
<213> ORGANISM: Homo sapiens

<400> SEQUENCE: 37

Met Ala Glu Val Pro Lys Leu Ala Ser Glu Met Met Ala Tyr Tyr Ser
1               5                   10                  15

Gly Asn Glu Asp Asp Leu Phe Phe Glu Ala Asp Gly Pro Lys Gln Met
            20                  25                  30

Lys Cys Ser Phe Gln Asp Leu Asp Leu Cys Pro Leu Asp Gly Gly Ile
        35                  40                  45

Gln Leu Arg Ile Ser Asp His His Tyr Ser Lys Gly Phe Arg Gln Ala
    50                  55                  60

Ala Ser Val Val Val Ala Met Asp Lys Leu Arg Lys Met Leu Val Pro
65                  70                  75                  80

Cys Pro Gln Thr Phe Gln Glu Asn Asp Leu Ser Thr Phe Phe Pro Phe
                85                  90                  95

Ile Phe Glu Glu Glu Pro Ile Phe Phe Asp Thr Trp Asp Asn Glu Ala
            100                 105                 110

Tyr Val His Asp Ala Pro Val Arg Ser Leu Asn Cys Thr Leu Arg Asp
        115                 120                 125

Ser Gln Gln Lys Ser Leu Val Met Ser Gly Pro Tyr Glu Leu Lys Ala
    130                 135                 140

Leu His Leu Gln Gly Gln Asp Met Glu Gln Gln Val Val Phe Ser Met
145                 150                 155                 160

Ser Phe Val Gln Gly Glu Glu Ser Asn Asp Lys Ile Pro Val Ala Leu
                165                 170                 175

Gly Leu Lys Glu Lys Asn Leu Tyr Leu Ser Cys Val Leu Lys Asp Asp
            180                 185                 190

Lys Pro Thr Leu Gln Leu Glu Ser Val Asp Pro Lys Asn Tyr Pro Lys
        195                 200                 205

Lys Lys Met Glu Lys Arg Phe Val Phe Asn Lys Ile Glu Ile Asn Asn
    210                 215                 220

Lys Leu Glu Phe Glu Ser Ala Gln Phe Pro Asn Trp Tyr Ile Ser Thr
225                 230                 235                 240

Ser Gln Ala Glu Asn Met Pro Val Phe Leu Gly Gly Thr Lys Gly Gly
                245                 250                 255

Gln Asp Ile Thr Asp Phe Thr Met Gln Phe Val Ser Ser
            260                 265

<210> SEQ ID NO 38
<211> LENGTH: 303
```

<212> TYPE: PRT
<213> ORGANISM: Artificial Sequence
<220> FEATURE:
<223> OTHER INFORMATION: CASP1_RV2_NTR

<400> SEQUENCE: 38

Met Gly Ile Lys Lys Ala His Ile Glu Lys Asp Phe Ile Ala Phe Cys
1               5                   10                  15

Ser Ser Thr Pro Asp Asn Val Ser Trp Arg His Pro Val Arg Gly Ser
            20                  25                  30

Leu Phe Ile Glu Ser Leu Ile Lys His Met Lys Glu Tyr Ala Trp Ser
        35                  40                  45

Cys Asp Leu Glu Asp Ile Phe Arg Lys Val Arg Phe Ser Phe Glu Gln
    50                  55                  60

Pro Glu Phe Arg Leu Gln Met Pro Thr Ala Asp Arg Val Thr Leu Thr
65                  70                  75                  80

Lys Arg Phe Tyr Leu Phe Pro Gly His Leu Leu Val Cys Asp Val Pro
                85                  90                  95

Ile Arg Ala Pro Ser Ala Glu Thr Phe Val Ala Thr Glu Asp Ser Lys
            100                 105                 110

Gly Gly His Pro Ser Ser Glu Thr Lys Glu Gln Asn Lys Glu
        115                 120                 125

Asp Gly Thr Phe Pro Gly Leu Thr Gly Thr Leu Lys Phe Cys Pro Leu
    130                 135                 140

Glu Lys Ala Gln Lys Leu Trp Lys Glu Asn Pro Ser Glu Ile Tyr Pro
145                 150                 155                 160

Ile Met Asn Thr Thr Thr Arg Thr Arg Leu Ala Leu Ile Ile Cys Asn
                165                 170                 175

Thr Glu Phe Gln His Leu Ser Pro Arg Val Gly Ala Gln Val Asp Leu
            180                 185                 190

Arg Glu Met Lys Leu Leu Leu Glu Asp Leu Gly Tyr Thr Val Lys Val
        195                 200                 205

Lys Glu Asn Leu Thr Ala Leu Glu Met Val Lys Glu Val Lys Glu Phe
210                 215                 220

Ala Ala Cys Pro Glu His Lys Thr Ser Asp Ser Thr Phe Leu Val Phe
225                 230                 235                 240

Met Ser His Gly Ile Gln Glu Gly Ile Cys Gly Thr Thr Tyr Ser Asn
                245                 250                 255

Glu Val Ser Asp Ile Leu Lys Val Asp Thr Ile Phe Gln Met Met Asn
            260                 265                 270

Thr Leu Lys Cys Pro Ser Leu Lys Asp Lys Pro Lys Val Ile Ile Ile
        275                 280                 285

Gln Ala Cys Arg Gly Glu Lys Gln Gly Val Val Leu Leu Lys Asp
    290                 295                 300

<210> SEQ ID NO 39
<211> LENGTH: 317
<212> TYPE: PRT
<213> ORGANISM: Artificial Sequence
<220> FEATURE:
<223> OTHER INFORMATION: CASP1_RV2_C305G

<400> SEQUENCE: 39

Met Ser Glu Glu Asp Phe Leu Thr Asp Ala Ile Phe Glu Asp Asp Gly
1               5                   10                  15

Ile Lys Lys Ala His Ile Glu Lys Asp Phe Ile Ala Phe Cys Ser Ser
            20                  25                  30

```
Thr Pro Asp Asn Val Ser Trp Arg His Pro Val Arg Gly Ser Leu Phe
         35                  40                  45

Ile Glu Ser Leu Ile Lys His Met Lys Glu Tyr Ala Trp Ser Cys Asp
 50                  55                  60

Leu Glu Asp Ile Phe Arg Lys Val Arg Phe Ser Phe Glu Gln Pro Glu
 65                  70                  75                  80

Phe Arg Leu Gln Met Pro Thr Ala Asp Arg Val Thr Leu Thr Lys Arg
                 85                  90                  95

Phe Tyr Leu Phe Pro Gly His Leu Leu Val Cys Asp Val Pro Ile Arg
                100                 105                 110

Ala Pro Ser Ala Glu Thr Phe Val Ala Thr Glu Asp Ser Lys Gly Gly
                115                 120                 125

His Pro Ser Ser Ser Glu Thr Lys Glu Glu Gln Asn Lys Glu Asp Gly
                130                 135                 140

Thr Phe Pro Gly Leu Thr Gly Thr Leu Lys Phe Cys Pro Leu Glu Lys
145                 150                 155                 160

Ala Gln Lys Leu Trp Lys Glu Asn Pro Ser Glu Ile Tyr Pro Ile Met
                165                 170                 175

Asn Thr Thr Thr Arg Thr Arg Leu Ala Leu Ile Ile Cys Asn Thr Glu
                180                 185                 190

Phe Gln His Leu Ser Pro Arg Val Gly Ala Gln Val Asp Leu Arg Glu
                195                 200                 205

Met Lys Leu Leu Leu Glu Asp Leu Gly Tyr Thr Val Lys Val Lys Glu
                210                 215                 220

Asn Leu Thr Ala Leu Glu Met Val Lys Glu Val Lys Glu Phe Ala Ala
225                 230                 235                 240

Cys Pro Glu His Lys Thr Ser Asp Ser Thr Phe Leu Val Phe Met Ser
                245                 250                 255

His Gly Ile Gln Glu Gly Ile Cys Gly Thr Thr Tyr Ser Asn Glu Val
                260                 265                 270

Ser Asp Ile Leu Lys Val Asp Thr Ile Phe Gln Met Met Asn Thr Leu
                275                 280                 285

Lys Cys Pro Ser Leu Lys Asp Lys Pro Lys Val Ile Ile Ile Gln Ala
                290                 295                 300

Gly Arg Gly Glu Lys Gln Gly Val Val Leu Leu Lys Asp
305                 310                 315

<210> SEQ ID NO 40
<211> LENGTH: 317
<212> TYPE: PRT
<213> ORGANISM: Artificial Sequence
<220> FEATURE:
<223> OTHER INFORMATION: CASP1_RV2_D108A

<400> SEQUENCE: 40

Met Ser Glu Glu Asp Phe Leu Thr Asp Ala Ile Phe Glu Asp Asp Gly
 1               5                  10                  15

Ile Lys Lys Ala His Ile Glu Lys Asp Phe Ile Ala Phe Cys Ser Ser
                 20                  25                  30

Thr Pro Asp Asn Val Ser Trp Arg His Pro Val Arg Gly Ser Leu Phe
                 35                  40                  45

Ile Glu Ser Leu Ile Lys His Met Lys Glu Tyr Ala Trp Ser Cys Asp
 50                  55                  60

Leu Glu Asp Ile Phe Arg Lys Val Arg Phe Ser Phe Glu Gln Pro Glu
 65                  70                  75                  80
```

Phe Arg Leu Gln Met Pro Thr Ala Asp Arg Val Thr Leu Thr Lys Arg
                85                  90                  95

Phe Tyr Leu Phe Pro Gly His Leu Leu Val Cys Ala Val Pro Ile Arg
            100                 105                 110

Ala Pro Ser Ala Glu Thr Phe Val Ala Thr Glu Asp Ser Lys Gly Gly
        115                 120                 125

His Pro Ser Ser Ser Glu Thr Lys Glu Glu Gln Asn Lys Glu Asp Gly
    130                 135                 140

Thr Phe Pro Gly Leu Thr Gly Thr Leu Lys Phe Cys Pro Leu Glu Lys
145                 150                 155                 160

Ala Gln Lys Leu Trp Lys Glu Asn Pro Ser Glu Ile Tyr Pro Ile Met
                165                 170                 175

Asn Thr Thr Thr Arg Thr Arg Leu Ala Leu Ile Ile Cys Asn Thr Glu
            180                 185                 190

Phe Gln His Leu Ser Pro Arg Val Gly Ala Gln Val Asp Leu Arg Glu
        195                 200                 205

Met Lys Leu Leu Leu Glu Asp Leu Gly Tyr Thr Val Lys Val Lys Glu
    210                 215                 220

Asn Leu Thr Ala Leu Glu Met Val Lys Glu Val Lys Glu Phe Ala Ala
225                 230                 235                 240

Cys Pro Glu His Lys Thr Ser Asp Ser Thr Phe Leu Val Phe Met Ser
                245                 250                 255

His Gly Ile Gln Glu Gly Ile Cys Gly Thr Thr Tyr Ser Asn Glu Val
            260                 265                 270

Ser Asp Ile Leu Lys Val Asp Thr Ile Phe Gln Met Met Asn Thr Leu
        275                 280                 285

Lys Cys Pro Ser Leu Lys Asp Lys Pro Lys Val Ile Ile Ile Gln Ala
    290                 295                 300

Cys Arg Gly Glu Lys Gln Gly Val Val Leu Leu Lys Asp
305                 310                 315

<210> SEQ ID NO 41
<211> LENGTH: 317
<212> TYPE: PRT
<213> ORGANISM: Artificial Sequence
<220> FEATURE:
<223> OTHER INFORMATION: CASP1_RV2_D124A

<400> SEQUENCE: 41

Met Ser Glu Glu Asp Phe Leu Thr Asp Ala Ile Phe Glu Asp Asp Gly
1               5                   10                  15

Ile Lys Lys Ala His Ile Glu Lys Asp Phe Ile Ala Phe Cys Ser Ser
            20                  25                  30

Thr Pro Asp Asn Val Ser Trp Arg His Pro Val Arg Gly Ser Leu Phe
        35                  40                  45

Ile Glu Ser Leu Ile Lys His Met Lys Glu Tyr Ala Trp Ser Cys Asp
    50                  55                  60

Leu Glu Asp Ile Phe Arg Lys Val Arg Phe Ser Glu Gln Pro Glu
65                  70                  75                  80

Phe Arg Leu Gln Met Pro Thr Ala Asp Arg Val Thr Leu Thr Lys Arg
                85                  90                  95

Phe Tyr Leu Phe Pro Gly His Leu Leu Val Cys Asp Val Pro Ile Arg
            100                 105                 110

Ala Pro Ser Ala Glu Thr Phe Val Ala Thr Glu Ala Ser Lys Gly Gly
        115                 120                 125

His Pro Ser Ser Glu Thr Lys Glu Glu Gln Asn Lys Glu Asp Gly
            130                 135                 140

Thr Phe Pro Gly Leu Thr Gly Thr Leu Lys Phe Cys Pro Leu Glu Lys
145                 150                 155                 160

Ala Gln Lys Leu Trp Lys Glu Asn Pro Ser Glu Ile Tyr Pro Ile Met
                165                 170                 175

Asn Thr Thr Thr Arg Thr Arg Leu Ala Leu Ile Ile Cys Asn Thr Glu
                180                 185                 190

Phe Gln His Leu Ser Pro Arg Val Gly Ala Gln Val Asp Leu Arg Glu
                195                 200                 205

Met Lys Leu Leu Leu Glu Asp Leu Gly Tyr Thr Val Lys Val Lys Glu
        210                 215                 220

Asn Leu Thr Ala Leu Glu Met Val Lys Glu Val Lys Glu Phe Ala Ala
225                 230                 235                 240

Cys Pro Glu His Lys Thr Ser Asp Ser Thr Phe Leu Val Phe Met Ser
                245                 250                 255

His Gly Ile Gln Glu Gly Ile Cys Gly Thr Thr Tyr Ser Asn Glu Val
                260                 265                 270

Ser Asp Ile Leu Lys Val Asp Thr Ile Phe Gln Met Met Asn Thr Leu
                275                 280                 285

Lys Cys Pro Ser Leu Lys Asp Lys Pro Lys Val Ile Ile Ile Gln Ala
        290                 295                 300

Cys Arg Gly Glu Lys Gln Gly Val Val Leu Leu Lys Asp
305                 310                 315

<210> SEQ ID NO 42
<211> LENGTH: 317
<212> TYPE: PRT
<213> ORGANISM: Artificial Sequence
<220> FEATURE:
<223> OTHER INFORMATION: CASP1_RV2_D143A

<400> SEQUENCE: 42

Met Ser Glu Glu Asp Phe Leu Thr Asp Ala Ile Phe Glu Asp Asp Gly
1               5                   10                  15

Ile Lys Lys Ala His Ile Glu Lys Asp Phe Ile Ala Phe Cys Ser Ser
                20                  25                  30

Thr Pro Asp Asn Val Ser Trp Arg His Pro Val Arg Gly Ser Leu Phe
            35                  40                  45

Ile Glu Ser Leu Ile Lys His Met Lys Glu Tyr Ala Trp Ser Cys Asp
    50                  55                  60

Leu Glu Asp Ile Phe Arg Lys Val Arg Phe Ser Phe Glu Gln Pro Glu
65                  70                  75                  80

Phe Arg Leu Gln Met Pro Thr Ala Asp Arg Val Thr Leu Thr Lys Arg
                85                  90                  95

Phe Tyr Leu Phe Pro Gly His Leu Leu Val Cys Asp Val Pro Ile Arg
                100                 105                 110

Ala Pro Ser Ala Glu Thr Phe Val Ala Thr Glu Asp Ser Lys Gly Gly
            115                 120                 125

His Pro Ser Ser Ser Glu Thr Lys Glu Glu Gln Asn Lys Glu Ala Gly
            130                 135                 140

Thr Phe Pro Gly Leu Thr Gly Thr Leu Lys Phe Cys Pro Leu Glu Lys
145                 150                 155                 160

Ala Gln Lys Leu Trp Lys Glu Asn Pro Ser Glu Ile Tyr Pro Ile Met
                165                 170                 175

```
Asn Thr Thr Thr Arg Thr Arg Leu Ala Leu Ile Ile Cys Asn Thr Glu
            180                 185                 190

Phe Gln His Leu Ser Pro Arg Val Gly Ala Gln Val Asp Leu Arg Glu
            195                 200                 205

Met Lys Leu Leu Leu Glu Asp Leu Gly Tyr Thr Val Lys Val Lys Glu
            210                 215                 220

Asn Leu Thr Ala Leu Glu Met Val Lys Glu Val Lys Glu Phe Ala Ala
225                 230                 235                 240

Cys Pro Glu His Lys Thr Ser Asp Ser Thr Phe Leu Val Phe Met Ser
                245                 250                 255

His Gly Ile Gln Glu Gly Ile Cys Gly Thr Thr Tyr Ser Asn Glu Val
                260                 265                 270

Ser Asp Ile Leu Lys Val Asp Thr Ile Phe Gln Met Met Asn Thr Leu
                275                 280                 285

Lys Cys Pro Ser Leu Lys Asp Lys Pro Lys Val Ile Ile Gln Ala
                290                 295                 300

Cys Arg Gly Glu Lys Gln Gly Val Val Leu Leu Lys Asp
305                 310                 315

<210> SEQ ID NO 43
<211> LENGTH: 317
<212> TYPE: PRT
<213> ORGANISM: Artificial Sequence
<220> FEATURE:
<223> OTHER INFORMATION: CASP1_RV2_D108A_D124A_D143A

<400> SEQUENCE: 43

Met Ser Glu Glu Asp Phe Leu Thr Asp Ala Ile Phe Glu Asp Asp Gly
1               5                   10                  15

Ile Lys Lys Ala His Ile Glu Lys Asp Phe Ile Ala Phe Cys Ser Ser
                20                  25                  30

Thr Pro Asp Asn Val Ser Trp Arg His Pro Val Arg Gly Ser Leu Phe
            35                  40                  45

Ile Glu Ser Leu Ile Lys His Met Lys Glu Tyr Ala Trp Ser Cys Asp
50                  55                  60

Leu Glu Asp Ile Phe Arg Lys Val Arg Phe Ser Phe Glu Gln Pro Glu
65                  70                  75                  80

Phe Arg Leu Gln Met Pro Thr Ala Asp Arg Val Thr Leu Thr Lys Arg
                85                  90                  95

Phe Tyr Leu Phe Pro Gly His Leu Leu Val Cys Ala Val Pro Ile Arg
                100                 105                 110

Ala Pro Ser Ala Glu Thr Phe Val Ala Thr Glu Ala Ser Lys Gly Gly
            115                 120                 125

His Pro Ser Ser Ser Glu Thr Lys Glu Glu Gln Asn Lys Glu Ala Gly
            130                 135                 140

Thr Phe Pro Gly Leu Thr Gly Thr Leu Lys Phe Cys Pro Leu Glu Lys
145                 150                 155                 160

Ala Gln Lys Leu Trp Lys Glu Asn Pro Ser Glu Ile Tyr Pro Ile Met
                165                 170                 175

Asn Thr Thr Thr Arg Thr Arg Leu Ala Leu Ile Ile Cys Asn Thr Glu
            180                 185                 190

Phe Gln His Leu Ser Pro Arg Val Gly Ala Gln Val Asp Leu Arg Glu
            195                 200                 205

Met Lys Leu Leu Leu Glu Asp Leu Gly Tyr Thr Val Lys Val Lys Glu
            210                 215                 220
```

Asn Leu Thr Ala Leu Glu Met Val Lys Glu Val Lys Glu Phe Ala Ala
225                 230                 235                 240

Cys Pro Glu His Lys Thr Ser Asp Ser Thr Phe Leu Val Phe Met Ser
            245                 250                 255

His Gly Ile Gln Glu Gly Ile Cys Gly Thr Thr Tyr Ser Asn Glu Val
        260                 265                 270

Ser Asp Ile Leu Lys Val Asp Thr Ile Phe Gln Met Met Asn Thr Leu
            275                 280                 285

Lys Cys Pro Ser Leu Lys Asp Lys Pro Lys Val Ile Ile Gln Ala
        290                 295                 300

Cys Arg Gly Glu Lys Gln Gly Val Val Leu Leu Lys Asp
305                 310                 315

<210> SEQ ID NO 44
<211> LENGTH: 318
<212> TYPE: PRT
<213> ORGANISM: Artificial Sequence
<220> FEATURE:
<223> OTHER INFORMATION: hCASP1_RV2_C306G

<400> SEQUENCE: 44

Met Gly Asn Leu Ser Leu Pro Thr Thr Glu Glu Phe Glu Asp Asp Ala
1               5                   10                  15

Ile Lys Lys Ala His Ile Glu Lys Asp Phe Ile Ala Phe Cys Ser Ser
            20                  25                  30

Thr Pro Asp Asn Val Ser Trp Arg His Pro Thr Met Gly Ser Val Phe
        35                  40                  45

Ile Gly Arg Leu Ile Glu His Met Gln Glu Tyr Ala Cys Ser Cys Asp
    50                  55                  60

Val Glu Glu Ile Phe Arg Lys Val Arg Phe Ser Phe Glu Gln Pro Asp
65                  70                  75                  80

Gly Arg Ala Gln Met Pro Thr Thr Glu Arg Val Thr Leu Thr Arg Cys
                85                  90                  95

Phe Tyr Leu Phe Pro Gly His Ala Tyr Val His Asp Ala Pro Val Arg
            100                 105                 110

Asp Gln Thr Ser Gly Asn Tyr Leu Asn Met Gln Asp Ser Gln Gly Val
        115                 120                 125

Leu Ser Ser Phe Pro Ala Pro Gln Ala Val Gln Asp Asn Pro Ala Met
    130                 135                 140

Pro Thr Ser Ser Gly Ser Glu Gly Asn Val Lys Leu Cys Ser Leu Glu
145                 150                 155                 160

Glu Ala Gln Arg Ile Trp Lys Gln Lys Ser Ala Glu Ile Tyr Pro Ile
                165                 170                 175

Met Asp Lys Ser Ser Arg Thr Arg Leu Ala Leu Ile Ile Cys Asn Glu
            180                 185                 190

Glu Phe Asp Ser Ile Pro Arg Arg Thr Gly Ala Glu Val Asp Ile Thr
        195                 200                 205

Gly Met Thr Met Leu Leu Gln Asn Leu Gly Tyr Ser Val Asp Val Lys
    210                 215                 220

Lys Asn Leu Thr Ala Ser Asp Met Thr Thr Glu Leu Glu Ala Phe Ala
225                 230                 235                 240

His Arg Pro Glu His Lys Thr Ser Asp Ser Thr Phe Leu Val Phe Met
                245                 250                 255

Ser His Gly Ile Arg Glu Gly Ile Cys Gly Lys Lys His Ser Glu Gln
            260                 265                 270

```
Val Pro Asp Ile Leu Gln Leu Asn Ala Ile Phe Asn Met Leu Asn Thr
        275                 280                 285

Lys Asn Cys Pro Ser Leu Lys Asp Lys Pro Lys Val Ile Ile Ile Gln
        290                 295                 300

Ala Gly Arg Gly Asp Ser Pro Gly Val Val Trp Phe Lys Asp
305                 310                 315
```

<210> SEQ ID NO 45
<211> LENGTH: 318
<212> TYPE: PRT
<213> ORGANISM: Artificial Sequence
<220> FEATURE:
<223> OTHER INFORMATION: hCASP1_RV2_D108A

<400> SEQUENCE: 45

```
Met Gly Asn Leu Ser Leu Pro Thr Thr Glu Glu Phe Glu Asp Asp Ala
1               5                   10                  15

Ile Lys Lys Ala His Ile Glu Lys Asp Phe Ile Ala Phe Cys Ser Ser
            20                  25                  30

Thr Pro Asp Asn Val Ser Trp Arg His Pro Thr Met Gly Ser Val Phe
        35                  40                  45

Ile Gly Arg Leu Ile Glu His Met Gln Glu Tyr Ala Cys Ser Cys Asp
    50                  55                  60

Val Glu Glu Ile Phe Arg Lys Val Arg Phe Ser Phe Glu Gln Pro Asp
65                  70                  75                  80

Gly Arg Ala Gln Met Pro Thr Thr Glu Arg Val Thr Leu Thr Arg Cys
                85                  90                  95

Phe Tyr Leu Phe Pro Gly His Ala Tyr Val His Ala Ala Pro Val Arg
            100                 105                 110

Asp Gln Thr Ser Gly Asn Tyr Leu Asn Met Gln Asp Ser Gln Gly Val
        115                 120                 125

Leu Ser Ser Phe Pro Ala Pro Gln Ala Val Gln Asp Asn Pro Ala Met
    130                 135                 140

Pro Thr Ser Ser Gly Ser Glu Gly Asn Val Lys Leu Cys Ser Leu Glu
145                 150                 155                 160

Glu Ala Gln Arg Ile Trp Lys Gln Lys Ser Ala Glu Ile Tyr Pro Ile
                165                 170                 175

Met Asp Lys Ser Ser Arg Thr Arg Leu Ala Leu Ile Ile Cys Asn Glu
            180                 185                 190

Glu Phe Asp Ser Ile Pro Arg Arg Thr Gly Ala Glu Val Asp Ile Thr
        195                 200                 205

Gly Met Thr Met Leu Leu Gln Asn Leu Gly Tyr Ser Val Asp Val Lys
    210                 215                 220

Lys Asn Leu Thr Ala Ser Asp Met Thr Thr Glu Leu Glu Ala Phe Ala
225                 230                 235                 240

His Arg Pro Glu His Lys Thr Ser Asp Ser Thr Phe Leu Val Phe Met
                245                 250                 255

Ser His Gly Ile Arg Glu Gly Ile Cys Gly Lys Lys His Ser Glu Gln
            260                 265                 270

Val Pro Asp Ile Leu Gln Leu Asn Ala Ile Phe Asn Met Leu Asn Thr
        275                 280                 285

Lys Asn Cys Pro Ser Leu Lys Asp Lys Pro Lys Val Ile Ile Ile Gln
    290                 295                 300

Ala Cys Arg Gly Asp Ser Pro Gly Val Val Trp Phe Lys Asp
305                 310                 315
```

<210> SEQ ID NO 46
<211> LENGTH: 318
<212> TYPE: PRT
<213> ORGANISM: Artificial Sequence
<220> FEATURE:
<223> OTHER INFORMATION: hCASP1_RV2_D140A

<400> SEQUENCE: 46

```
Met Gly Asn Leu Ser Leu Pro Thr Thr Glu Glu Phe Glu Asp Asp Ala
1               5                   10                  15

Ile Lys Lys Ala His Ile Glu Lys Asp Phe Ile Ala Phe Cys Ser Ser
            20                  25                  30

Thr Pro Asp Asn Val Ser Trp Arg His Pro Thr Met Gly Ser Val Phe
        35                  40                  45

Ile Gly Arg Leu Ile Glu His Met Gln Glu Tyr Ala Cys Ser Cys Asp
    50                  55                  60

Val Glu Glu Ile Phe Arg Lys Val Arg Phe Ser Phe Glu Gln Pro Asp
65                  70                  75                  80

Gly Arg Ala Gln Met Pro Thr Thr Glu Arg Val Thr Leu Thr Arg Cys
                85                  90                  95

Phe Tyr Leu Phe Pro Gly His Ala Tyr Val His Asp Ala Pro Val Arg
            100                 105                 110

Asp Gln Thr Ser Gly Asn Tyr Leu Asn Met Gln Asp Ser Gln Gly Val
        115                 120                 125

Leu Ser Ser Phe Pro Ala Pro Gln Ala Val Gln Ala Asn Pro Ala Met
130                 135                 140

Pro Thr Ser Ser Gly Ser Glu Gly Asn Val Lys Leu Cys Ser Leu Glu
145                 150                 155                 160

Glu Ala Gln Arg Ile Trp Lys Gln Lys Ser Ala Glu Ile Tyr Pro Ile
                165                 170                 175

Met Asp Lys Ser Ser Arg Thr Arg Leu Ala Leu Ile Ile Cys Asn Glu
            180                 185                 190

Glu Phe Asp Ser Ile Pro Arg Arg Thr Gly Ala Glu Val Asp Ile Thr
        195                 200                 205

Gly Met Thr Met Leu Leu Gln Asn Leu Gly Tyr Ser Val Asp Val Lys
    210                 215                 220

Lys Asn Leu Thr Ala Ser Asp Met Thr Thr Glu Leu Glu Ala Phe Ala
225                 230                 235                 240

His Arg Pro Glu His Lys Thr Ser Asp Ser Thr Phe Leu Val Phe Met
                245                 250                 255

Ser His Gly Ile Arg Glu Gly Ile Cys Gly Lys Lys His Ser Glu Gln
            260                 265                 270

Val Pro Asp Ile Leu Gln Leu Asn Ala Ile Phe Asn Met Leu Asn Thr
        275                 280                 285

Lys Asn Cys Pro Ser Leu Lys Asp Lys Pro Lys Val Ile Ile Ile Gln
    290                 295                 300

Ala Cys Arg Gly Asp Ser Pro Gly Val Val Trp Phe Lys Asp
305                 310                 315
```

<210> SEQ ID NO 47
<211> LENGTH: 318
<212> TYPE: PRT
<213> ORGANISM: Artificial Sequence
<220> FEATURE:
<223> OTHER INFORMATION: hCASP1_RV2_D124A -continued

```
<400> SEQUENCE: 47

Met Gly Asn Leu Ser Leu Pro Thr Thr Glu Glu Phe Glu Asp Asp Ala
1               5                   10                  15

Ile Lys Lys Ala His Ile Glu Lys Asp Phe Ile Ala Phe Cys Ser Ser
            20                  25                  30

Thr Pro Asp Asn Val Ser Trp Arg His Pro Thr Met Gly Ser Val Phe
        35                  40                  45

Ile Gly Arg Leu Ile Glu His Met Gln Glu Tyr Ala Cys Ser Cys Asp
    50                  55                  60

Val Glu Glu Ile Phe Arg Lys Val Arg Phe Ser Phe Glu Gln Pro Asp
65                  70                  75                  80

Gly Arg Ala Gln Met Pro Thr Thr Glu Arg Val Thr Leu Thr Arg Cys
                85                  90                  95

Phe Tyr Leu Phe Pro Gly His Ala Tyr Val His Asp Ala Pro Val Arg
            100                 105                 110

Asp Gln Thr Ser Gly Asn Tyr Leu Asn Met Gln Ala Ser Gln Gly Val
        115                 120                 125

Leu Ser Ser Phe Pro Ala Pro Gln Ala Val Gln Asp Asn Pro Ala Met
    130                 135                 140

Pro Thr Ser Ser Gly Ser Glu Gly Asn Val Lys Leu Cys Ser Leu Glu
145                 150                 155                 160

Glu Ala Gln Arg Ile Trp Lys Gln Lys Ser Ala Glu Ile Tyr Pro Ile
                165                 170                 175

Met Asp Lys Ser Ser Arg Thr Arg Leu Ala Leu Ile Ile Cys Asn Glu
            180                 185                 190

Glu Phe Asp Ser Ile Pro Arg Arg Thr Gly Ala Glu Val Asp Ile Thr
        195                 200                 205

Gly Met Thr Met Leu Leu Gln Asn Leu Gly Tyr Ser Val Asp Val Lys
    210                 215                 220

Lys Asn Leu Thr Ala Ser Asp Met Thr Thr Glu Leu Glu Ala Phe Ala
225                 230                 235                 240

His Arg Pro Glu His Lys Thr Ser Asp Ser Thr Phe Leu Val Phe Met
                245                 250                 255

Ser His Gly Ile Arg Glu Gly Ile Cys Gly Lys Lys His Ser Glu Gln
            260                 265                 270

Val Pro Asp Ile Leu Gln Leu Asn Ala Ile Phe Asn Met Leu Asn Thr
        275                 280                 285

Lys Asn Cys Pro Ser Leu Lys Asp Lys Pro Lys Val Ile Ile Ile Gln
    290                 295                 300

Ala Cys Arg Gly Asp Ser Pro Gly Val Val Trp Phe Lys Asp
305                 310                 315

<210> SEQ ID NO 48
<211> LENGTH: 310
<212> TYPE: PRT
<213> ORGANISM: Artificial Sequence
<220> FEATURE:
<223> OTHER INFORMATION: hCASP1_RV2_NTR2

<400> SEQUENCE: 48

Met Glu Glu Phe Glu Asp Asp Ala Ile Lys Lys Ala His Ile Glu Lys
1               5                   10                  15

Asp Phe Ile Ala Phe Cys Ser Ser Thr Pro Asp Asn Val Ser Trp Arg
            20                  25                  30

His Pro Thr Met Gly Ser Val Phe Ile Gly Arg Leu Ile Glu His Met
```

```
                35                  40                  45
Gln Glu Tyr Ala Cys Ser Cys Asp Val Glu Ile Phe Arg Lys Val
 50                  55                  60
Arg Phe Ser Phe Glu Gln Pro Asp Gly Arg Ala Gln Met Pro Thr Thr
 65                  70                  75                  80
Glu Arg Val Thr Leu Thr Arg Cys Phe Tyr Leu Phe Pro Gly His Ala
                 85                  90                  95
Tyr Val His Asp Ala Pro Val Arg Asp Gln Thr Ser Gly Asn Tyr Leu
                100                 105                 110
Asn Met Gln Asp Ser Gln Gly Val Leu Ser Ser Phe Pro Ala Pro Gln
                115                 120                 125
Ala Val Gln Asp Asn Pro Ala Met Pro Thr Ser Ser Gly Ser Glu Gly
                130                 135                 140
Asn Val Lys Leu Cys Ser Leu Glu Glu Ala Gln Arg Ile Trp Lys Gln
145                 150                 155                 160
Lys Ser Ala Glu Ile Tyr Pro Ile Met Asp Lys Ser Ser Arg Thr Arg
                165                 170                 175
Leu Ala Leu Ile Ile Cys Asn Glu Glu Phe Asp Ser Ile Pro Arg Arg
                180                 185                 190
Thr Gly Ala Glu Val Asp Ile Thr Gly Met Thr Met Leu Leu Gln Asn
                195                 200                 205
Leu Gly Tyr Ser Val Asp Val Lys Lys Asn Leu Thr Ala Ser Asp Met
                210                 215                 220
Thr Thr Glu Leu Glu Ala Phe Ala His Arg Pro Glu His Lys Thr Ser
225                 230                 235                 240
Asp Ser Thr Phe Leu Val Phe Met Ser His Gly Ile Arg Glu Gly Ile
                245                 250                 255
Cys Gly Lys Lys His Ser Glu Gln Val Pro Asp Ile Leu Gln Leu Asn
                260                 265                 270
Ala Ile Phe Asn Met Leu Asn Thr Lys Asn Cys Pro Ser Leu Lys Asp
                275                 280                 285
Lys Pro Lys Val Ile Ile Gln Ala Cys Arg Gly Asp Ser Pro Gly
                290                 295                 300
Val Val Trp Phe Lys Asp
305                 310

<210> SEQ ID NO 49
<211> LENGTH: 304
<212> TYPE: PRT
<213> ORGANISM: Artificial Sequence
<220> FEATURE:
<223> OTHER INFORMATION: hCASP1_RV2_NTR

<400> SEQUENCE: 49

Met Ala Ile Lys Lys Ala His Ile Glu Lys Asp Phe Ile Ala Phe Cys
  1               5                  10                  15
Ser Ser Thr Pro Asp Asn Val Ser Trp Arg His Pro Thr Met Gly Ser
                 20                  25                  30
Val Phe Ile Gly Arg Leu Ile Glu His Met Gln Glu Tyr Ala Cys Ser
                 35                  40                  45
Cys Asp Val Glu Glu Ile Phe Arg Lys Val Arg Phe Ser Phe Glu Gln
                 50                  55                  60
Pro Asp Gly Arg Ala Gln Met Pro Thr Thr Glu Arg Val Thr Leu Thr
 65                  70                  75                  80
Arg Cys Phe Tyr Leu Phe Pro Gly His Ala Tyr Val His Asp Ala Pro
```

```
              85                  90                  95
Val Arg Asp Gln Thr Ser Gly Asn Tyr Leu Asn Met Gln Asp Ser Gln
                100                 105                 110

Gly Val Leu Ser Ser Phe Pro Ala Pro Gln Ala Val Gln Asp Asn Pro
            115                 120                 125

Ala Met Pro Thr Ser Ser Gly Ser Glu Gly Asn Val Lys Leu Cys Ser
        130                 135                 140

Leu Glu Glu Ala Gln Arg Ile Trp Lys Gln Lys Ser Ala Glu Ile Tyr
145                 150                 155                 160

Pro Ile Met Asp Lys Ser Ser Arg Thr Arg Leu Ala Leu Ile Ile Cys
                165                 170                 175

Asn Glu Glu Phe Asp Ser Ile Pro Arg Arg Thr Gly Ala Glu Val Asp
                180                 185                 190

Ile Thr Gly Met Thr Met Leu Leu Gln Asn Leu Gly Tyr Ser Val Asp
                195                 200                 205

Val Lys Lys Asn Leu Thr Ala Ser Asp Met Thr Thr Glu Leu Glu Ala
            210                 215                 220

Phe Ala His Arg Pro Glu His Lys Thr Ser Asp Ser Thr Phe Leu Val
225                 230                 235                 240

Phe Met Ser His Gly Ile Arg Glu Gly Ile Cys Gly Lys Lys His Ser
                245                 250                 255

Glu Gln Val Pro Asp Ile Leu Gln Leu Asn Ala Ile Phe Asn Met Leu
                260                 265                 270

Asn Thr Lys Asn Cys Pro Ser Leu Lys Asp Lys Pro Lys Val Ile Ile
                275                 280                 285

Ile Gln Ala Cys Arg Gly Asp Ser Pro Gly Val Val Trp Phe Lys Asp
            290                 295                 300

<210> SEQ ID NO 50
<211> LENGTH: 276
<212> TYPE: PRT
<213> ORGANISM: Artificial Sequence
<220> FEATURE:
<223> OTHER INFORMATION: hCASP1_RV2_NTR_GSL

<400> SEQUENCE: 50

Met Ala Ile Lys Lys Ala His Ile Glu Lys Asp Phe Ile Ala Phe Cys
1               5                   10                  15

Ser Ser Thr Pro Asp Asn Val Ser Trp Arg His Pro Thr Met Gly Ser
                20                  25                  30

Val Phe Ile Gly Arg Leu Ile Glu His Met Gln Glu Tyr Ala Cys Ser
            35                  40                  45

Cys Asp Val Glu Glu Ile Phe Arg Lys Val Arg Phe Ser Phe Glu Gln
        50                  55                  60

Pro Asp Gly Arg Ala Gln Met Pro Thr Thr Glu Arg Val Thr Leu Thr
65                  70                  75                  80

Arg Cys Phe Tyr Leu Phe Pro Gly His Gly Ser Gly Ser Gly Ser Gly
                85                  90                  95

Ser Gly Asn Pro Ala Met Pro Thr Ser Ser Gly Ser Glu Gly Asn Val
                100                 105                 110

Lys Leu Cys Ser Leu Glu Glu Ala Gln Arg Ile Trp Lys Gln Lys Ser
            115                 120                 125

Ala Glu Ile Tyr Pro Ile Met Asp Lys Ser Ser Arg Thr Arg Leu Ala
        130                 135                 140

Leu Ile Ile Cys Asn Glu Glu Phe Asp Ser Ile Pro Arg Arg Thr Gly
```

```
                145                 150                 155                 160
Ala Glu Val Asp Ile Thr Gly Met Thr Met Leu Leu Gln Asn Leu Gly
                    165                 170                 175

Tyr Ser Val Asp Val Lys Lys Asn Leu Thr Ala Ser Asp Met Thr Thr
                    180                 185                 190

Glu Leu Glu Ala Phe Ala His Arg Pro Glu His Lys Thr Ser Asp Ser
                    195                 200                 205

Thr Phe Leu Val Phe Met Ser His Gly Ile Arg Glu Gly Ile Cys Gly
            210                 215                 220

Lys Lys His Ser Glu Gln Val Pro Asp Ile Leu Gln Leu Asn Ala Ile
225                 230                 235                 240

Phe Asn Met Leu Asn Thr Lys Asn Cys Pro Ser Leu Lys Asp Lys Pro
                245                 250                 255

Lys Val Ile Ile Ile Gln Ala Cys Arg Gly Asp Ser Pro Gly Val Val
                260                 265                 270

Trp Phe Lys Asp
        275

<210> SEQ ID NO 51
<211> LENGTH: 276
<212> TYPE: PRT
<213> ORGANISM: Artificial Sequence
<220> FEATURE:
<223> OTHER INFORMATION: hCASP1_RV2_NTR_CCS

<400> SEQUENCE: 51

Met Ala Ile Lys Lys Ala His Ile Glu Lys Asp Phe Ile Ala Phe Cys
1               5                   10                  15

Ser Ser Thr Pro Asp Asn Val Ser Trp Arg His Pro Thr Met Gly Ser
                20                  25                  30

Val Phe Ile Gly Arg Leu Ile Glu His Met Gln Glu Tyr Ala Cys Ser
            35                  40                  45

Cys Asp Val Glu Glu Ile Phe Arg Lys Val Arg Phe Ser Phe Glu Gln
        50                  55                  60

Pro Asp Gly Arg Ala Gln Met Pro Thr Thr Glu Arg Val Thr Leu Thr
65                  70                  75                  80

Arg Cys Phe Tyr Leu Phe Pro Gly His Ala Tyr Val His Asp Ala Pro
                85                  90                  95

Val Arg Asn Pro Ala Met Pro Thr Ser Ser Gly Ser Glu Gly Asn Val
                100                 105                 110

Lys Leu Cys Ser Leu Glu Glu Ala Gln Arg Ile Trp Lys Gln Lys Ser
            115                 120                 125

Ala Glu Ile Tyr Pro Ile Met Asp Lys Ser Ser Arg Thr Arg Leu Ala
        130                 135                 140

Leu Ile Ile Cys Asn Glu Glu Phe Asp Ser Ile Pro Arg Arg Thr Gly
145                 150                 155                 160

Ala Glu Val Asp Ile Thr Gly Met Thr Met Leu Leu Gln Asn Leu Gly
                    165                 170                 175

Tyr Ser Val Asp Val Lys Lys Asn Leu Thr Ala Ser Asp Met Thr Thr
                    180                 185                 190

Glu Leu Glu Ala Phe Ala His Arg Pro Glu His Lys Thr Ser Asp Ser
                    195                 200                 205

Thr Phe Leu Val Phe Met Ser His Gly Ile Arg Glu Gly Ile Cys Gly
            210                 215                 220

Lys Lys His Ser Glu Gln Val Pro Asp Ile Leu Gln Leu Asn Ala Ile
```

```
                    225                 230                 235                 240

Phe Asn Met Leu Asn Thr Lys Asn Cys Pro Ser Leu Lys Asp Lys Pro
                        245                 250                 255

Lys Val Ile Ile Ile Gln Ala Cys Arg Gly Asp Ser Pro Gly Val Val
                        260                 265                 270

Trp Phe Lys Asp
                275

<210> SEQ ID NO 52
<211> LENGTH: 404
<212> TYPE: PRT
<213> ORGANISM: Homo sapiens

<400> SEQUENCE: 52

Met Ala Asp Lys Val Leu Lys Glu Lys Arg Lys Leu Phe Ile Arg Ser
        1               5                   10                  15

Met Gly Glu Gly Thr Ile Asn Gly Leu Leu Asp Glu Leu Leu Gln Thr
                        20                  25                  30

Arg Val Leu Asn Lys Glu Glu Met Glu Lys Val Lys Arg Glu Asn Ala
                        35                  40                  45

Thr Val Met Asp Lys Thr Arg Ala Leu Ile Asp Ser Val Ile Pro Lys
                50                  55                  60

Gly Ala Gln Ala Cys Gln Ile Cys Ile Thr Tyr Ile Cys Glu Glu Asp
        65                  70                  75                  80

Ser Tyr Leu Ala Gly Thr Leu Gly Leu Ser Ala Asp Gln Thr Ser Gly
                        85                  90                  95

Asn Tyr Leu Asn Met Gln Asp Ser Gln Gly Val Leu Ser Ser Phe Pro
                        100                 105                 110

Ala Pro Gln Ala Val Gln Asp Asn Pro Ala Met Pro Thr Ser Ser Gly
                        115                 120                 125

Ser Glu Gly Asn Val Lys Leu Cys Ser Leu Glu Glu Ala Gln Arg Ile
                130                 135                 140

Trp Lys Gln Lys Ser Ala Glu Ile Tyr Pro Ile Met Asp Lys Ser Ser
        145                 150                 155                 160

Arg Thr Arg Leu Ala Leu Ile Ile Cys Asn Glu Glu Phe Asp Ser Ile
                        165                 170                 175

Pro Arg Arg Thr Gly Ala Glu Val Asp Ile Thr Gly Met Thr Met Leu
                        180                 185                 190

Leu Gln Asn Leu Gly Tyr Ser Val Asp Val Lys Lys Asn Leu Thr Ala
                        195                 200                 205

Ser Asp Met Thr Thr Glu Leu Glu Ala Phe Ala His Arg Pro Glu His
                210                 215                 220

Lys Thr Ser Asp Ser Thr Phe Leu Val Phe Met Ser His Gly Ile Arg
        225                 230                 235                 240

Glu Gly Ile Cys Gly Lys Lys His Ser Glu Gln Val Pro Asp Ile Leu
                        245                 250                 255

Gln Leu Asn Ala Ile Phe Asn Met Leu Asn Thr Lys Asn Cys Pro Ser
                        260                 265                 270

Leu Lys Asp Lys Pro Lys Val Ile Ile Gln Ala Cys Arg Gly Asp
                        275                 280                 285

Ser Pro Gly Val Val Trp Phe Lys Asp Ser Val Gly Val Ser Gly Asn
                290                 295                 300

Leu Ser Leu Pro Thr Thr Glu Glu Phe Glu Asp Asp Ala Ile Lys Lys
        305                 310                 315                 320
```

```
Ala His Ile Glu Lys Asp Phe Ile Ala Phe Cys Ser Ser Thr Pro Asp
                325                 330                 335

Asn Val Ser Trp Arg His Pro Thr Met Gly Ser Val Phe Ile Gly Arg
            340                 345                 350

Leu Ile Glu His Met Gln Glu Tyr Ala Cys Ser Cys Asp Val Glu Glu
            355                 360                 365

Ile Phe Arg Lys Val Arg Phe Ser Phe Glu Gln Pro Asp Gly Arg Ala
370                 375                 380

Gln Met Pro Thr Thr Glu Arg Val Thr Leu Thr Arg Cys Phe Tyr Leu
385                 390                 395                 400

Phe Pro Gly His
```

<210> SEQ ID NO 53
<211> LENGTH: 492
<212> TYPE: PRT
<213> ORGANISM: Artificial Sequence
<220> FEATURE:
<223> OTHER INFORMATION: hGSDMD_WT_FLAG

<400> SEQUENCE: 53

```
Met Gly Ser Ala Phe Glu Arg Val Val Arg Val Val Gln Glu Leu
1               5                   10                  15

Asp His Gly Gly Glu Phe Ile Pro Val Thr Ser Leu Gln Ser Ser Thr
                20                  25                  30

Gly Phe Gln Pro Tyr Cys Leu Val Arg Lys Pro Ser Ser Ser Trp
            35                  40                  45

Phe Trp Lys Pro Arg Tyr Lys Cys Val Asn Leu Ser Ile Lys Asp Ile
50                  55                  60

Leu Glu Pro Asp Ala Ala Glu Pro Asp Val Gln Arg Gly Arg Ser Phe
65                  70                  75                  80

His Phe Tyr Asp Ala Met Asp Gly Gln Ile Gln Gly Ser Val Glu Leu
                85                  90                  95

Ala Ala Pro Gly Gln Ala Lys Ile Ala Gly Gly Ala Ala Val Ser Asp
            100                 105                 110

Ser Ser Ser Thr Ser Met Asn Val Tyr Ser Leu Ser Val Asp Pro Asn
            115                 120                 125

Thr Trp Gln Thr Leu Leu His Glu Arg His Leu Arg Gln Pro Glu His
130                 135                 140

Lys Val Leu Gln Gln Leu Arg Ser Arg Gly Asp Asn Val Tyr Val Val
145                 150                 155                 160

Thr Glu Val Leu Gln Thr Gln Lys Glu Val Glu Val Thr Arg Thr His
                165                 170                 175

Lys Arg Glu Gly Ser Gly Arg Phe Ser Leu Pro Gly Ala Thr Cys Leu
            180                 185                 190

Gln Gly Glu Gly Gln Gly His Leu Ser Gln Lys Lys Thr Val Thr Ile
            195                 200                 205

Pro Ser Gly Ser Thr Leu Ala Phe Arg Val Ala Gln Leu Val Ile Asp
            210                 215                 220

Ser Asp Leu Asp Val Leu Leu Phe Pro Asp Lys Lys Gln Arg Thr Phe
225                 230                 235                 240

Gln Pro Pro Ala Thr Gly His Lys Arg Ser Thr Ser Glu Gly Ala Trp
                245                 250                 255

Pro Gln Leu Pro Ser Gly Leu Ser Met Met Arg Cys Leu His Asn Phe
            260                 265                 270

Leu Thr Asp Gly Val Pro Ala Glu Gly Ala Phe Thr Glu Asp Phe Gln
```

```
            275                 280                 285
Gly Leu Arg Ala Glu Val Glu Thr Ile Ser Lys Glu Leu Glu Leu Leu
        290                 295                 300
Asp Arg Glu Leu Cys Gln Leu Leu Glu Gly Leu Glu Gly Val Leu
305                 310                 315                 320
Arg Asp Gln Leu Ala Leu Arg Ala Leu Glu Ala Leu Glu Gln Gly
                325                 330                 335
Gln Ser Leu Gly Pro Val Glu Pro Leu Asp Gly Pro Ala Gly Ala Val
            340                 345                 350
Leu Glu Cys Leu Val Leu Ser Ser Gly Met Leu Val Pro Glu Leu Ala
                355                 360                 365
Ile Pro Val Val Tyr Leu Leu Gly Ala Leu Thr Met Leu Ser Glu Thr
        370                 375                 380
Gln His Lys Leu Leu Ala Glu Ala Leu Glu Ser Gln Thr Leu Leu Gly
385                 390                 395                 400
Pro Leu Glu Leu Val Gly Ser Leu Leu Glu Gln Ser Ala Pro Trp Gln
                405                 410                 415
Glu Arg Ser Thr Met Ser Leu Pro Pro Gly Leu Leu Gly Asn Ser Trp
            420                 425                 430
Gly Glu Gly Ala Pro Ala Trp Val Leu Leu Asp Glu Cys Gly Leu Glu
        435                 440                 445
Leu Gly Glu Asp Thr Pro His Val Cys Trp Glu Pro Gln Ala Gln Gly
450                 455                 460
Arg Met Cys Ala Leu Tyr Ala Ser Leu Ala Leu Leu Ser Gly Leu Ser
465                 470                 475                 480
Gln Glu Pro His Asp Tyr Lys Asp Asp Asp Lys
                485                 490

<210> SEQ ID NO 54
<211> LENGTH: 92
<212> TYPE: PRT
<213> ORGANISM: Artificial Sequence
<220> FEATURE:
<223> OTHER INFORMATION: hCASP1_CARD

<400> SEQUENCE: 54

Met Ala Asp Lys Val Leu Lys Glu Lys Arg Lys Leu Phe Ile Arg Ser
1               5                   10                  15
Met Gly Glu Gly Thr Ile Asn Gly Leu Leu Asp Glu Leu Leu Gln Thr
            20                  25                  30
Arg Val Leu Asn Lys Glu Glu Met Glu Lys Val Lys Arg Glu Asn Ala
        35                  40                  45
Thr Val Met Asp Lys Thr Arg Ala Leu Ile Asp Ser Val Ile Pro Lys
    50                  55                  60
Gly Ala Gln Ala Cys Gln Ile Cys Ile Thr Tyr Ile Cys Glu Glu Asp
65                  70                  75                  80
Ser Tyr Leu Ala Gly Thr Leu Gly Leu Ser Ala Asp
                85                  90

<210> SEQ ID NO 55
<211> LENGTH: 27
<212> TYPE: PRT
<213> ORGANISM: Artificial Sequence
<220> FEATURE:
<223> OTHER INFORMATION: hCASP1_CDL

<400> SEQUENCE: 55
```

Gln Thr Ser Gly Asn Tyr Leu Asn Met Gln Asp Ser Gln Gly Val Leu
1               5                   10                  15

Ser Ser Phe Pro Ala Pro Gln Ala Val Gln Asp
            20                  25

<210> SEQ ID NO 56
<211> LENGTH: 178
<212> TYPE: PRT
<213> ORGANISM: Artificial Sequence
<220> FEATURE:
<223> OTHER INFORMATION: hCASP1_p20

<400> SEQUENCE: 56

Asn Pro Ala Met Pro Thr Ser Ser Gly Ser Glu Gly Asn Val Lys Leu
1               5                   10                  15

Cys Ser Leu Glu Glu Ala Gln Arg Ile Trp Lys Gln Lys Ser Ala Glu
            20                  25                  30

Ile Tyr Pro Ile Met Asp Lys Ser Ser Arg Thr Arg Leu Ala Leu Ile
            35                  40                  45

Ile Cys Asn Glu Glu Phe Asp Ser Ile Pro Arg Arg Thr Gly Ala Glu
        50                  55                  60

Val Asp Ile Thr Gly Met Thr Met Leu Leu Gln Asn Leu Gly Tyr Ser
65                  70                  75                  80

Val Asp Val Lys Lys Asn Leu Thr Ala Ser Asp Met Thr Thr Glu Leu
                85                  90                  95

Glu Ala Phe Ala His Arg Pro Glu His Lys Thr Ser Asp Ser Thr Phe
            100                 105                 110

Leu Val Phe Met Ser His Gly Ile Arg Glu Gly Ile Cys Gly Lys Lys
        115                 120                 125

His Ser Glu Gln Val Pro Asp Ile Leu Gln Leu Asn Ala Ile Phe Asn
    130                 135                 140

Met Leu Asn Thr Lys Asn Cys Pro Ser Leu Lys Asp Lys Pro Lys Val
145                 150                 155                 160

Ile Ile Ile Gln Ala Cys Arg Gly Asp Ser Pro Gly Val Val Trp Phe
                165                 170                 175

Lys Asp

<210> SEQ ID NO 57
<211> LENGTH: 19
<212> TYPE: PRT
<213> ORGANISM: Artificial Sequence
<220> FEATURE:
<223> OTHER INFORMATION: hCASP1_IDL

<400> SEQUENCE: 57

Ser Val Gly Val Ser Gly Asn Leu Ser Leu Pro Thr Thr Glu Glu Phe
1               5                   10                  15

Glu Asp Asp

<210> SEQ ID NO 58
<211> LENGTH: 88
<212> TYPE: PRT
<213> ORGANISM: Artificial Sequence
<220> FEATURE:
<223> OTHER INFORMATION: hCASP1_p10

<400> SEQUENCE: 58

Ala Ile Lys Lys Ala His Ile Glu Lys Asp Phe Ile Ala Phe Cys Ser
1               5                   10                  15

```
Ser Thr Pro Asp Asn Val Ser Trp Arg His Pro Thr Met Gly Ser Val
            20                  25                  30

Phe Ile Gly Arg Leu Ile Glu His Met Gln Tyr Ala Cys Ser Cys
            35                  40                  45

Asp Val Glu Glu Ile Phe Arg Lys Val Arg Phe Ser Phe Glu Gln Pro
 50                  55                  60

Asp Gly Arg Ala Gln Met Pro Thr Thr Glu Arg Val Thr Leu Thr Arg
 65                  70                  75                  80

Cys Phe Tyr Leu Phe Pro Gly His
                    85

<210> SEQ ID NO 59
<211> LENGTH: 17
<212> TYPE: PRT
<213> ORGANISM: Artificial Sequence
<220> FEATURE:
<223> OTHER INFORMATION: binding sequence

<400> SEQUENCE: 59

Gly Gly Val Ala Asp Leu Ile Lys Lys Phe Glu Ser Ile Ser Lys Glu
 1               5                  10                  15

Glu

<210> SEQ ID NO 60
<211> LENGTH: 14
<212> TYPE: PRT
<213> ORGANISM: Artificial Sequence
<220> FEATURE:
<223> OTHER INFORMATION: IDL sequence

<400> SEQUENCE: 60

Ser Glu Glu Asp Phe Leu Thr Asp Ala Ile Phe Glu Asp Asp
 1               5                  10

<210> SEQ ID NO 61
<211> LENGTH: 14
<212> TYPE: PRT
<213> ORGANISM: Artificial Sequence
<220> FEATURE:
<223> OTHER INFORMATION: inter-domain linker

<400> SEQUENCE: 61

Gly Asn Leu Ser Leu Pro Thr Thr Glu Glu Phe Glu Asp Asp
 1               5                  10

<210> SEQ ID NO 62
<211> LENGTH: 15
<212> TYPE: PRT
<213> ORGANISM: Artificial Sequence
<220> FEATURE:
<223> OTHER INFORMATION: linker

<400> SEQUENCE: 62

Gly Gly Gly Gly Ser Gly Gly Gly Ser Gly Gly Gly Gly Ser
 1               5                  10                  15

<210> SEQ ID NO 63
<211> LENGTH: 35
<212> TYPE: PRT
<213> ORGANISM: Artificial Sequence
<220> FEATURE:
<223> OTHER INFORMATION: linker

<400> SEQUENCE: 63
```

```
Gly Gly Gly Gly Ser Gly Gly Gly Ser Gly Gly Gly Ser Gly
1               5                   10                  15
Gly Gly Gly Ser Gly Gly Gly Ser Gly Gly Gly Ser Gly Gly
            20                  25                  30
Gly Gly Ser
        35
```

<210> SEQ ID NO 64
<211> LENGTH: 15
<212> TYPE: PRT
<213> ORGANISM: Artificial Sequence
<220> FEATURE:
<223> OTHER INFORMATION: linker

<400> SEQUENCE: 64

```
Gly Gly Gly Ser Ser Gly Gly Gly Ser Ser Gly Gly Gly Ser Ser
1               5                   10                  15
```

<210> SEQ ID NO 65
<211> LENGTH: 8
<212> TYPE: PRT
<213> ORGANISM: Gallus gallus

<400> SEQUENCE: 65

```
Ser Ile Ile Asn Phe Glu Lys Leu
1               5
```

<210> SEQ ID NO 66
<211> LENGTH: 9
<212> TYPE: PRT
<213> ORGANISM: Artificial Sequence
<220> FEATURE:
<223> OTHER INFORMATION: aa

<400> SEQUENCE: 66

```
Ala Tyr Val His Asp Ala Pro Val Arg
1               5
```

<210> SEQ ID NO 67
<211> LENGTH: 9
<212> TYPE: PRT
<213> ORGANISM: Artificial Sequence
<220> FEATURE:
<223> OTHER INFORMATION: linker

<400> SEQUENCE: 67

```
Gly Ser Gly Ser Gly Ser Gly Ser Gly
1               5
```

<210> SEQ ID NO 68
<211> LENGTH: 60
<212> TYPE: PRT
<213> ORGANISM: Homo sapiens

<400> SEQUENCE: 68

```
Phe Pro Ala Pro Gln Ala Val Gln Asp Asn Pro Ala Met Pro Thr Ser
1               5                   10                  15
Ser Gly Ser Glu Gly Asn Val Lys Leu Cys Ser Leu Glu Glu Ala Gln
            20                  25                  30
Arg Ile Trp Lys Gln Lys Ser Ala Glu Ile Tyr Pro Ile Met Asp Lys
        35                  40                  45
Ser Ser Arg Thr Arg Leu Ala Leu Ile Ile Cys Asn
    50                  55                  60
```

<210> SEQ ID NO 69
<211> LENGTH: 59
<212> TYPE: PRT
<213> ORGANISM: Mus musculus

<400> SEQUENCE: 69

Ser Ser Glu Thr Lys Glu Glu Gln Asn Lys Glu Asp Gly Thr Phe Pro
1               5                   10                  15

Gly Leu Thr Gly Thr Leu Lys Phe Cys Pro Leu Glu Lys Ala Gln Lys
            20                  25                  30

Leu Trp Lys Glu Asn Pro Ser Glu Ile Tyr Pro Ile Met Asn Thr Thr
        35                  40                  45

Thr Arg Thr Arg Leu Ala Leu Ile Ile Cys Asn
    50                  55

<210> SEQ ID NO 70
<211> LENGTH: 60
<212> TYPE: PRT
<213> ORGANISM: Homo sapiens

<400> SEQUENCE: 70

Pro Asn Lys Lys Ala His Pro Asn Met Glu Ala Gly Pro Pro Glu Ser
1               5                   10                  15

Gly Glu Ser Thr Asp Ala Leu Lys Leu Cys Pro His Glu Glu Phe Leu
            20                  25                  30

Arg Leu Cys Lys Glu Arg Ala Glu Glu Ile Tyr Pro Ile Lys Glu Arg
        35                  40                  45

Asn Asn Arg Thr Arg Leu Ala Leu Ile Ile Cys Asn
    50                  55                  60

<210> SEQ ID NO 71
<211> LENGTH: 56
<212> TYPE: PRT
<213> ORGANISM: Mus musculus

<400> SEQUENCE: 71

His His Gly Glu Ala Asn Leu Glu Met Glu Glu Pro Glu Ser Leu
1               5                   10                  15

Asn Thr Leu Lys Leu Cys Ser Pro Glu Glu Phe Thr Arg Leu Cys Arg
            20                  25                  30

Glu Lys Thr Gln Glu Ile Tyr Pro Ile Lys Glu Ala Asn Gly Arg Thr
        35                  40                  45

Arg Lys Ala Leu Ile Ile Cys Asn
    50                  55

<210> SEQ ID NO 72
<211> LENGTH: 60
<212> TYPE: PRT
<213> ORGANISM: Homo sapiens

<400> SEQUENCE: 72

Thr Ser Val Lys Pro Leu Leu Gln Ile Glu Ala Gly Pro Pro Glu Ser
1               5                   10                  15

Ala Glu Ser Thr Asn Ile Leu Lys Leu Cys Pro Arg Gly Glu Phe Leu
            20                  25                  30

Arg Leu Cys Lys Lys Asn His Asp Glu Ile Tyr Pro Ile Lys Lys Arg
        35                  40                  45

Glu Asp Arg Arg Arg Leu Ala Leu Ile Ile Cys Asn
    50                  55                  60

<210> SEQ ID NO 73
<211> LENGTH: 60
<212> TYPE: PRT
<213> ORGANISM: Mus musculus

<400> SEQUENCE: 73

Ala His Glu Ser His Leu Met Leu Thr Ala Pro His Gly Leu Gln Ser
1               5                   10                  15

Ser Glu Val Gln Asp Thr Leu Lys Leu Cys Pro Arg Asp Gln Phe Cys
            20                  25                  30

Lys Ile Lys Thr Glu Arg Ala Lys Glu Ile Tyr Pro Val Met Glu Lys
        35                  40                  45

Glu Gly Arg Thr Arg Leu Ala Leu Ile Ile Cys Asn
    50                  55                  60

<210> SEQ ID NO 74
<211> LENGTH: 57
<212> TYPE: PRT
<213> ORGANISM: Homo sapiens

<400> SEQUENCE: 74

Val Phe Ile Gly Arg Leu Ile Glu His Met Gln Glu Tyr Ala Cys Ser
1               5                   10                  15

Cys Asp Val Glu Glu Ile Phe Arg Lys Val Arg Phe Ser Phe Glu Gln
            20                  25                  30

Pro Asp Gly Arg Ala Gln Met Pro Thr Thr Glu Arg Val Thr Leu Thr
        35                  40                  45

Arg Cys Phe Tyr Leu Phe Pro Gly His
    50                  55

<210> SEQ ID NO 75
<211> LENGTH: 57
<212> TYPE: PRT
<213> ORGANISM: Mus musculus

<400> SEQUENCE: 75

Leu Phe Ile Glu Ser Leu Ile Lys His Met Lys Glu Tyr Ala Trp Ser
1               5                   10                  15

Cys Asp Leu Glu Asp Ile Phe Arg Lys Val Arg Phe Ser Phe Glu Gln
            20                  25                  30

Pro Glu Phe Arg Leu Gln Met Pro Thr Ala Asp Arg Val Thr Leu Thr
        35                  40                  45

Lys Arg Phe Tyr Leu Phe Pro Gly His
    50                  55

<210> SEQ ID NO 76
<211> LENGTH: 57
<212> TYPE: PRT
<213> ORGANISM: Homo sapiens

<400> SEQUENCE: 76

Ile Phe Ile Thr Gln Leu Ile Thr Cys Phe Gln Lys Tyr Ser Trp Cys
1               5                   10                  15

Cys His Leu Glu Glu Val Phe Arg Lys Val Gln Gln Ser Phe Glu Thr
            20                  25                  30

Pro Arg Ala Lys Ala Gln Met Pro Thr Ile Glu Arg Leu Ser Met Thr
        35                  40                  45

Arg Tyr Phe Tyr Leu Phe Pro Gly Asn

```
                50                  55

<210> SEQ ID NO 77
<211> LENGTH: 57
<212> TYPE: PRT
<213> ORGANISM: Mus musculus

<400> SEQUENCE: 77

Tyr Phe Ile Thr Arg Leu Ile Ser Cys Phe Arg Lys His Ala Cys Ser
1               5                   10                  15

Cys His Leu Phe Asp Ile Phe Leu Lys Val Gln Gln Ser Phe Glu Lys
            20                  25                  30

Ala Ser Ile His Ser Gln Met Pro Thr Ile Asp Arg Ala Thr Leu Thr
        35                  40                  45

Arg Tyr Phe Tyr Leu Phe Pro Gly Asn
    50                  55

<210> SEQ ID NO 78
<211> LENGTH: 57
<212> TYPE: PRT
<213> ORGANISM: Homo sapiens

<400> SEQUENCE: 78

Ile Phe Ile Thr Glu Leu Ile Thr Cys Phe Gln Lys Tyr Ser Cys Cys
1               5                   10                  15

Cys His Leu Met Glu Ile Phe Arg Lys Val Gln Lys Ser Phe Glu Val
            20                  25                  30

Pro Gln Ala Lys Ala Gln Met Pro Thr Ile Glu Arg Ala Thr Leu Thr
        35                  40                  45

Arg Asp Phe Tyr Leu Phe Pro Gly Asn
    50                  55

<210> SEQ ID NO 79
<211> LENGTH: 57
<212> TYPE: PRT
<213> ORGANISM: Mus musculus

<400> SEQUENCE: 79

Leu Phe Ile Ser Lys Leu Ile Asp Cys Phe Lys Lys Tyr Cys Trp Cys
1               5                   10                  15

Tyr His Leu Glu Glu Ile Phe Arg Lys Val Gln His Ser Phe Glu Val
            20                  25                  30

Pro Gly Glu Leu Thr Gln Met Pro Thr Ile Glu Arg Val Ser Met Thr
        35                  40                  45

Arg Tyr Phe Tyr Leu Phe Pro Gly Asn
    50                  55

<210> SEQ ID NO 80
<211> LENGTH: 14
<212> TYPE: PRT
<213> ORGANISM: Artificial Sequence
<220> FEATURE:
<223> OTHER INFORMATION: CASP1_RV2

<400> SEQUENCE: 80

Gly Asn Leu Ser Leu Pro Thr Thr Glu Glu Phe Glu Asp Asp
1               5                   10

<210> SEQ ID NO 81
<211> LENGTH: 19
<212> TYPE: PRT
```

```
<213> ORGANISM: Artificial Sequence
<220> FEATURE:
<223> OTHER INFORMATION: CASP1_RV2

<400> SEQUENCE: 81

Ser Val Gly Val Ser Gly Asn Leu Ser Leu Pro Thr Thr Glu Glu Phe
1               5                   10                  15

Glu Asp Asp

<210> SEQ ID NO 82
<211> LENGTH: 14
<212> TYPE: PRT
<213> ORGANISM: Artificial Sequence
<220> FEATURE:
<223> OTHER INFORMATION: CASP1_RV2

<400> SEQUENCE: 82

Ser Glu Glu Asp Phe Leu Thr Asp Ala Ile Phe Glu Asp Asp
1               5                   10
```

IMMUNE-STIMULATORY COMPOSITIONS AND USE THEREOF

CLAIM OF PRIORITY

This application is a national phase application under 35 U.S.C. 371 of International Patent Application No. PCT/NL2020/050225, filed Apr. 2, 2020, titled "IMMUNE-STIMULATORY COMPOSITIONS AND USE THEREOF," now International Publication No. WO/2020/204714.

SEQUENCE LISTING

The instant application contains a Sequence Listing which has been filed electronically in ASCII format and is hereby incorporated by reference in its entirety. Said ASCII copy, created on Jan. 16, 2024 is named 14834-702.US0_ST25.txt and is 130,947 bytes in size.

FIELD

The invention relates generally to immune stimulatory compositions comprising an inducer of pyroptotic cell death such as a constitutively active pro-inflammatory caspase, comprising swapped p10 and p20 domains.

1. INTRODUCTION

Effective immune responses against cancer and pathogens require the activation of T cells specific for protein fragments (antigens) selectively expressed by malignantly transformed or infected cells. Upon activation in draining lymph nodes, these activated T cells re-enter the circulation and invade the affected tissues to clear aberrant—but not healthy—cells. After this first encounter with antigen, an expanded subset of these T cells persists and is more easily activated. These memory T cells thus reduce the susceptibility to re-infection with the same or a similar pathogen and may similarly reduce a risk of cancer recurrence. Antigen specificity and memory are both features characteristic of the adaptive immune system.

To prevent infections, individuals can be immunised by administration of antigen preparations, either derived from the infectious pathogen itself or produced synthetically in the form of peptide, protein, mRNA or DNA. This procedure, otherwise known as vaccination, may also be applicable to the prevention and treatment of cancer. Innate immune system activation is an absolute requirement for the induction of adaptive immune responses. Critical to vaccine efficacy, particularly in the case of synthetic vaccines, is therefore the inclusion of an adjuvant that activates cells of the innate immune system (McKee and Marrack, 2017. Curr Opin Immunol 47: 44-51).

The most commonly used adjuvant is alum, which is composed of aluminum salts. More recently developed adjuvants tend to mimic pathogen-associated molecular patterns (PAMPS) to target pattern recognition receptors (PRR) on innate immune cells (Kanzler et al., 2007. Nat Med 13: 552-9; Wu, 2016. Immunology 148: 315-25; Vasou et al., 2017. Viruses 9: pii: E186). These adjuvants generally work well with protein and peptide vaccines, but not with genetic vaccines consisting of RNA or DNA (Li and Petrovsky, 2016. Expert Rev Vaccines 15: 313-29).

While the first vaccine derived from an infectious pathogen was made in the 18th century, genetic vaccines are much younger. The first DNA vaccines were developed towards the end of the 20th century, and the first report on mRNA vaccines dates from 2004 (Carralot et al., 2004. Cell Mol Life Sci 61: 2418-24). Although many genetic vaccines are currently in clinical trials, none have yet been approved for human use. A major challenge in this field is the discovery of effective adjuvants. Such adjuvants are usually combined with the mRNA or DNA and encode immune stimulatory proteins such as cytokines, chemokines, and more recently components of PRR signaling pathways. Of these adjuvants, only two have thus far shown promise in human clinical trials: cytokines IL-12 and GM-CSF (CSF2) (Li et al., 2017. Clin Vaccine Immunol 24: e00263-17; Richie et al., 2012. Hum Vaccin Immunother 8: 1564-84).

There is thus a need to provide efficient inducers of innate immune responses that can be used as adjuvants for genetic vaccines, i.e. nucleic acid-based vaccines.

2. BRIEF DESCRIPTION OF THE INVENTION

The invention provides a constitutively active pro-inflammatory caspase for use in a method of stimulating an immune response in an individual, preferably a T-cell mediated immune response, comprising administering said constitutively active pro-inflammatory caspase to the individual.

Infected or transformed cells can alert the immune system by the way they die. Apoptosis tends to be immunologically silent, as apoptotic cells do not emit inflammatory signals and are swiftly cleared by macrophages. In contrast, cells undergoing inflammatory cell death induce immune activation. Pyroptosis and necroptosis are recently discovered forms of programmed necrosis that lead to the release of damage-associated molecular patterns (DAMPS; Wallach et al., 2016. Science 352: 51-58). These DAMPS include intracellular molecules that perform non-inflammatory functions in living cells (e.g. ATP, high-mobility group box 1 (HMGB1)), and cytokines such as IL-1β, IL-18 and IL-33. Pyroptotic and necroptotic DAMPS require membrane disruption to be released into the extracellular milieu, where they can bind pattern recognition receptors (PRRs) and/or cytokine receptors to activate innate immune cells.

Cells undergoing necroptosis are known to elicit anti-tumour immunity. Injection of necroptotic cells into mice activates IFNγ-, TNF- and IL-2-producing T cells specific for the tumour antigens contained within these cells. These T cells are cytotoxic and can efficiently eliminate tumour cells (Yatim et al., 2015. Science 350: 328-334; Aaes et al., 2016. Cell Rep 15: 274-278). Furthermore, forced expression of a necroptotic effector molecule, mixed lineage kinase domain-like (MLKL) in tumour cells activates tumour-specific T cells that help clear that tumour (van Hoecke et al., 2018. Nat Commun 9: 3417). The importance of necroptosis in anti-tumour immunity is also underscored by the fact that expression of receptor interacting protein kinase 3 (RIPK3), a key player in this pathway just upstream of MLKL, is frequently reduced in tumour cells. Active MLKL forms pores in the cell membrane, upon which the cells 'explode' due to osmosis, leading to abundant DAMP release. Thus, necroptosis can stimulate anti-tumour immunity by triggering a cytotoxic response characterised by the pro-inflammatory cytokines IFNγ and TNF, a type of immune response typically employed for anti-viral immunity.

Pyroptosis on the other hand occurs mainly in macrophages exposed to bacteria such as *Salmonella*, fungi, and some viruses. Specific to pyroptosis are the release of pro-inflammatory cytokines IL18 and IL1β, and the formation of gasdermin D (GSDMD) pores in the cell membrane (Amarante-Mendes et al., 2018. Front Immunol 9: 2379-97).

GSDMD induces a morphologically unique type cell death characterised by the formation of pyroptotic bodies in the absence of osmotically induced cell swelling and bursting (Chen et al., 2016. Cell Res 26:1007-20). Cytokine production and cell death both rely on the activation of pro-inflammatory caspases, most notably caspase-1. This pathway can be detrimental to combating viral infections, as mice lacking caspase-1 are less susceptible to influenza infection (Ren et al., 2017. Sci Rep 7: 7625) and inhibition of caspase-1 prolonged survival of mice after infection with rabies virus (Koraka et al., 2018. Vaccine 10.1016/j.vaccine.2018.04.002). Thus, in contrast with necroptosis, pyroptosis emerges as an anti-microbial response in a limited subset of cells (macrophages), with a different signature cytokine profile (IL18, IL1β) and morphology. It is therefore not obvious to target this pathway for stimulating an immune response against viruses or cancer.

Several documents, including US 2014/037685, US 2018/311343, WO 2018/049014 and WO 2018/106753 have suggested that an inducer of pyroptosis may stimulate an immune response. This inducer of pyroptosis preferably is or encodes a protein selected from an apoptosis-associated speck protein containing a CARD (ASC), an inflammatory caspase such as caspase-1, a gasdermin such as gasdermin-D or gasdermin E, and/or a variant of any one of these proteins. However, none of these documents describes and shows a constitutively active pro-inflammatory caspase generated by domain swapping.

A constitutively active pro-inflammatory caspase according to the invention, preferably human constitutively active pro-inflammatory caspase, comprises swapped p20 and p10 domains, optionally connected by a protease cleavable site. Said constitutively active pro-inflammatory caspase according to the invention preferably is a constitutively active pro-inflammatory caspase-1. Said constitutively active pro-inflammatory caspase according to the invention preferably lacks a caspase-recruitment domain (CARD).

A constitutively active pro-inflammatory caspase, preferably human caspase-1, according to the invention preferably comprises a glycine corresponding to G401 (SEQ ID NO:1), which is located at a distance up to 40 amino acids residues from a cysteine corresponding to C135 (SEQ ID NO:1), preferably at a distance of less than 10 amino acid residues such as 0-2 amino acid residues. A preferred constitutively active pro-inflammatory caspase according to the invention preferably comprise a glycine corresponding to G403 (SEQ ID NO:52), which is located at a distance from 0 to 40 amino acids residues from a cysteine corresponding to C136 (SEQ ID NO:52), preferably at a distance of 0-10 amino acid residues such as 0-2 amino acid residues. This effectively removes or replaces up to 16 N-terminal amino acids of the p20 domain and up to 1 C-terminal amino acid of the p10 domain.

A constitutively active pro-inflammatory caspase according to the invention preferably lacks a p20-p10 interdomain linker (IDL) at the N-terminal part of the protein. Hence, the region N-terminal to the caspase p10 domain, a remnant of the 1DL, is preferably shorter than 15 amino acids, preferably shorter than 7 amino acids, more preferably shorter than 2 amino acids, most preferably absent.

A preferred immune response is directed against a tumour or infection that is present in an individual or is induced to prevent occurrence or recurrence of a tumour or infection in an individual. Administration of said inducer of pyroptosis, preferably said constitutively active pro-inflammatory caspase comprising shuffled p10 and p20 domains, thus is for prophylactic and/or therapeutic administration.

In an embodiment, said inducer of pyroptosis, preferably said constitutively active pro-inflammatory caspase comprising shuffled p10 and p20 domains, is administered into a tumour of the individual, preferably by intra-tumoural injection.

In an embodiment, said inducer of pyroptosis, preferably said constitutively active pro-inflammatory caspase comprising shuffled p10 and p20 domains, is administered topically and/or systemically as an adjuvant of a vaccine.

Said inducer of pyroptosis, preferably said constitutively active pro-inflammatory caspase comprising shuffled p10 and p20 domains, preferably is administered in combination with one or more accessory molecules such as an immune checkpoint inhibitor and/or a further immune stimulating molecule such as a chemokine or a cytokine, preferably one or more accessory molecules as exemplified in Table 3. A preferred accessory molecule is an immune checkpoint inhibitor such as antibodies against PD1 or its ligands, antibodies against CTLA-4, and/or a cytokine such as Interleukin-12 (IL12) and/or granulocyte-macrophage colony-stimulating factor (CSF2).

In an embodiment, said inducer of pyroptosis, preferably said constitutively active pro-inflammatory caspase comprising shuffled p10 and p20 domains, is provided as an expression molecule, preferably expressing an inducer of pyroptosis as listed in any one of Tables 1-2, preferably said constitutively active pro-inflammatory caspase comprising shuffled p10 and p20 domains.

The invention further provides an immune-stimulating composition, comprising an inducer of pyroptosis, preferably said constitutively active pro-inflammatory caspase comprising shuffled p10 and p20 domains, and a pharmacologically acceptable excipient.

Said immune-stimulating composition according to the invention preferably further comprises at least one antigen or antigen-encoding nucleic acid molecule. Said immune-stimulating composition may additionally comprise comprising an accessory immune stimulating molecule such as an immune checkpoint inhibitor and/or a, further immune stimulating molecule such as a cytokine and/or a chemokine. A preferred accessory molecule is or comprises one or more of the molecules provided in Table 3.

Said inducer of pyroptosis, preferably said constitutively active pro-inflammatory caspase comprising shuffled p10 and p20 domains, in an immune-stimulating composition according to the invention preferably is selected from the molecules depicted in any one of Tables 1-2.

The invention further provides an immune-stimulating composition according to the invention, for use in a method of treating an individual suffering from a tumour or an infection.

The invention further provides a method of stimulating an immune response in an individual, preferably a T-cell mediated immune response, comprising providing a composition of the invention and administering said composition to the individual.

3. FIGURE LEGENDS

FIG. 1. Caspase-1 constructs. The CASP1_WT (SEQ ID NO: 1) construct codes for the entire wild-type sequence of *Mus musculus* Casp1, while in CASP1_C285G (SEQ ID NO: 2) the cysteine (at position 284) in the active site of Casp1 is replaced with a Glycine, rendering this site enzymatically inactive. In CASP1_RV (SEQ ID NO: 3) and CASP1_RV2 (SEQ ID NO: 4), the C-terminal p10 domain (SEQ ID NO: 5) is moved to the N-terminus and separated from the CARD-p20 linker sequence (SEQ ID NO: 6) by the Caspase-1 cleavage site of Il1b (SEQ ID NO: 7), which is indicated by a downward arrow. CASP1_RV retains a small part of p20 (5 C-terminal amino acids) at the N-terminus, which has been removed in CASP1_RV2. Finally, in iCASP1 (SEQ ID NO: 8) a CARD-less version of Caspase-1 is connected by a small SGGGS linker (SEQ ID NO: 9) to an AP1903-inducible dimerisation domain from FKBP (F36V-FKBP, SEQ ID NO: 10). F36M-FKBP (SEQ ID NO: 11) in dCASP1 (SEQ ID NO: 12) induces spontaneous dimerisation.

Figure 2:
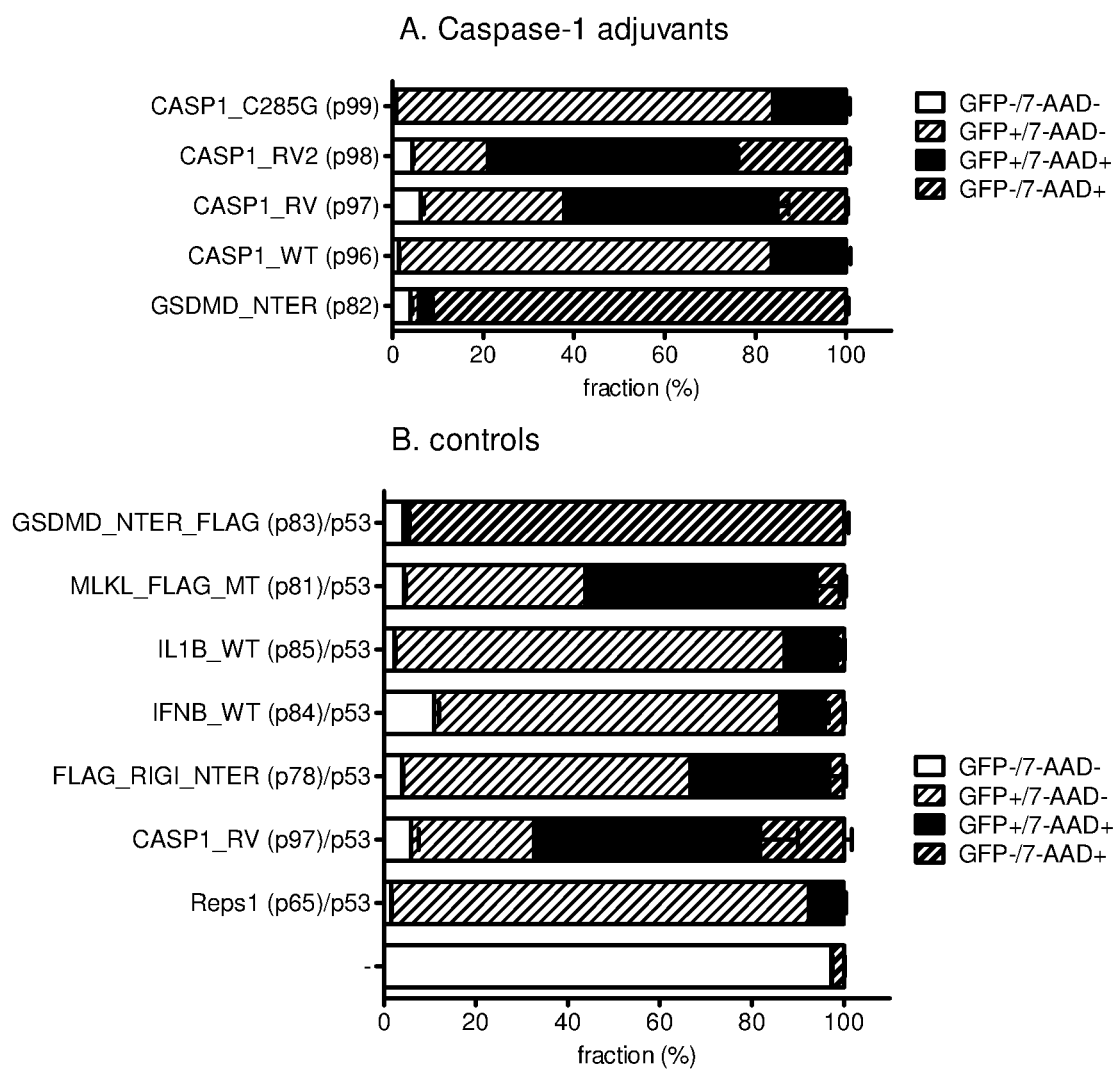

FIG. 2. CASP1_RV and CASP1_RV2 induce cell death. B16F10 cells were transfected with 25 ng of the indicated plasmids (SEQ ID NO: NO 14-20) mixed with 25 ng GFP-plasmid (SEQ ID NO: 13, labeled p53). Two days after transfection, cells were harvested and stained with 7-AAD, a marker of dead cells. (A) Caspase-1 constructs. (B) control constructs. An expression vector coding for a non-relevant small peptide Reps1 (SEQ ID NO: 20) served as negative control, and GSDMD_NTER (SEQ ID NO: 14) as a positive control. Note that a construct representing the N-terminus of DExD/H-Box Helicase 58 (Ddx58; FLAG_RIGI_NTER, SEQ ID NO: 19) also induces cell death.

Figure 3:
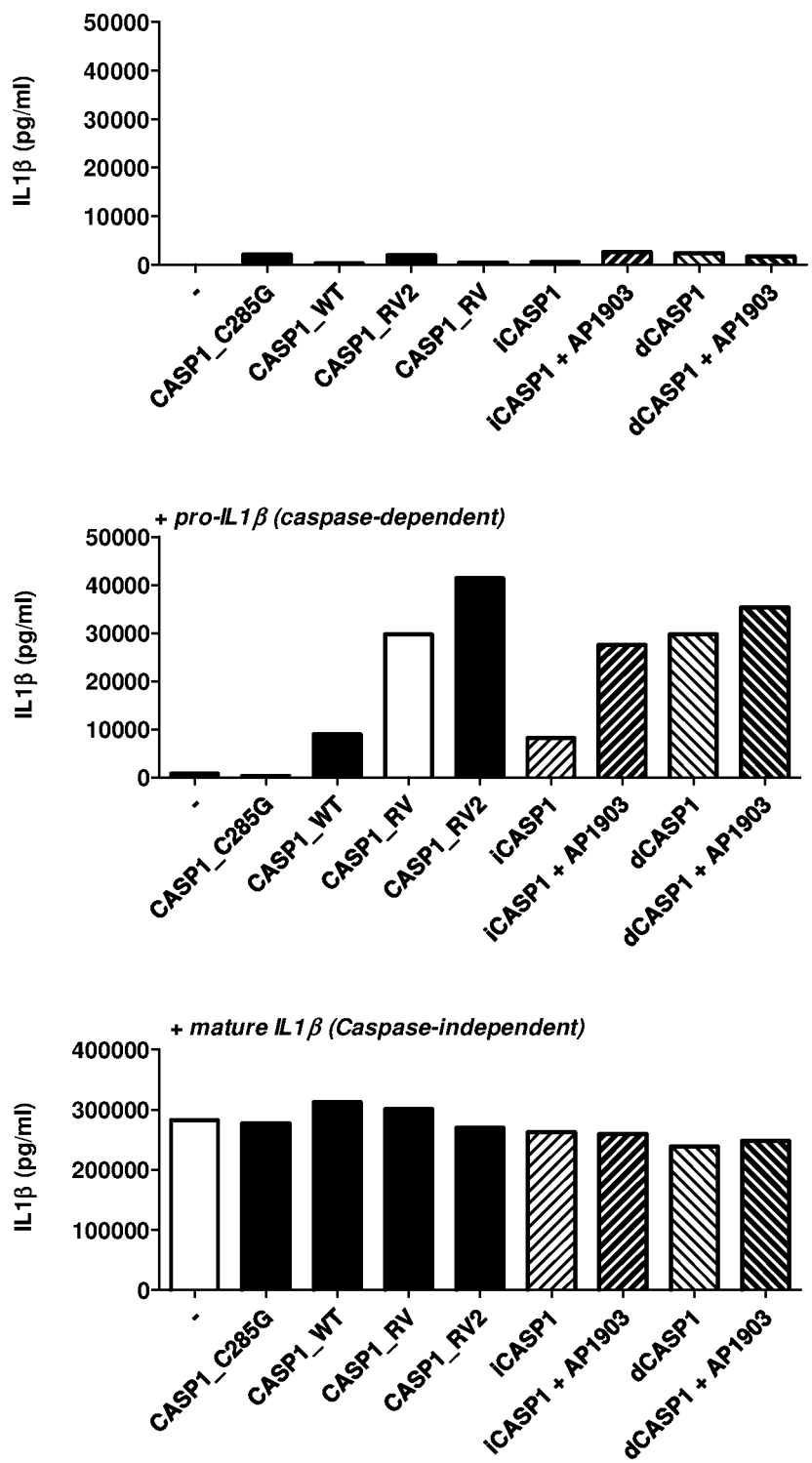

FIG. 3. CASP1_RV2 induces pro-IL-1β processing and IL-1β secretion. B16F10 cells were transfected with 0.6 ng of the indicated plasmids mixed with 10 ng empty vector, pro-IL1β (SEQ ID NO: 21, IL1B_FL, caspase-1 dependent), or mature IL-1β (SEQ ID NO: 22, IL1B_WT, caspase-1 independent). When indicated, cells were treated with 10 nM AP1903 one day after transfection. Two days after transfection, supernatants were harvested for IL-1β ELISA and measurement of LDH release. Note that under these experimental conditions, none of the transfections resulted in cell death, as they did not cause significant LDH release (data not shown).

Figure 4:
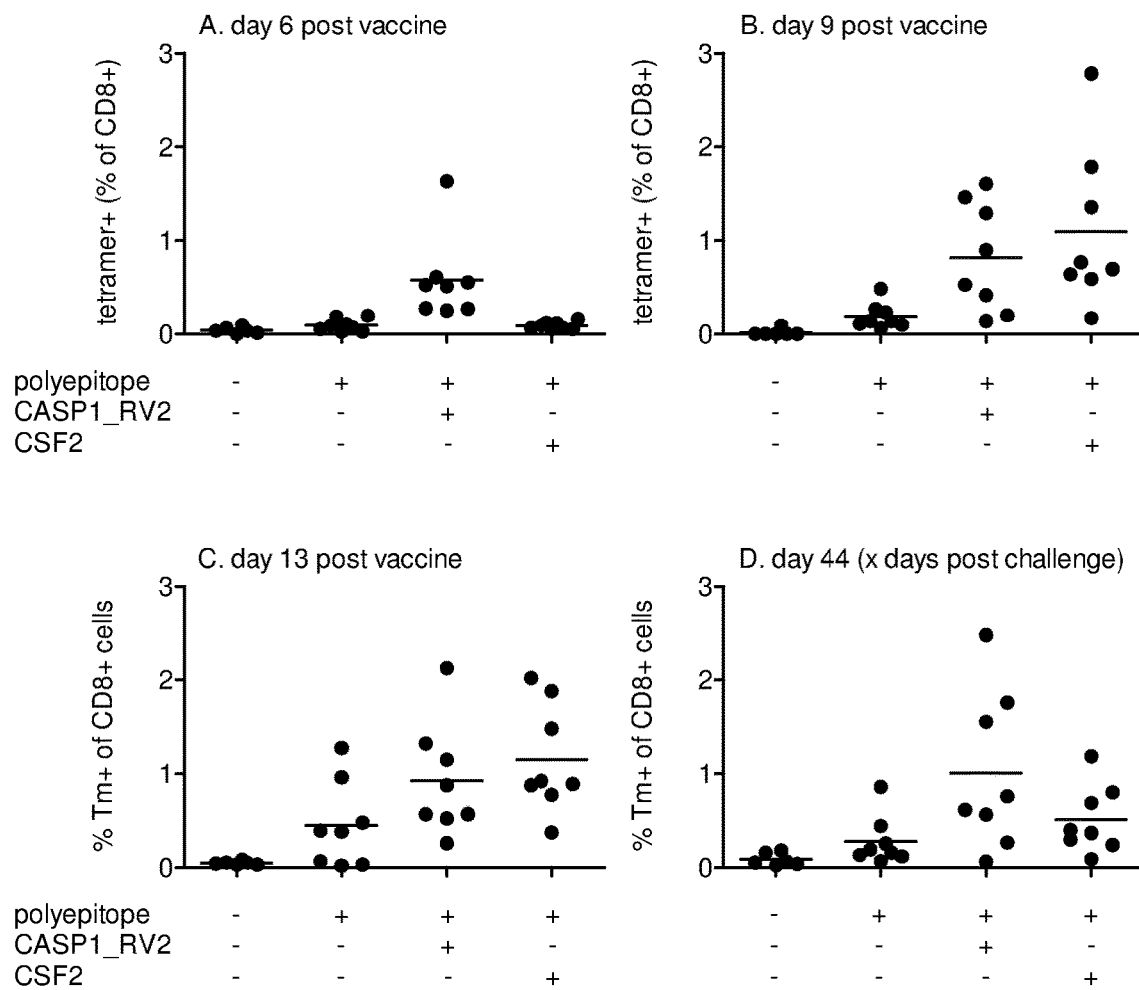
Figure 4:
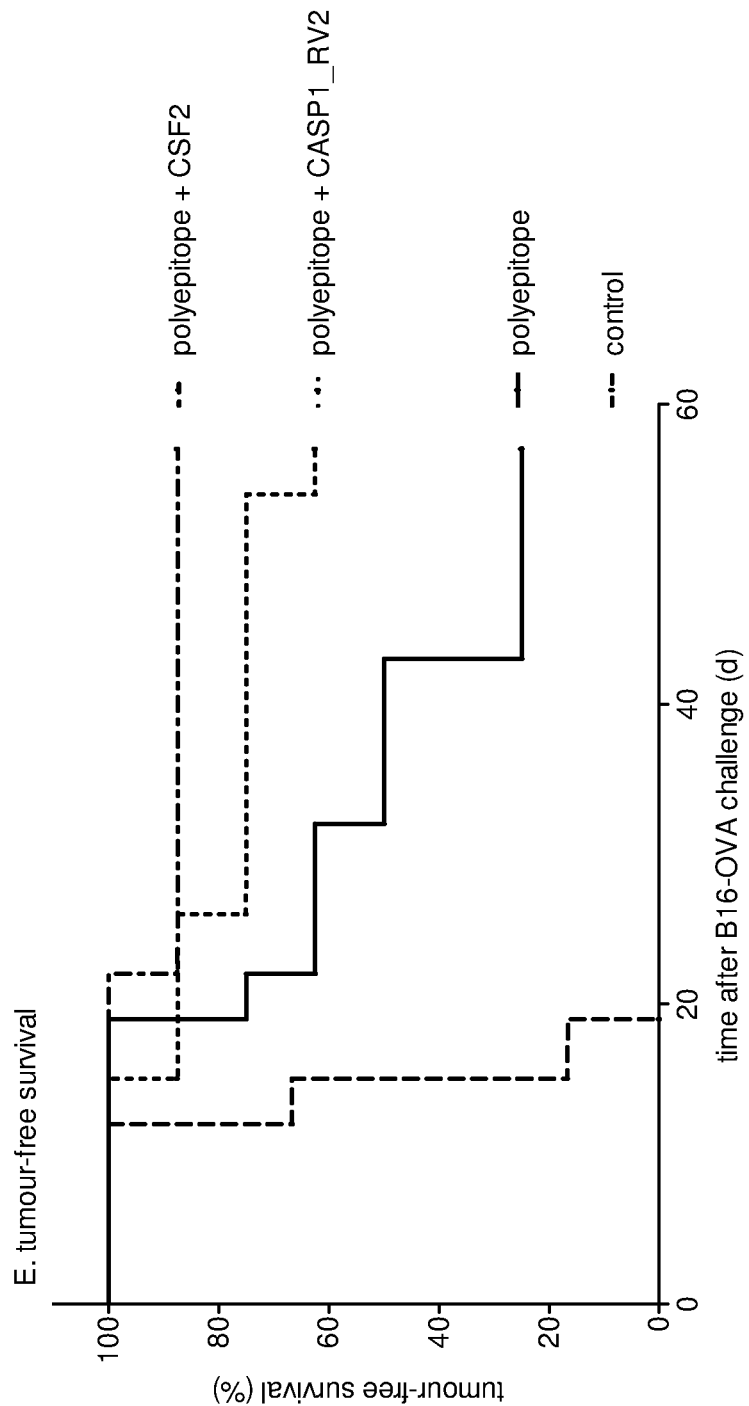

FIG. 4. CASP1_RV2 improves T cell responses and anti-tumour immunity. C57BL/6 mice were vaccinated intradermally with polyepitope vaccine (SEQ ID NO: 23, 10 µg) together with empty vector control, CASP1_RV2 (SEQ ID NO: 4) or reference adjuvant CSF2 (SEQ ID NO: 24, 10 µg) on day 0. On days 6 (A), 9 (B), 13 (C), and 44 (D) post vaccination, OVA-specific CD8 T cells responses were evaluated by tetramer staining. Mice were challenged with B16-OVA cells on day 29, and tumour outgrowth was then followed for another 3 months. E. Tumour-free survival.

Figure 5:
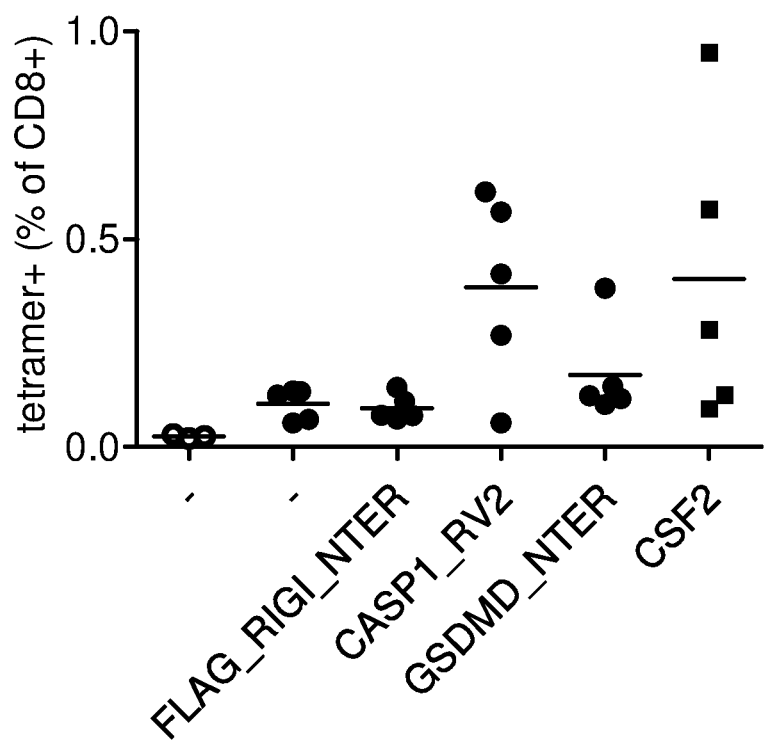

FIG. 5. Active forms of Ddx58 (RIG-I) and Gsdmdc1 (GSDMD) do not improve CD8 T cell immunity. C57BL/6 mice were vaccinated intradermally with 10 µg polyepitope vaccine (closed symbols) or empty vector (open symbols), together with 10 µg empty vector control (-) or plasmids encoding active forms of Ddx58 (SEQ ID NO: 19, FLAG_RIGI_NTER), Caspase-1 (SEQ ID NO: 4, CASP1_RV2), Gsdmdc1 (SEQ ID NO: 14, GSDMD_NTER), or Csf2 (SEQ ID NO: 24, CSF2). On days 8 post vaccination, OVA-specific CD8 T cell responses were evaluated by tetramer staining.

Figure 6:
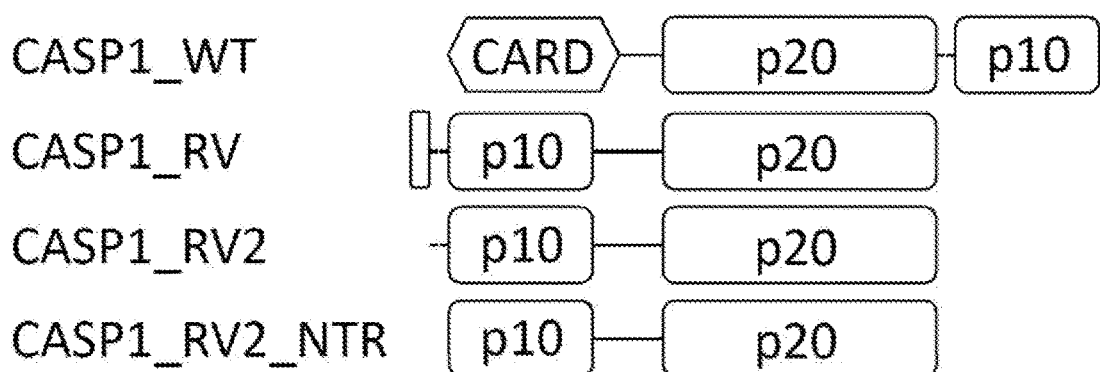
Figure 6:
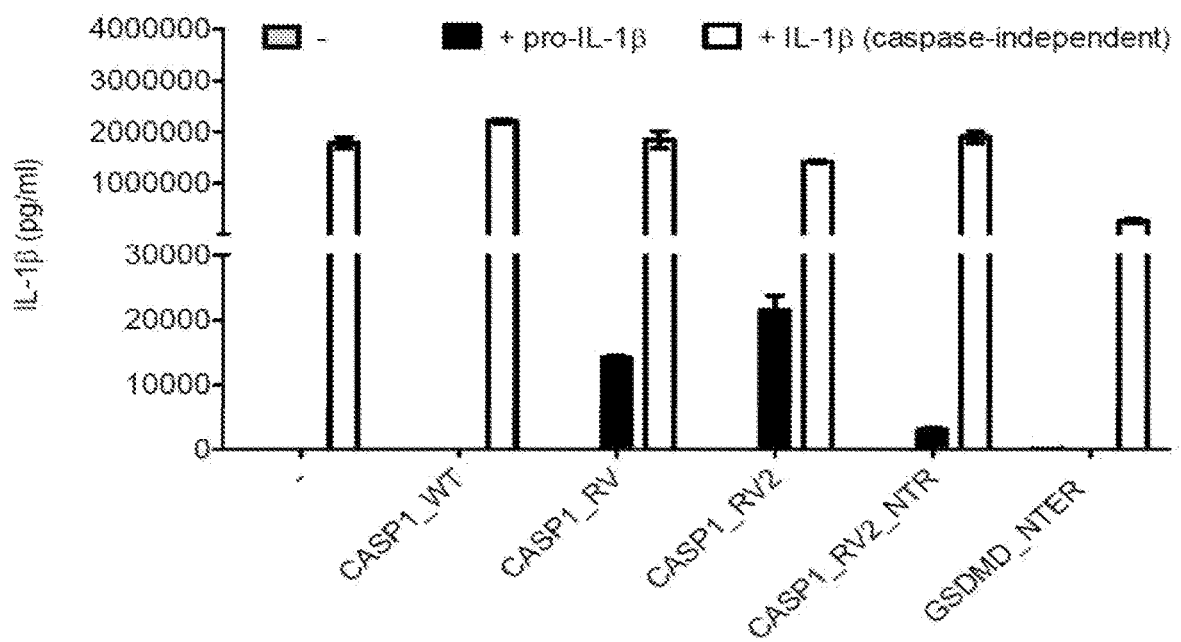
Figure 6:
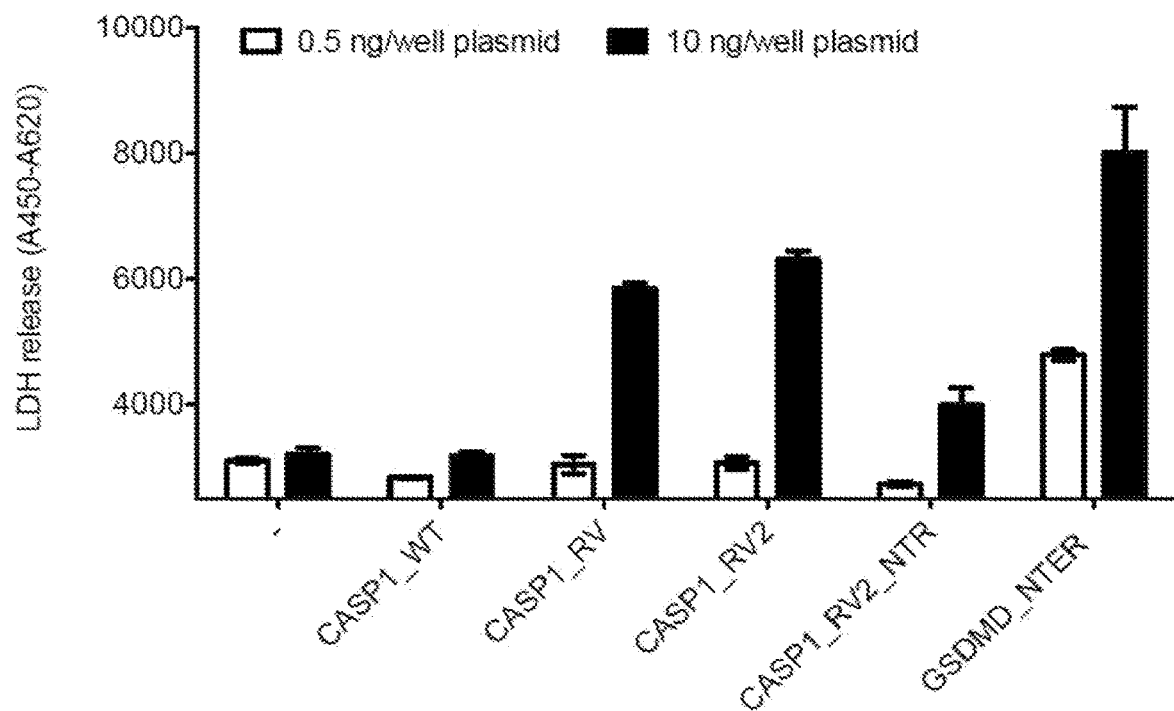

FIG. 6. Progressive N-terminal truncations of constitutively active mouse caspase-1 reveal requirement for retaining part of the p20-p10 inter-domain linker (IDL) at the N-terminus for optimal CASP1_RV activity. (A) Schematic representation of N-terminal variants of CASP1_RV. The N-terminal sequences upstream of the p10 domain are MVLLKDSVRDSEEDFLTDAIFEDD (CASP1_RV, SEQ ID NO: 3), MSEEDFLTDAIFEDD (CASP1_RV2, SEQ ID NO: 4) and M (CASP1_RV2_NTR, SEQ ID NO: 38). B16-F10 cells were co-transfected with 0.5 or 10 ng/well (100 µl) of the indicated caspase-1 (or GSDMD N-terminus, SEQ ID NO: 14) and 10 ng/well IL-1β DNA plasmids, and (B) IL-1β (0.5 ng/well caspase-1) and (C) LDH activity (0.5 and 10 ng/well caspase-1) were measured in supernatants 2 days later.

Figure 7:
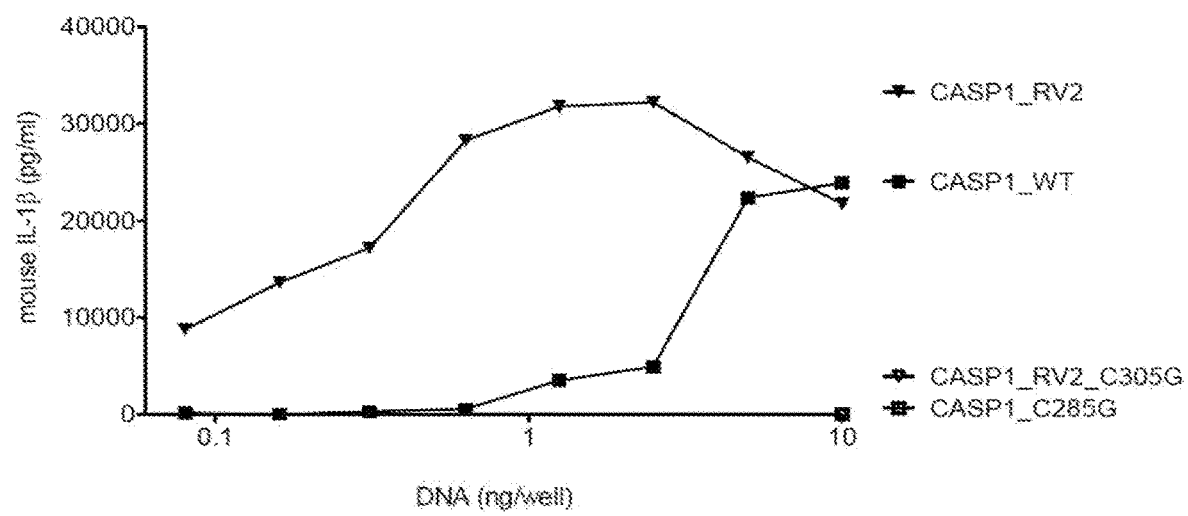
Figure 7:
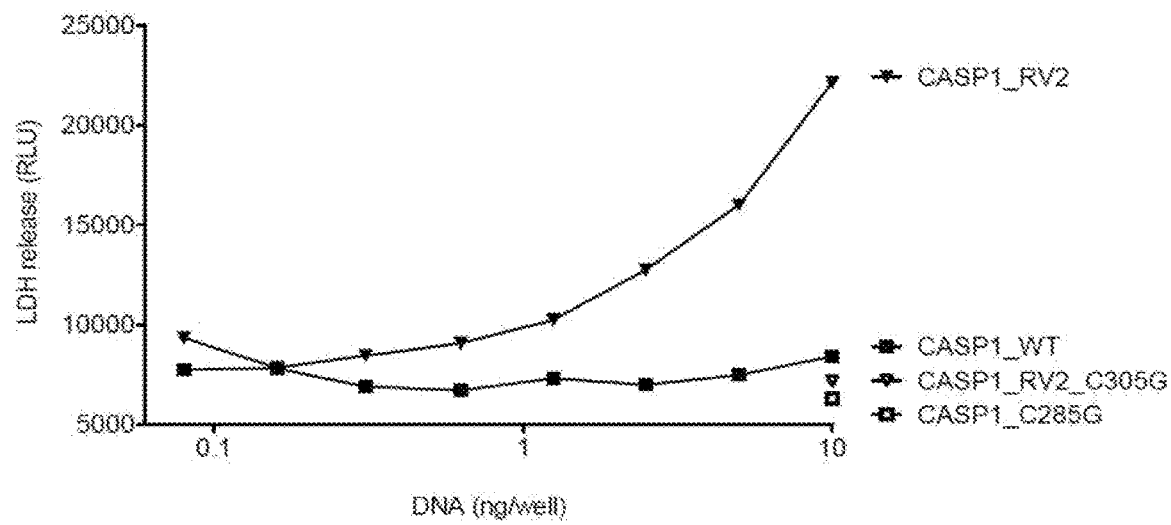

FIG. 7. Constitutively active mouse caspase-1 (CASP1_RV2) is approximately 30-fold more potent than wild-type caspase-1 (CASP1_WT). B16-F10 cells were co-transfected with the indicated amounts of caspase-1 plasmids (serially diluted in insert-less plasmids to maintain a constant total amount of plasmid in the assay) together with 10 ng pro-IL1β plasmid per 100 µl, and (A) IL-1δ and (B) LDH activity in supernatants were assessed 2 days later. Active site mutants of CASP1_RV2 [SEQ ID NO: 4] and CASP1_WT [SEQ ID NO: 1] were CASP1_RV2_C305G [SEQ ID NO: 39] and CASP1_C285G [SEQ ID NO: 2], respectively.

Figure 8:
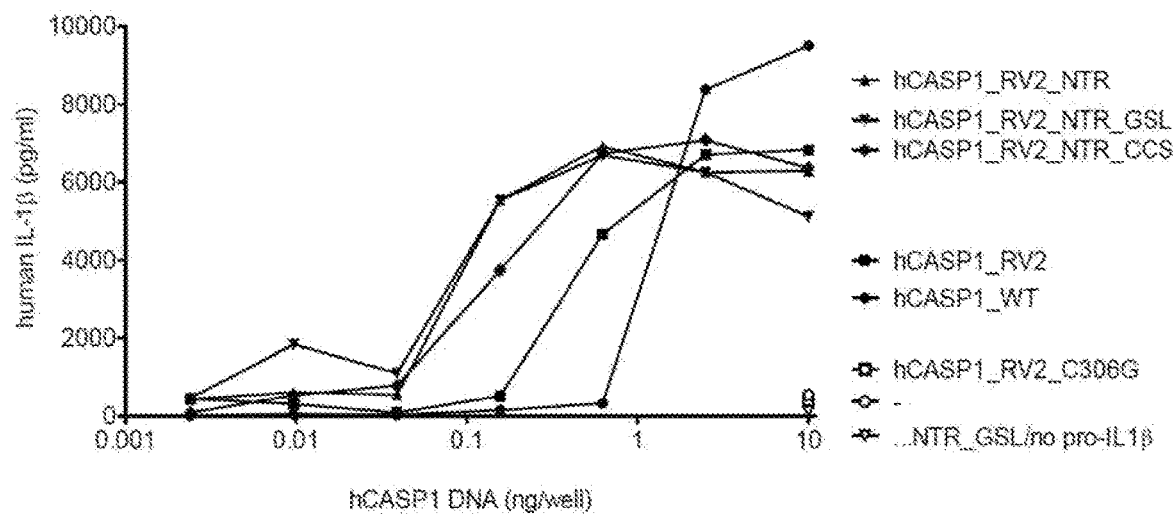
Figure 8:
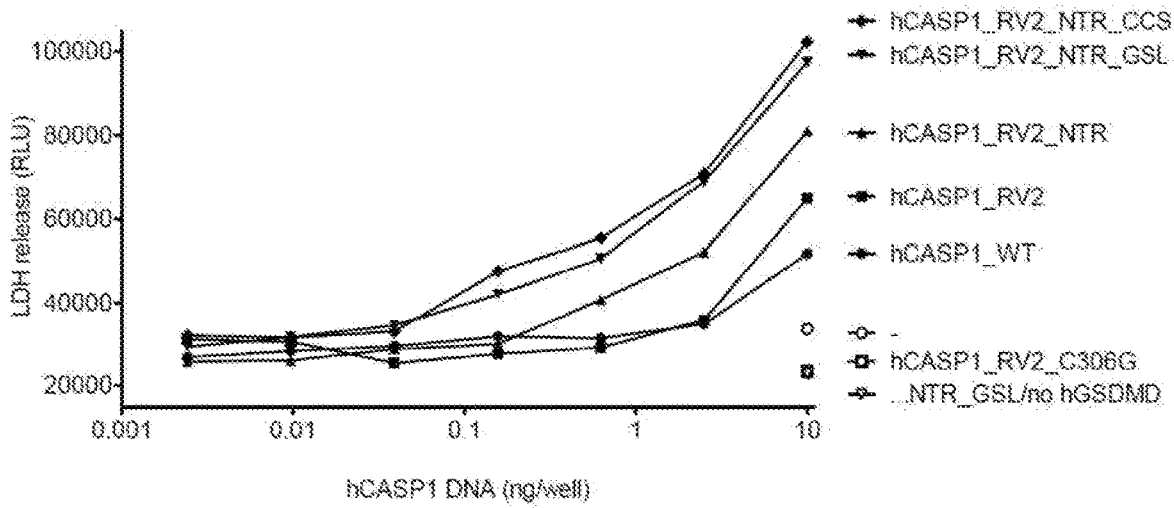

FIG. 8. 293 cells were co-transfected with the indicated concentrations of human caspase-1 (hCASP1) variants [SEQ ID NOs: 35, 44, 49-52], serially diluted in empty vector plasmid to keep the total DNA concentration constant, together with 10 ng/well plasmid either encoding (A) pro-IL1β [SEQ ID NO: 37] or (B) human GSDMD [SEQ ID NO: 53]. Two days later supernatants were harvested to determine (A) IL1β concentrations or (B) LDH activity.

Figure 9:
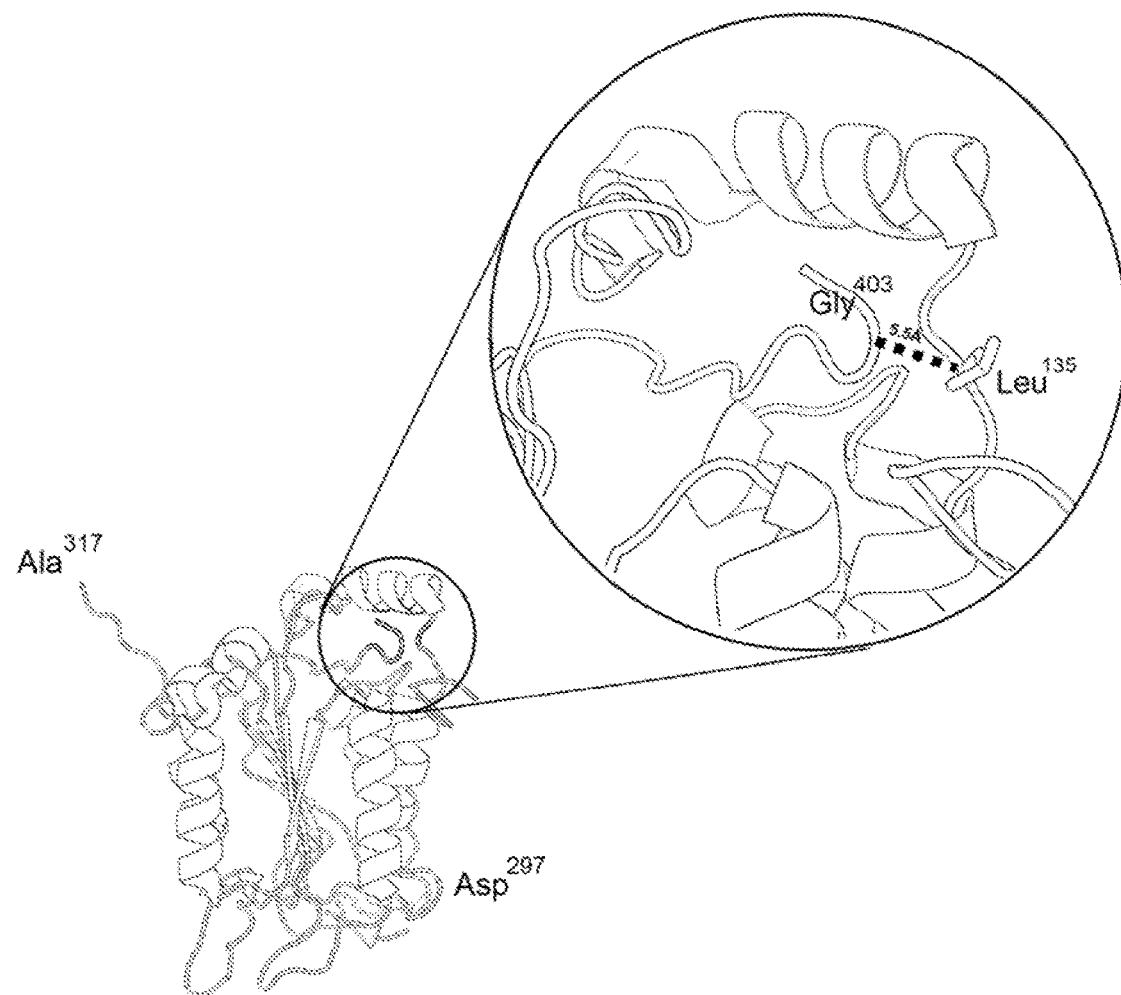
Figure 9:
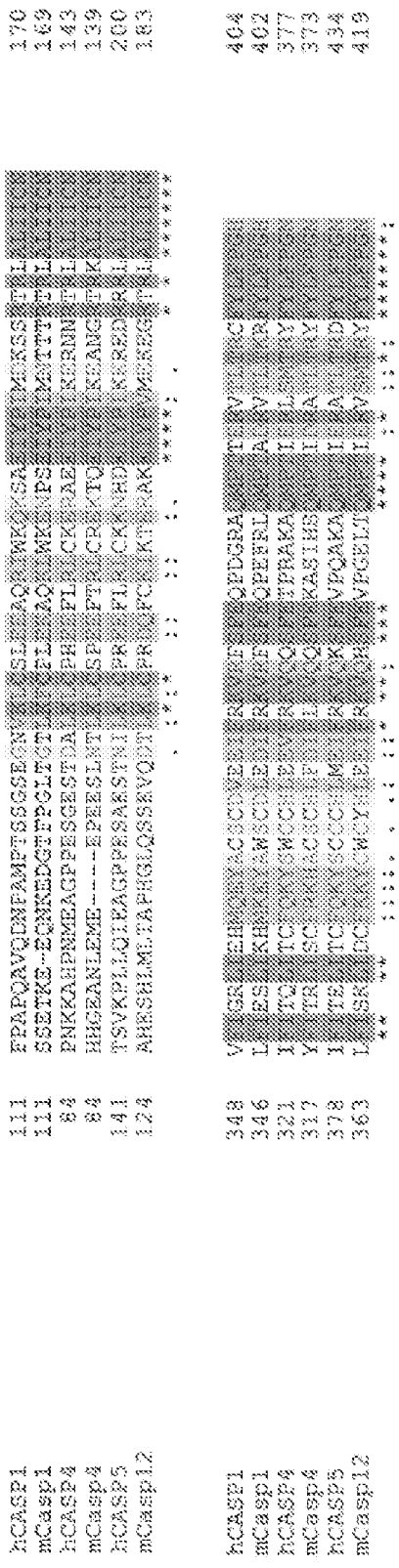

FIG. 9. (A) Crystal structure of human caspase-1. Note the proximity of the C-terminally located Gly403 of the p10 domain (amino acids 317-404) and the N-terminal Leu135 of the p20 domain (amino acid 135-297). Adapted from Yang et al. (2018) Proc. Natl. Acad. Sci. U.S.A. 115: 6792-6797. (B) Sequence alignment of human and mouse pro-inflammatory caspases. Note the conservation of the mCasp1-C135/hCASP1-C136 (next to hCASP1-L135) and mCasp1-G401/hCASP1-G403 amino acid residues.

4. DETAILED DESCRIPTION OF THE INVENTION

4.1 Definitions

The term "cell death", as is used herein, is the event of a biological cell ceasing to carry out its functions. This may be the result of the natural process, or may result from factors such as disease, localized injury, or death of an organism encompassing the cells. Different types of cell death, including apoptosis and pyroptosis, are often defined by morphological criteria.

The term "programmed cell death", as is used herein, refers to any type of cell death engaged by an active predestined molecular mechanism.

The term "apoptosis", as is used herein, refers to cell death accompanied by rounding-up of the cell, retraction of pseudopodes, reduction of cellular volume (pyknosis), chromatin condensation, nuclear fragmentation (karyorrhexis), and plasma membrane blebbing.

The term "necrosis", as is used herein, refers to unprogrammed cell death by cellular damage or infiltration by pathogens. Necrosis is characterized by a gain in cell volume, swelling of organelles, rupture of the plasma membrane and subsequent loss of intracellular contents.

The term "necroptosis", as is used herein, refers to a programmed form of cell death by a caspase-independent fashion, involving activation of mixed lineage kinase domain like pseudokinase (MLKL) and the acute permeabilization of the plasma membrane. Necroptosis can serve as a anti-viral defense mechanism, allowing the cell to undergo "cellular suicide" in the presence of viral caspase inhibitors, thereby restricting virus replication.

The term "pyroptosis", as is used herein, refers to a programmed form of cell death in which activation of inflammatory caspases leads to cleavage of gasdermin and permeabilization of the cell membrane. In addition, the activated caspases may cleave pro-cytokines such as pro-Interleukin 1 beta (proIL1β) and pro-IL18 into their biologically active forms, which are then released as a result of cell permeabilization. Pyroptosis occurs upon infection with intracellular pathogens. Pyroptosis promotes the rapid clearance of various bacterial and viral infections by removing intracellular replication niches and enhancing the host's defensive responses.

The term "T-cell mediated immune response", as is used herein, refers to protective mechanisms that are responsible for detecting and destroying intracellular pathogens, e.g., cells that are infected with viruses or bacteria. T-cell mediated immune responses can also contribute to the destruction of tumour cells. Key players are CD4+ and CD8+ T cells, which produce inflammatory cytokines such as Interferon gamma (IFN-γ) and Tumor Necrosis Factor (TNF). In addition, CD8+ T cells have the ability to induce apoptosis of infected and/or transformed cells.

The term "apoptosis-associated speck-like protein containing a CARD (ASC)", as is used herein, refers to an adapter protein (human protein UniProt: Q9ULZ3) that is s composed of two protein-protein interaction domains: a N-terminal PYRIN-PAAD-DAPIN domain (PYD) and a C-terminal caspase-recruitment domain (CARD). The human gene encoding ASC is termed PYCARD (HGNC: 16608; Entrez Gene: 29108; Ensembl: ENSG00000103490). Activated ASC is a key mediator in pyroptosis and serves as a scaffold for activation of inflammatory caspases such as caspase-1.

The term "caspase-1", as is used herein, refers to a protein (human protein UniProt: P29466) that is a member of the cysteine-aspartic acid protease (caspase) family. Caspases exist as inactive proenzymes that undergo proteolytic processing at conserved aspartic residues to produce 2 subunits, large and small, that dimerize to form the active enzyme. The human gene encoding caspase-1 is termed CASP1 (HGNC: 1499; Entrez Gene: 834; Ensembl: ENSG00000137752.

The term "gasdermin D", as is used herein, refers to a protein that is cleaved by an inflammatory caspase into a N-terminal and C-terminal part. After cleavage, the N-terminal part moves to the plasma membrane where it forms pores, thus promoting release of mature interleukin (IL) 1B and IL18 and triggering pyroptosis. Full length gasdermin D comprises 484 amino acids (human protein UniProt: P57764), of which amino acid residues 1-275 constitute the N-terminal part, and amino acid residues 276-484 the C-terminal part. The human gene encoding gasdermin D is termed GSDMD (HGNC: 25697; Entrez Gene: 79792; Ensembl: ENSG00000104518).

The term "inflammatory caspase", as is used herein, refers to a caspase that is able to induce pyroptosis. Said inflammatory caspase preferably is selected from one or more of caspase-1, caspase-4, caspase-5, and caspase-12.

The term 'protein variant" as is used herein, refers to a protein that has a similar activity as the endogenous protein. A protein variant can be an active part of a protein, or a homologous but not identical protein or part thereof. Said homologous protein or part thereof is active and preferably more than 70% identical to the corresponding human protein, more preferred at least 80% identical, such as more than 90% identical, more than 95% identical or more than 99% identical to the corresponding human protein.

As will be understood by a person skilled in the art, the term "% identity" refers to the % identity as determined over the full length of the proteins, except when the protein variant refers to an active part of a protein.

A preferred protein variant is an active or inducible protein. Preferred protein variants of ASC, caspase 1, and gasdermin D are depicted in Tables 1 and 2.

The term "active or inducible protein", as is used herein, refers to a protein that is dominantly active, without a need for activation, or of which the activity can be induced, for example by overexpression, transcriptional activation or by dimerization. An example of inducible transcriptional activation is provided by a tetracycline-controlled gene expression system (Yamada et al., 2018. Cell Rep 25: 487-500.e6). An example of inducible dimerization is provided by an optical dimerizer system that is based on the interacting domains of phytochromes and cryptochromes of bacteria and plants. Examples of such interacting domains are *Arabidopsis thaliana* cryptochrome 2 (CRY2) and CRY2-interacting basic Helix-Loop-Helix (CIB1; Taslimi et al., 2016. Nature Chem Biol 12: 425-430), and a FK506-binding protein (FKBP) and FKBP-rapamycin binding (Frb) domain of mTOR, which can be induced to dimerize by rapamycin (Kohler and Bertozzi, 2003. Chem Biol 10:1303-11) and variants thereof such as Shield 1 (Banaszynski et al., 2006. Cell 126: 995-1004). Commercially available systems include iDimerize Inducible Homodimer System (Takara, Kusatsu, Japan).

The term "antigen", as is used herein, refers to a molecule that can be specifically recognised by the adaptive immune system, that is, by B cells and/or T cells. A sequence within an antigen that is bound by an antibody or a T-cell receptor is called an epitope. A preferred antigen comprises one or more epitopes specific for or highly expressed in cancer, including neo-epitopes, epitopes from pathogens such as bacteria and viruses, and/or synthetic epitopes that do not occur in nature. The term "neo-epitope", as is used herein, refers to an epitope that arises through non-synonymous somatic DNA mutations that change the amino acid coding sequences. A preferred T cell epitope comprises 8-20 amino acid residues, more preferred 8-13 amino acid residues. A preferred antigen is or comprises a polyepitope, comprising 2-50, preferably 5-25 individual epitopes, preferably each contained within a sequence of 8-40 amino acid residues. The individual epitopes in a polyepitope may be alternated by spacer sequences of, preferably, 1-10 amino acid residues.

Said antigen preferably also comprises G-actin, or F-actin binding sequences such as GGVADLIKKFESISKEE (Riedl et al 2008, Nat Methods. 5:605). Actin is liberated by dying cells and binds to Dendritic cell Natural killer lectin Group Receptor 1 (DNGR-1) on conventional type 1 DCs (cDC1s; Ahrens et al. 2012, Immunity 36: 635-645; Zhang et al. 2012. Immunity 36: 646-657), important for cross-priming CD8 T cell responses (Schulz et al. 2018, Cell Reports 24:419-428). The inclusion of actin or actin-binding sequences may therefore result in more efficient cross-priming of CD8 T cells by cDC1s and thus a more effectively stimulated immune response.

The term "accessory molecule", as is used herein, refers to a molecule that may facilitate T-cell mediated immune responses, including an immune checkpoint inhibitor and a further immune stimulating molecule such as a chemokine and/or a cytokine.

The term "immune checkpoint inhibitor", as is used herein, refers to a molecule that blocks an inhibitory interaction between immune cells and other cells or cytokines and which may thereby increase the killing of cancer cells. Examples of checkpoint interacting molecules are PD-1/PD-L1 and CTLA-4/B7-1/1B7-2. A preferred immune checkpoint inhibitor is a molecule that blocks an interaction between PD-1 and PD-L1. Said molecule that blocks an interaction between PD-1 and PD-L1 preferably is an antibody against PD1 and/or an antibody against PDL1.

The term "a further immune stimulating molecule", as is used herein, refers to a molecule that facilitates T-cell mediated immune responses such as cytotoxic T lymphocyte induction. Such molecules include pro-inflammatory cytokines, for example interleukins (IL-) such as IL-1β, IL-6, IL-12, granulocyte-macrophage colony stimulating factor (CSF2), and tumor necrosis factor (TNF), chemokines such as monocyte chemoattractant protein or MCP-1, as are listed in Table 3. A preferred another immune stimulating molecule is a an IL-12 family member, such as IL-12, IL-23, IL-27 and/or IL-35 and/or CSF2.

The term "genetic vaccine", or gene vaccine, as is used herein, refers to a vaccine that comprises one or more RNA or DNA nucleic acid sequences that encode antigens against which an immune response is to be directed. Genetic vaccines that induce cellular immune responses provide a means to generate specific cellular responses, while avoiding risks associated with, for example, attenuated pathogenic bacteria or viruses.

The term "vaccine", as is used herein, refers to an immune-stimulating molecule, preferably an antigen, that stimulates an immune response against said molecule. Said immune response preferably confers active immunity against an agent that comprises and/or expresses said immune-stimulating molecule by stimulating the immune system to attack the agent. The term vaccine includes a composition comprising an immune-stimulating molecule and an adjuvant.

The term "systemic administration", as is used herein, refers to parenteral administration such as, for example, intravenous, intraperitoneal, intranasal, intradermal, transdermal or intramuscular administration.

The term "local administration", as is used herein, refers to topical administration to body surfaces such as, for example, administration to the skin, eyes, mucous membranes, or through inhalation.

The term "shuffled", also termed "swapped", as used herein, refers to a recombinant protein in which the order of conserved domains has been altered. A caspase comprising shuffled or swapped p10 and p20 domains is a recombinant caspase in which the p10 domain is N-terminal to the p20 domain.

4.2 A Protein as an Inducer of Pyroptosis

In one embodiment, an inducer of pyroptosis, preferably said constitutively active pro-inflammatory caspase comprising shuffled p10 and p20 domains, optionally connected by a protease cleavable site, is provided as a protein that is expressed in a host cell. Said constitutively active pro-inflammatory caspase preferably is a constitutively active pro-inflammatory caspase-1.

Based on the human caspase-1 sequences (UniProt accession code P29466), caspase-1 is generated as a propeptide. Human caspase-1 (SEQ ID NO:52) contains a caspase recruitment domain (CARD: SEQ ID NO:54) from amino acid residue 1 to amino acid residue 92. Residues 93-119 constitute a linker between the CARD and p20 domains, also known as the CARD-domain linker (CDL: SEQ ID NO:55). The p20 subunit domain (SEQ ID NO:56) stretches from amino acid residue 120 to amino acid residue 297 and contains an enzymatically active site around Cys285. The p20 domain is followed by a small p20-p10 inter-domain linker (IDL: SEQ ID NO:57) from amino acid residue 298 to amino acid residue 316, and a p10 subunit (SEQ ID NO:58) from amino acid residue 317 to amino acid residue 404.

It has been suggested that a CARD domain is required in active caspase-possessing an N-terminal CARD domain (Boucher et al., 2018. J Exp Med 215: 827-840). Surprisingly, a preferred constitutively active pro-inflammatory caspase according to the invention comprising shuffled p10 and p20 domains preferably lacks a caspase-recruitment domain (CARD).

Said constitutively active pro-inflammatory caspase, was based on constitutively active versions of human apoptosis-inducing executioner caspase-3 and -6 (Srinivasula et al., 1998. J Biol Chem 273: 10107-11). As described in this article, for example in the design of active caspase-3, the N-terminal p20 and C-terminal p10 domains were swapped and separated by a short (8 AA) caspase-3 cleavage site. A part of the sequence upstream of p10, including a few p20 amino acids, was also moved by this swap. Hence, the N-terminus of resulting active caspase began with four p20 amino acids, followed by the small p20-p10 inter-domain linker (IDL) and p10 (Srinivasula et al., 1998. J Biol Chem 273: 10107-11).

It is noted that enzymatically inactive pro-caspase-3 already is a stable dimer that changes conformation upon cleavage of the inter-domain linker (IDL), suggesting a spring-loaded mechanism where cutting the IDL releases strain and allows the enzyme to reorganize into the active conformation. In contrast, caspase-1 requires cleavage of the IDL and dimerisation for activation. Hence, it was investigated whether a constitutively active caspase-1 could be generated by shuffling of the p10 and p20 domains.

A constitutively active murine inflammatory caspase-1 (CASP1_RV, SEQ ID NO: 3) was generated as described in Srinivasula et al., 1998 (Srinivasula et al., 1998. J Biol Chem 273: 10107-11). Accordingly, the N-terminus of murine CASP1_RV began with five p20 amino acids and the IDL. However, testing three CASP1_RV variants progressively lacking more of this N-terminus showed that removal of the N-terminal p20 remnant in CASP1_RV2 [SEQ ID NO: 4] increased, but further removal of the IDL in CASP1_RV2_NTR [SEQ ID NO: 38] decreased the activity of CASP1_RV. In other words, the most active CASP1_RV2 variant retained most of the highly negatively charged IDL sequence SEEDFLTDAIFEDD at its N-terminus. Compared to wild-type murine caspase-1 (CASP1_WT), CASP1_RV2 was approximately 30-fold more potent in in vitro assays. Thus, despite differences between human caspase-3 and mouse caspase-1, such as the presence of a CARD domain in caspase-1 and a difference in activation mechanism, the Srinivasula-approach indeed generated constitutively active mouse caspase-1.

The design of a constitutively active human caspase-1 variant (hCASP1_RV2, SEQ ID NO: 35) was based on murine CASP1_RV2, and therefore also began with 14 amino acids of the inter-domain linker GNISLPT-TEEFEDD. Surprisingly, and in striking contrast with murine CASP1_RV2, removing all N-terminal residues upstream of p10 (hCASP1_RV2_NTR, SEQ ID NO: 49) greatly increased its activity.

A preferred constitutively active pro-inflammatory caspase comprising shuffled p10 and p20 domains is thus a constitutively active pro-inflammatory caspase-1 comprising shuffled p10 and p20 domains which lacks one or more of the negatively charged amino acid residues D and E in the IDL sequence in front of the P10 domain, preferably lacks the inter-domain linker SVGVSGNLSLPTTEEFEDD, preferably the complete inter-domain linker SVGVSGNLSLPTTEEFEDD.

In a preferred constitutively active pro-inflammatory caspase comprising shuffled p10 and p20 domains, a start codon, ATG, preferably is positioned in front of the p10 sequences, preferably directly in front of the p10 sequences.

The intervening sequence between shuffled p10 and p20 domains appears to be flexible. Crystal structures of caspase-1 in its active conformation (Yang et al., 2018. Proc Natl Acad Sci USA 115: 6792-6797) seem to suggest that the distance between the C-terminus of the p10 domain and the N-terminus of the p20 domain is small. Removing aspartic acid protease sites in this region of mouse and human caspase-1 comprising shuffled p10 and p20 domains [SEQ ID NO:s 40-43, 45-47] did not affect their ability to process pro-IL1β, suggesting that autoproteolysis did not contribute to its activity (data not shown). Rather, this region appeared to serve merely as a flexible linker. In fact, reducing the size of the linker to 9 amino acids was not a neutral event, as was expected, but surprisingly increased the activity of hCASP1_NTR, irrespective of the presence of an autoproteolytic target site in the smaller linker. Compared to wild-type human caspase-1, the resulting hCASP1_NTR_GSL [SEQ ID NO: 50] was approximately 30-fold more potent in in vitro assays. Thus, and again in contrast to mouse caspase-1, swapping the p10 and p20 domains did not significantly increase the activity of human caspase-1. However, removing the IDL-remnant at the N-terminus and reducing the size of a linker between the swapped p10 and p20 domains unexpectedly did yield a constitutively active human caspase-1.

A preferred constitutively active pro-inflammatory caspase comprising shuffled p10 and p20 domains comprises a glycine corresponding to G401 (SEQ ID NO:1) which is located at a distance from 0 to 40 amino acids residues from a cysteine corresponding to C135 (SEQ ID NO:1), preferably at a distance of 1-10 amino acid residues. A most preferred constitutively active pro-inflammatory caspase according to the invention has a reduced distance between G401 and C135 residues and therefore lacks a linker between p10 and p20.

SEQ ID NO:1 corresponds to the mouse caspase-1 sequence. A skilled person will understand that the term "corresponding to", as is used herein above, is meant to indicate that the equivalent amino acid residue in a different caspase-1 sequence, might not be the amino acid residue at the same position in different caspase. For example, mouse C135 corresponds to human C136. Similarly, G401 in the mouse corresponds to human G403. Hence, a preferred constitutively human active pro-inflammatory caspase-1 comprising shuffled p10 and p20 domains comprises a glycine corresponding to G403 which is located at a distance from 0 to 40 amino acids residues from a cysteine corresponding to C136, preferably at a distance of 0-10 amino acid residues. A most preferred constitutively active human pro-inflammatory caspase-1 according to the invention has a reduced distance between G403 and C136 residues and therefore lacks a linker between shuffled p10 and p20 domains.

Said linker may be a linker polypeptide comprising from about 1 amino acid residue to about 40 amino acid residues, most preferred to about 35 amino acid residues such as to 30 amino acid residues, to 20 amino acid residues, to 15 amino acid residues, to 10 amino acid residues, such as 2 amino acid residues. Some preferred examples of such linker polypeptide sequences include Gly-Ser linkers, for example of the type $(Gly_x\ Ser_y)_z$ such as, for example, $(Gly_4\ Ser)_3$, $(Gly_4\ Ser)_7$ or $(Gly_3\ Ser_2)_3$, as described in WO 99/42077, and the GS30, GS15, GS9 and GS7 linkers described in, for example, WO 06/040153 and WO 06/122825.

Commonly used expression systems for heterologous protein production include *E. coli*, baculovirus, yeast, Chinese Hamster Ovary cells (CHO), human embryonic kidney (HEK) cells and derivatives thereof including HEK293 cells including HEK293T, HEK293E, HEK-293F and HEK-293FT (Creative Biolabs, NY, USA), and PER.C6® cells (Thermo Fisher Scientific, MA, USA). The efficiency of expression of recombinant proteins in heterologous systems depends on many factors, both on the transcriptional level and the translational level.

Said inducer of pyroptosis, for example a protein selected from ASC, caspase-1, and/or gasdermin D, or a variant thereof, preferably an active or inducible variant, more preferably said constitutively active pro-inflammatory caspase comprising shuffled p10 and p20 domains, may be produced using prokaryotic cells, preferably *E. coli*, fungi, most preferably filamentous fungi or yeasts such as *Saccharomyces cerevisiae* and *Pichia pastoris*, or eukaryotic cells, preferably mammalian cells such as HEK cells and derivatives thereof. Commercial systems for expression in mammalian cells are available, for example the Expi293 mammalian transient protein expression system (Thermo Fisher Scientific, Waltham (MA) USA).

Production of an inducer of pyroptosis in filamentous fungi is preferably performed as described by Joosten et al., 2005. J Biotechnol 120:347-359, which is included herein by reference.

Production of an inducer of pyroptosis in *Pichia pastoris* is preferably performed as described by Rahbarizadeh et al., 2006. J Mol Immunol 43:426-435, which is included herein by reference.

Production of an inducer of pyroptosis in HEK cells and/or derivatives thereof is preferably performed as described by Thomas and Smart, 2005. J Pharmacol Toxicol Methods 51: 187-200, and/or Lin et al., 2015. PLOS ONE 10: e0123562.

Said inducer of pyroptosis, preferably said constitutively active pro-inflammatory caspase comprising shuffled p10 and p20 domains, is preferably produced by the provision of a nucleic acid encoding said inducer of pyroptosis to a cell of interest. Said nucleic acid, preferably DNA, is preferably produced by recombinant technologies, including the use of polymerases, restriction enzymes, and ligases, as is known to a skilled person. Alternatively, said nucleic acid is provided by artificial gene synthesis, for example by synthesis of partially or completely overlapping oligonucleotides, or by a combination of organic chemistry and recombinant technologies, as is known to the skilled person. Said nucleic acid is preferably codon-optimised to enhance expression of the inducer of pyroptosis in the selected cell or cell line. Further optimization preferably includes removal of cryptic splice sites, removal of cryptic polyA tails and/or removal of sequences that lead to unfavourable folding of the mRNA. The presence of an intron flanked by splice sites may encourage export from the nucleus in eukaryotic cells. In addition, the nucleic acid preferably encodes a protein export signal for secretion of the inducer of pyroptosis out of the cell into the periplasm of prokaryotes or into the growth medium, allowing efficient purification of the inducer of pyroptosis.

Methods for purification of an inducer of pyroptosis are known in the art and are generally based on chromatography, such as ion exchange, to remove contaminants. In addition to contaminants, it may also be necessary to remove undesirable derivatives of the product itself such as degradation products and aggregates. Suitable purification process steps are provided in Berthold and Walter, 1994 (Berthold and Walter, 1994. Biologicals 22: 135-150).

As an alternative, or in addition, a recombinant inducer of pyroptosis may be tagged with a specific tag by genetic engineering to allow the protein attach to a column specific to the tag and therefore be isolated from impurities. The purified protein is then exchanged from the affinity column with a decoupling reagent. The method has been increasingly applied for purifying recombinant protein. Conventional tags for proteins, such as histidine tag, is used with an affinity column that specifically captures the tag (eg., a Ni-IDA column for a histidine tag) to isolate the protein from other impurities. The protein is then exchanged from the column using a decoupling reagent according to the specific tag (eg., immidazole for histidine tag). This method is more specific, when compared with traditional purification methods. Suitable further tags include c-myc domain, hemagglutinin tag, and maltose-binding protein, glutathione-S-transferase, maltose-binding protein, FLAG tag peptide, biotin acceptor peptide, streptavidin-binding peptide and calmodulin-binding peptide, as presented in Chatterjee, 2006. Cur Opin Biotech 17, 353-358). Methods for employing these tags are known in the art and may be used for purifying the inducer of pyroptosis.

4.3 An Expression Construct as an Inducer of Pyroptosis

Further provided is an expression construct that encodes an inducer of pyroptosis, preferably said constitutively active pro-inflammatory caspase comprising shuffled p10 and p20 domains, according to the invention. Said expression construct preferably comprises means for high expression levels such as strong promoters, for example of viral origin (e.g., human cytomegalovirus) or promoters derived from genes that are highly expressed in a cell such as a mammalian cell (Running Deer and Allison, 2004. Biotechnol Prog 20: 880-889; U.S. Pat. No. 5,888,809). The construct preferably comprises a selection system such as, for example, expression of glutamine synthetase or expression of dihydrofolate reductase for amplification of the vector in a suitable recipient cell, as is known to the skilled person.

Said construct may be a viral vector, preferably a viral vector that is able to transduce dividing and non-dividing cancer cells. Said viral vector preferably is a recombinant adeno-associated viral vector, a herpes simplex virus-based vector, a pox virus-based vector such as a modified vaccinia Ankara-based vector as described in WO2011128704, or a lentivirus-based vector such as a human immunodeficiency virus-based vector. Said viral vector most preferably is a retroviral-based vector such as a lentivirus-based vector such as a human immunodeficiency virus-based vector, or a gamma-retrovirus-based vector such as a vector based on Moloney Murine Leukemia Virus (MoMLV), Spleen-Focus Forming Virus (SFFV), Myeloproliferative Sarcoma Virus (MPSV) or on Murine Stem Cell Virus (MSCV). A preferred retroviral vector is the SFG gamma retroviral vector (Riviere et al., 1995. PNAS 92: 6733-6737).

Retroviruses, including a gamma-retrovirus-based vector, can be packaged in a suitable complementing cell that provides Group Antigens polyprotein (Gag)-Polymerase (Pol) and/or Envelop (Env) proteins. Suitable packaging cells are human embryonic kidney derived 293T cells, Phoenix cells (Swift et al., 2001. Curr Protoc Immunol, Chapter 10: Unit 10 17C), PG13 cells (Loew et al., 2010. Gene Therapy 17: 272-280) and F1p293A cells (Schucht et al., 2006. Mol Ther 14: 285-92).

A preferred expression construct is a non-viral expression construct for in vivo expression of an inducer of pyroptosis, preferably said constitutively active pro-inflammatory caspase comprising shuffled p10 and p20 domains. Non-viral vectors include circular or linear DNA molecules, and RNA molecules such as messenger RNA. A non-viral expression construct may be packaged in liposomes, lipoplexes or polyplexes, and/or provided as a molecular conjugate. Minicircle DNA molecules or linear DNA molecules free of plasmid bacterial DNA sequences may be generated in vitro and may express an inducer of pyroptosis at high levels in vivo.

Said expression construct may further comprise a nucleic acid encoding another immune stimulating molecule such as a cytokine.

As an alternative, or in addition, said expression construct may be combined with an expression construct coding for another immune stimulating molecule.

4.4 Application of Induced Pyroptosis

The invention provides an inducer of pyroptosis, preferably said constitutively active pro-inflammatory caspase comprising shuffled p10 and p20 domains, for use in a method of stimulating an immune response in an individual, preferably a T-cell mediated immune response, comprising administering said inducer of pyroptosis to the individual. Said inducer of pyroptosis, preferably said constitutively active pro-inflammatory caspase comprising shuffled p10 and p20 domains, is preferably used for preventive or therapeutic administration in humans suffering from a disease, or at risk to suffer from a disease. Said diseases include but are not limited to measles, rubella, cholera, meningococcal disease, influenza, diphtheria, mumps, tetanus, hepatitis A, hepatitis B, hepatitis E, pertussis, tuberculosis, pneumococcal disease, typhoid fever, poliomyelitis, tick-borne encephalitis, *Haemophilus influenzae* type b, rabies, varicella and herpes zoster (shingles), human papilloma-virus, human immunodeficiency virus, respiratory syncytial virus, cytomegalovirus, rotavirus gastroenteritis, yellow fever, Japanese encephalitis, malaria, dengue fever, Zika virus-related microcephaly, anthrax, plague, Q fever, smallpox, or from a non-infectious diseases such as cancer.

In one embodiment, said disease is a cancer. Said individual may suffer or may be treated to prevent the recurrence of a cancer, including but not limited to a carcinoma, an adenoma, a melanoma, a sarcoma, a leukemia, a germ cell cancer, a blastoma, and/or a lymphoma.

Said carcinoma includes adenocarcinoma, squamous cell carcinoma, adenosquamous carcinoma, anaplastic carcinoma, large cell carcinoma and small cell carcinoma and encompasses bladder cancer, breast cancer, kidney cancer, pancreatic cancer, ovarian cancer, lung cancer, liver cancer, head and neck cancer, squamous cell carcinoma, colorectal cancer, cervical cancer, renal cell carcinoma, stomach cancer, prostate cancer, melanoma, brain cancer, thyroid cancer, uterine cancer, esophageal cancer.

Said sarcoma includes Askin's tumour, chondrosarcoma, Ewing's sarcoma, malignant schwannoma, osteosarcoma and soft tissue sarcomas, including fibrosarcoma, leiomyosarcoma, liposarcoma, and rhabdomyosarcoma.

Said leukemia includes acute and chronic leukemia, comprising lymphoblastic leukemia such as Burkitt's leukemia, myelogenous leukemia such as acute myelogenous leukemia (AML) and chronic myelogenous leukemia (CML), Hairy cell leukemia (HCL), T-cell prolymphocytic leukemia, large granular lymphocytic leukemia, adult T-cell leukemia, and clonal eosinophilia.

Said germ cancer includes germinomatous or seminomatous germ-cell tumours such as germinoma, dysgerminoma and seminoma, and nongerminomatous or nonseminomatous germ-cell tumours such as teratoma and polyembryoma.

Said blastoma includes hepatoblastoma, medulloblastoma, nephroblastoma, neuroblastoma, pancreatoblastoma, pleuropulmonary blastoma, retinoblastoma, glioblastoma multiforme, and gonadoblastoma.

Said lymphoma includes Hodgkin's lymphoma, non-Hodgkin's lymphoma, B-cell lymphoma, T-cell lymphoma, Burkitt's lymphoma, follicular lymphoma, mantle cell lymphoma, small lymphocytic lymphoma, and lymphoplasmacytic lymphoma.

4.5 Intratumoural Administration

Preferred cancers in embodiments of the invention are cancers that form a body mass, such as sarcomas, germ cancers and carcinomas. An inducer of pyroptosis, for example an active or inducible protein selected from ASC, caspase-1, and/or gasdermin D, more preferably said constitutively active pro-inflammatory caspase comprising shuffled p10 and p20 domains, may be administered locally to an individual that is suffering from a cancer, preferably intratumourally. The resulting pyroptosis of the cancer cells will release damage-associated molecular patterns together with cancer-specific antigens, preferably cancer neoepitopes, that will activate tumour-specific T cells that will start attacking the remaining cancer cells and eventually even may clear the cancer.

Said inducer of pyroptosis, for example an active or inducible protein selected from ASC, caspase-1, and/or gasdermin D, more preferably said constitutively active pro-inflammatory caspase comprising shuffled p10 and p20 domains, may be intratumourally administered as a protein or, preferably, as an expression construct that expresses said inducer of pyroptosis in the cancer cells. Said administration of an inducer of pyroptosis into a tumour preferably is by intratumoural injection, preferably by injection or electroporation, as is known to a person skilled in the art. Said electroporation may be applied on isolated cells in vitro or, preferably, in vivo. An effective amount of an inducer of pyroptosis, preferably said constitutively active pro-inflammatory caspase comprising shuffled p10 and p20 domains, as a protein that is administered intratumourally is a dosage large enough to produce the desired effect in which the symptoms of the cancer are ameliorated or even nullified. A therapeutically effective amount preferably does not cause adverse side effects. Generally, a therapeutically effective amount may vary with the individual's age, condition, and sex, as well as the extent of the disease and can be determined by one of skill in the art. The dosage may be adjusted by the individual physician in the event of any complication. A therapeutically effective amount may vary from about 1 microgram to about 100 milligram, preferably from about 10 microgram to about 10 milligram, most preferably from about 0.1 milligram to about 1 milligram, in one or repeated dose administrations, for one or more days.

Suitable transfection reagents for transducing cells such as cancer cells with a protein include Saint-PROTEINS transfection reagent (Synvolux, Leiden, the Netherlands).

Said effective amount of an inducer of pyroptosis, preferably said constitutively active pro-inflammatory caspase comprising shuffled p10 and p20 domains, as a protein preferably is provide as a buffered solution, preferably having a pH values between 5 and 9, preferably between 6 and 8. Said buffered solution may, for example, comprise a phosphate-, histidine- or succinate-based buffer, polysorbate, trehalose dihydrate, and/or methionine.

An expression construct such as a non-viral expression construct, expressing an inducer of pyroptosis, preferably said constitutively active pro-inflammatory caspase comprising shuffled p10 and p20 domains, may be administered in an effective amount to an individual in need thereof. Preferred is repeated administration, such as repeated administration on 2 to 5 or more consecutive days in order to effectively induce an immune response against the cancer in order to treat a cancer.

An expression construct such as a non-viral expression construct, expressing an inducer of pyroptosis, preferably said constitutively active pro-inflammatory caspase comprising shuffled p10 and p20 domains, preferably is administered by injection or electroporation into a tumour. Preparations for intratumoural administration may comprise sterile aqueous or non-aqueous solutions suspensions, and emulsions. Examples of non-aqueous solvents are propylene glycol, polyethylene glycol, vegetable oils such as olive oil, and injectable organic esters such as ethyl oleate. Preparations for intratumoural administration preferably comprise aqueous carriers such as water optionally including a buffering agent and salts, saline such as sodium chloride solution, Ringer's dextrose, dextrose and sodium chloride, or lactated Ringer's. Preservatives and other additives may also be present such as, for example, antimicrobials, anti-oxidants, chelating agents, and inert gases and the like.

A therapeutically effective amount of an expression construct expressing an inducer of pyroptosis, such as a non-viral expression construct, may vary from about 0.001 mg to about 100 mg, preferably from about 0.01 mg to about 10 mg, most preferably from about 0.1 mg to about 1 mg.

The invention further provides a method of ameliorating and/or treating an individual suffering from a cancer, and/or preventing recurrence of a cancer, the method comprising administering an effective amount of an inducer of pyroptosis, preferably said constitutively active pro-inflammatory caspase comprising shuffled p10 and p20 domains, to said individual to stimulate an immune response in the individual against a cancer neoepitope, thereby ameliorating and/or treating said individual.

Suitable transfection reagents for transfecting or transducing cells, especially cancer cells, with an expression construct such as a non-viral expression construct include cationic polyplexes such as polyethylenimine, liposomes or lipoplexes comprising cationic lipids such as DOTAP or pyridinium-based lipids such as Saint-DNA and Saint-mRNA transfection reagents (Synvolux, Leiden, the Netherlands).

4.6 Systemic Administration

The invention provides an inducer of pyroptosis, preferably said constitutively active pro-inflammatory caspase comprising shuffled p10 and p20 domains, for use in a method of stimulating an immune response in an individual, preferably a T-cell mediated immune response, comprising administering said inducer of pyroptosis to the individual, wherein said inducer of pyroptosis is administered systemically as an adjuvant of a vaccine, preferably a genetic vaccine.

For therapeutic applications, an inducer of pyroptosis, preferably said constitutively active pro-inflammatory caspase comprising shuffled p10 and p20 domains, as is described herein is administered to an individual suffering from a disease such as a cancer or an infection in an amount sufficient to at least partially halt the disease, preferably to cure the disease, and/or to reduce or halt any disease-associated complications. An amount adequate to accomplish this is defined as a "therapeutically effective dose." Amounts effective for this use will depend upon the severity of the disease and the general state of the individual's health and method of administration. Single or multiple administrations of an inducer of pyroptosis may be administered depending on the dosage and frequency as required and tolerated by the patient.

For prophylactic applications, an inducer of pyroptosis, preferably said constitutively active pro-inflammatory caspase comprising shuffled p10 and p20 domains, as is described herein is administered to an individual to induce an immune response that can help protect against the establishment or recurrence of a disease.

An expression construct such as a non-viral expression construct, expressing an inducer of pyroptosis, preferably said constitutively active pro-inflammatory caspase comprising shuffled p10 and p20 domains, may be formulated as an aqueous solution including a buffering agent, a saline such as sodium chloride, Ringer's dextrose, dextrose and sodium chloride, lactated Ringer's or fixed oils. Preservatives and other additives may also be present such as, for example, antimicrobials, anti-oxidants, chelating agents, and inert gases and the like.

A therapeutically effective amount of an expression construct expressing an inducer of pyroptosis, preferably said constitutively active pro-inflammatory caspase comprising shuffled p10 and p20 domains, such as a non-viral expression construct, may vary from about 0.001 mg to about 100 mg, preferably from about 0.01 mg to about 10 mg, most preferably from about 0.1 mg to about 1 mg.

Said vaccine, preferably a genetic vaccine, encodes one or more antigens, i.e. particular proteins or parts thereof, against which a protective or therapeutic immune response is desired. Said one or more antigens are either derived from a pathogen, for example a pathogen that causes a disease selected from measles, rubella, cholera, meningococcal disease, influenza, diphtheria, mumps, tetanus, hepatitis A, hepatitis B, hepatitis E, pertussis, tuberculosis, pneumococcal disease, typhoid fever, poliomyelitis, tick-borne encephalitis, *Haemophilus influenzae* type b, rabies, varicella and herpes zoster (shingles), human papilloma-virus, human immunodeficiency virus, respiratory syncytial virus, cytomegalovirus, rotavirus gastroenteritis, yellow fever, Japanese encephalitis, malaria, dengue fever, Zika virus-related microcephaly, anthrax, plague, Q fever, and smallpox, or are expressed by a cancer.

Examples of antigens, optionally encoded by a genetic vaccine include Human immunodeficiency virus (HIV) envelope protein (gp160), HIV-Nef, measles hemagglutinin glycoprotein, measles fusion glycoprotein, measles nucleocapsid protein, rubella E1 protein, rubella E2 protein, rubella capsid protein, cholera toxin, cholera B subunit protein, meningococcal NadA D, NHBA D, FHBP D, PorA VR1 D, PorA VR2 D and/or subvariants thereof (Brehony et al., 2015. Euro Surveill 20: 10.2807/1560-7917.ES.2015.20.49.30084), influenza virus hemagglutinin, influenza virus nucleoprotein, diphtheria toxoid, mumps virus envelope glycoprotein, mumps virus hemagglutinin-neuraminidase, mumps virus hemolysis cell fusion (F) glycoprotein, mumps virus matrix envelope protein, tetanus toxoid, hepatitis A virus surface antigen, hepatitis B virus surface antigen, hepatitis E virus surface antigen, pertussis toxin, pertussis filamentous hemagglutinin, pertussis pertactin, tuberculosis ESAT-6, tuberculosis CFP10 (van Pinxteren et al., 2000. Clin Diagn Lab Immunol 7: 155-160), pneumococcal capsular antigen, *Salmonella typhi* O antigen, *Salmonella typhi* H antigen, *Salmonella typhi* 50 kDa outer membrane protein, poliovirus D antigen, poliovirus C antigen, tick-borne encephalitis virus domain III, *Haemophilus influenzae* type a antigen, *Haemophilus influenzae* type b antigen, rabies virus glycoprotein, Varicella-Zoster virus glycoprotein E, human papilloma-virus L1 capsid protein, rotavirus E1A glycoprotein, yellow fever envelope (E) glycoprotein, Japanese encephalitis envelope protein domain III, *Plasmodium falciparum* glutamate dehydrogenase, histidine rich protein II, lactate dehydrogenase, and/or fructose-bisphosphate aldolase protein, dengue fever virus antigens (DEN-1 to DEN-4, Zika virus nonstructural protein 1, anthrax toxin, *Yersinia pestis* fraction 1 capsular antigen, *Yersinia pestis* fraction V protein, Q fever virus 27-kDa outer membrane protein (Com1), vaccinia virus A30, B7 and F8 antigens (Sakhatskyy et al., 2008. Virology 371: 98-107), and any fragments or combinations thereof.

Preferred examples of antigens that may be encoded by a genetic vaccine are cancer neoepitopes or other tumour-associated antigens. Said cancer neoepitopes result from non-synonymous mutations, insertions or deletions in the open reading frame encoding said neoepitope in a cancer cell, resulting in altered amino acids compared to epitopes from healthy cells. Said cancer neoepitopes may differ between different cancers and individual patients. Hence, said cancer antigens preferably are developed as personalized cancer vaccines. For this, cancer cells and corresponding healthy cells are isolated from a patient, followed by sequence analysis of genomic DNA, and/or transcribed mRNAs. A comparison of the sequences obtained from cancer cells and corresponding healthy cells will result in the identification of sequences that are altered in the cancer cells, when compared to the corresponding healthy cells.

To develop said personalized cancer vaccines, software tools have been developed that detect cancer somatic mutations and predict potential tumour-specific neoepitopes. Said software tools include, but are not limited to, TSNAD: an integrated software for cancer somatic mutation and tumour-specific neoepitope detection (Zhou et al., 2017. R Soc Open Sci 4: 170050); CloudNeo: a cloud pipeline for identifying patient-specific tumour neoepitopes (Bais et al., 2017. Bioinformatics, 33: 3110-3112); pVAC-Seq: a genome-guided in silico approach to identifying tumour neoepitopes (Hundal et al., 2016. Genome Medicine 8:11) and pVACtools: Computational selection and visualization of neoepitopes for personalized cancer vaccine design (Kiwala et al., 2018. Cancer Genetics 226-227: 45-46).

Said cancer neoepitopes can be formulated as peptides/proteins, or encoded in RNA or DNA molecules. RNA and DNA vaccines can encode several epitopes on a single molecule. Preferred genetic vaccines introduce DNA coding for cancer neoepitopes into host cells, where they are expressed and ultimately lead to the presentation of epitopes to T cells.

To stimulate a cellular immune response, antigens comprising, for example, cancer neoepitopes are preferably processed into 8- to 20-residue peptides and loaded onto a major histocompatibility complex (MHC) class I and/or class II molecules for recognition by CD8+ and/or CD4+ T cells, respectively. Said 8- to 20-amino acid residue peptides are preferably provided as a DNA expression construct encoding a preprotein, also termed polyepitope, that is processed by proteases into one or more cancer neoepitopes.

Said preprotein preferably encompasses 2-50 individual cancer neoepitopes, more preferably 2-40, more preferably 3-30, more preferably 5-25 individual cancer neoepitopes. Said individual cancer neoepitopes, or sequences comprising said neoepitopes, may be flanked by additional amino acids, and separated by small spacer sequences, preferably of 1-10 amino acid residues, preferably 1-5 amino acid residues such as 2 amino acid residues, 3 amino acid residues or 4 amino acid residues.

A genetic vaccine directs expression of said one or more antigens from an RNA or DNA expression construct. Antigen expression from a DNA expression construct is driven by a transcriptionally active promoter such as a viral promoter. Said promoter preferably is selected from a SV40 promoter, a Rous Sarcoma Virus (RSV) promoter and most preferred, a cytomegalovirus (CMV) immediate early promoter, as is known to a person skilled in the art. Additional modifications to improve expression rates include optimization of the codon usage for expression in eukaryotic cells; the insertion of promoter enhancer sequences; the insertion of synthetic introns; presence of 5' UTR and/or 3' UTR sequences such as adenovirus tripartite leader (TPL) sequences or Woodchuck Posttranscriptional Regulatory Element (WPRE); and modifications to the polyadenylation and transcriptional termination sequences to include a strong polyadenylation/transcriptional termination signal, such as bovine growth hormone or rabbit beta-globin polyadenylation sequences.

Said genetic vaccine may further comprise a nucleic acid encoding another immune stimulating molecule such as a cytokine. An inducer of pyroptosis, for example an active or inducible protein selected from ASC, caspase-1, and/or gasdermin D, non-limiting examples of which are provided in Tables 1-2, more preferably an expression construct as detailed herein above under 4.3, may be for use in a method of stimulating an immune response in an individual in combination with a vaccine, preferably a genetic vaccine, as described herein above, whereby said inducer of pyroptosis is administered in combination with one or more accessory molecules such as another immune stimulating molecule such as a cytokine, a chemokine, an agonistic antibody, and/or an inhibitor of immune suppressing molecules, including but not limited to an antagonistic antibody and/or a soluble ligand. Said accessory molecule may be administered as a small molecule, a protein, or as an expression construct, simultaneous, separate or sequential to the administration of the inducer of pyroptosis and the vaccine, preferably genetic vaccine.

A preferred accessory molecule is selected from an another immune stimulating molecule listed in Table 3, preferably IL-12, IL-2, IL-4, CSF2, interferon, IL-18, TNF, and/or Ox-40, most preferred IL-12 and/or CSF2, an agonistic Flt3-antibody, and/or an immune checkpoint inhibitor such as a PD1 or PD-L1 blocker such as pembrolizumab (Merck), nivolumab (Bristol-Myers Squibb), pidilizumab (Medivation/Pfizer), MEDI0680 (AMP-514; AstraZeneca) and PDR001 (Novartis); fusion proteins such as a PD-L2 Fc fusion protein (AMP-224; GlaxoSmithKline); atezolizumab (Roche/Genentech), avelumab (Merck/Serono and Pfizer), durvalumab (AstraZeneca), BMS-936559 (Bristol-Myers Squibb); and small molecule inhibitors such as PD-1/PD-L1 Inhibitor 1 (WO2015034820; (2S)-1-[[2,6-dimethoxy-4-[(2-methyl-3-phenylphenyl)methoxy]phenyl] methyl]piperidine-2-carboxylic acid), BMS202 (PD-1/PD-L1 Inhibitor 2: WO2015034820; N-[2-[[[2-methoxy-6-[(2-methyl[1,1'-biphenyl]-3-yl)methoxy]-3-pyridinyl]methyl]amino]ethyl]-acetamide), and PD-1/PD-L1 Inhibitor 3 (WO/2014/151634; (3S,6S,12S,15S,18S,21S,24S,27S,30R,39S,42S,47aS)-3-((1H-imidazol-5-yl)methyl)-12,18-bis((1H-indol-3-yl)methyl)-N,42-bis(2-amino-2-oxoethyl)-36-benzyl-21,24-dibutyl-27-(3-guanidinopropyl)-15-(hydroxymethyl)-6-isobutyl-8,20,23,38,39-pentamethyl-1,4,7,10,13). Further anti-PD1 molecules include ladiratuzumab vedotin (Seattle Genetics).

Said systemic administration of an inducer of pyroptosis, preferably said constitutively active pro-inflammatory caspase comprising shuffled p10 and p20 domains, as is described herein above, and the simultaneous, separate or sequential administration of a genetic vaccine as is described herein above, preferably administered as an expression construct, preferably a non-viral expression construct, preferably is parenteral such as, for example, intravenous, intraperitoneal, intranasal, intramuscular or, most preferred, intradermal.

4.7 Immune-Stimulating Compositions

The invention further provides an immune-stimulating composition, comprising an inducer of pyroptosis, preferably said constitutively active pro-inflammatory caspase comprising shuffled p10 and p20 domains, and a pharmacologically acceptable excipient. Said inducer of pyroptosis preferably is selected from the molecules depicted in Tables 1-2, more preferably is a constitutively active pro-inflammatory caspase comprising shuffled p10 and p20 domains.

Said pharmaceutically acceptable excipient which is a non-toxic material that does not interfere with the effectiveness of the biological activity of the active ingredient. The term "physiologically acceptable" refers to a non-toxic material that is compatible with a biological system such as a cell, cell culture, tissue, or organism. The characteristics of the carrier will depend on the route of administration. Physiologically and pharmaceutically acceptable excipients include diluents, fillers, salts buffers, stabilizers, solubilizers, and other materials which are well known in the art.

A preferred immune-stimulating composition according to the invention further comprises a genetic vaccine, preferably a genetic vaccine encoding 1-50 cancer neoepitopes as described herein above.

Said inducer of pyroptosis, preferably said constitutively active pro-inflammatory caspase comprising shuffled p10 and p20 domains, and said genetic vaccine in an immune-stimulating composition of the invention preferably are expressed from a non-viral expression construct. Non-viral expression constructs include mRNA or naked DNA such as plasmid DNA and in vitro amplified DNA. A non-viral expression construct may be packaged in liposomes and/or provided as a molecular conjugate. Minicircle DNA vectors free of plasmid bacterial DNA sequences may be generated in bacteria and may express a nucleic acid encoding an inducer of pyroptosis at high levels in vivo.

The invention further provides an immune-stimulating composition according to the invention for use in a method for treatment of a cancer.

The invention further provides a method of treating an individual suffering from a cancer, said method comprising providing an immune-stimulating composition comprising an inducer of pyroptosis, preferably said constitutively active pro-inflammatory caspase comprising shuffled p10 and p20 domains, and a genetic vaccine according to the invention to an individual in need thereof to thereby treat the individual.

The invention further provides a use of an immune-stimulating composition comprising an inducer of pyroptosis, preferably said constitutively active pro-inflammatory caspase comprising shuffled p10 and p20 domains, and a genetic vaccine according to the invention in the preparation of a medicament for treating an individual suffering from a cancer.

Said inducer of pyroptosis, preferably said constitutively active pro-inflammatory caspase comprising shuffled p10 and p20 domains, preferably is administered in combination with another immune stimulating molecule such as a cytokine such as IL-12 and CSF2.

The invention further provides a method of stimulating an immune response in an individual, preferably a T-cell mediated immune response, comprising providing an inducer of pyroptosis, preferably said constitutively active pro-inflammatory caspase comprising shuffled p10 and p20 domains, and administering said inducer of pyroptosis to the individual.

For the purpose of clarity and a concise description, features are described herein as part of the same or separate embodiments, however, it will be appreciated that the scope of the invention may include embodiments having combinations of all or some of the features described.

5, EXAMPLES

Example 1

Materials and Methods
DNA Constructs

Expression constructs containing DNA coding for mediators of pyroptosis (Table 1) were generated by Gibson assembly. Briefly, (fragments of) Pycard, Casp1, Gsdmdc1, Il1b, Il18, Ripk3, Mlkl (*Mus musculus*), CASP1, IL1B (*Homo sapiens*) were amplified from D1 (a dendritic cell line of C57BL/6 origin, see Winzler et al., 1997. J Exp Med 185: 317-328) cDNA, or from synthetic, codon-optimised DNA (Pycard, Csf2, hCASP1_RV2; Integrated DNA Technologies, Coralville, IA, USA) and cloned into vector pD2610-v10 (ATUM, Newark, CA, USA) using a Gibson Assembly Cloning Kit (New England Biolabs, Ipswich, MA, USA). Constructs encoding dasher GFP (SEQ ID NO: 13), Reps1, a small, irrelevant peptide sequence (SEQ ID NO: 20), or lacking an insert altogether, served as controls.

In vaccination experiments, adjuvant or control plasmids were combined with a polyepitope DNA vaccine (SEQ ID NO: 23) coding for three tumour-specific antigens (Dpagt1, Reps1, Adpgk; see SEQ ID NO: NOs: 25-27) derived from the C57BL/6 MC38 colon carcinoma cell line, as well as two model antigens (OT-II, OT-I; see SEQ ID NO: NOs: 28 and 29) from chicken ovalbumin, separated by a 'spacer sequence' consisting of three alanines (see SEQ ID NO: 30).

All plasmids were grown using *E. coli* strain DH5a and purified using a Macherey-Nagel (Dueren, Germany) Endotoxin-Free (EF) plasmid purification kit. For vaccination, plasmids underwent an additional purification step on a Nucleobond filter, followed by centrifugation (30 min, 10,000 g, 4° C.) to remove any remaining debris.
Mice and Cell Lines C57BL/6 (Jico) mice were purchased from Jackson laboratory (Bar Harbor, ME, USA) and housed under FELASA-compliant conditions at the LUMC animal facility. B16-F10, a melanoma cell line of C57BL/6 origin, was maintained in culture medium consisting of IMDM (ThermoFisher-Gibco, Waltham, MA, USA) supplemented with 8% fetal calf serum (Sigma-Aldrich, Zwijndrecht, the Netherlands) in the presence of L-glutamine, penicillin and streptomycin (all from ThermoFisher-Gibco) in a humidified CO2-incubator (37° C., 5% CO2). B16-OVA is a B16-F10 cell line stably transfected with ovalbumin and was cultured under the same conditions.
Transfections B16-F10 cells were plated at 2,000 cells/well in a 96-well flat bottom plate in 100 µl culture medium. One day later, they were transfected by the addition of 10 µl DNA complexed with Saint-DNA (Synvolux products, Leiden, the Netherlands), a cationic lipid-based transfection reagent. Two days after transfection, cell death and/or the release of DAMPS were analysed by flow cytometry, ELISA or LDH assay.
Flow Cytometry Non-adherent and adherent cells were harvested by removing the cell supernatants, rinsing the wells with PBS and subsequently treating the remaining adherent cells with trypsin (ThermoFisher-Gibco). After mixing and centrifugation of the supernatant and trypsin-treated cells in 96-well V-bottom plates, the resulting cells were washed with FACS buffer (PBS, 1% BSA, 0.02% azide) and exposed to 7-aminoactinomycin D (7-AAD) (Biolegend, San Diego, CA, USA), a dye that enters dead cells that have lost membrane integrity, diluted in FACS buffer for 15 minutes. The cells were then immediately analysed on a Guava EasyCyte HT flow cytometer equipped with a 488 nm laser (Merck MilliPore, Burlington, MA, USA)
IL-1β ELISA To measure IL-1β, cellular supernatants were centrifuged to remove cell debris and analysed by sandwich ELISA, using protocols provided by the supplier (Biolegend, San Diego, CA). Briefly, 96-well plates were coated with capture antibody overnight. After washing away unbound antibody (4 washing steps), 50-1000-fold diluted supernatant (and, for reference, titrated recombinant IL-1β) was added and incubated for 2 h at room temperature while shaking. After 4 washing steps, biotinylated detection antibody was added and incubated for 1 h at RT, followed by another 4 wash steps and a 30-minute incubation with streptavidin-HRP. After washing away strep-HRP, TMB substrate solution was added. Absorbance at 450 nm and 570 nm was read on a Tecan Infinite F50 (Tecan Group Ltd, Männedorf, Switzerland).
LDH Assay A colorimetric assay to quantitatively measure lactate dehydrogenase (LDH) released into the culture media (LDH Cytotoxicity Assay Kit, ThermoFisher-Pierce, Waltham, MA, USA) was used to quantify cell death. This assay is based on a coupled enzymatic reaction. First, LDH catalyzes the conversion of lactate to pyruvate via reduction of NAD+ to NADH. Second, diaphorase uses NADH to reduce a tetrazolium salt (INT) to a red formazan product. Therefore, the level of formazan formation is directly proportional to the amount of released LDH in the medium. Briefly, 50 ul reaction mixture was mixed with 50 ul 2-fold diluted culture supernatant. After 30 minutes incubation at room temperature in the dark, stop solution was added, followed by absorbance readings at 450 nm and 620 nm. Percentage cytotoxicity was calculated as follows: ((OD450−OD620)

sample−(OD450−OD620)medium control)/((OD450−OD620)positive control−(OD450−OD620)medium control)×100%.

Mouse Vaccinations and Tumour Challenge

On day 0, male C57BL/6 mice were injected intradermally with 30 μl 0.9% NaCl solution containing 30 μg endotoxin-free plasmid DNA, consisting of 10 μg polyepitope vaccine (see SEQ ID NO: NO:23) (or empty vector control), 10 μg adjuvant (or empty vector), and 10 μg adjuvant 2 (or empty vector). Blood, drawn on several days after vaccination, was treated with erythrocyte lysis buffer and stained with PE-conjugated H2-Kb/SIINFEKL tetramers (LUMC tetramer facility, Leiden, the Netherlands) in PBS supplemented with 0.1% bovine serum albumin and 0.02% sodium azide (PBS/BSA). After a 30-minute incubation at room temperature in the dark, fluorochrome-conjugated antibodies to CD3, CD4, CD8 (Biolegend, San Diego, CA, USA) were added to discriminate T cell subsets, followed by another 30 minutes on ice and 2 washing steps with PBS/BSA to remove unbound tetramers and antibodies. The samples were acquired on a BD LSRII (Becton Dickinson, San Jose, CA, USA) and analysed using FlowJo (FlowJo LLC).

On day 29 after vaccination, mice were injected subcutaneously with 50,000 B16-OVA cells, B16-F10 melanoma cells stably transfected with ovalbumin. Tumour growth was monitored every 3-4 days, and tumour size was calculated as (length×width×width)/2. Mice carrying tumours exceeding 1000 $mm^3$ or with a bleeding ulcer were euthanised by CO2 asphyxiation.

Results

Design of Constitutively Active Caspase-1 Variants

A series of constructs based on ASC (SEQ ID NO: 31), caspase-1 (SEQ ID NO: 1-4, 8, 12), gasdermin D (SEQ ID NO: 14-15), signature signaling molecules in pyroptosis, cDNA sequences was designed (FIG. 1, Table 1, 2, 4). Work using non-inflammatory caspases (Srinivasula et al., 1998. J Biol Chem 273: 10107-11; Park et al., 2006. Biochem Biophys Res Commun 347: 941-8) suggested that a protein consisting of the caspase-1 p10 and p20 domains, in reverse order compared to wild-type Caspase-1 ('reshuffled') and linked by the IL-1β caspase-1 cleavage site would be constitutively active. However, a recent study shows that the active form of caspase-1 also requires the presence of the N-terminal CARD domain (Boucher et al., 2018. J Exp Med 215: 827-840), suggesting that such constructs (CASP1_RV and CASP1_RV2, FIG. 1; SEQ ID NO: 3 and 4, respectively) would not be active. In additional constructs, inducible (iCASP1, SEQ ID NO: 8) or constitutive (dCASP1, SEQ ID NO: 12), dimerisation domains replaced the N-terminal CARD domain that normally links caspase-1 to upstream activating signaling cascades. Finally, a control construct with a mutated active site (CASP1_C285G, SEQ ID NO: 2) as well as a wild-type control (CASP1_WT, SEQ ID NO: 1) was generated.

Constitutively Active Caspase-1 Variants CASP1_RV and CASP1_RV2 Induce Cell Death Upon activation, caspase-1 induces pyroptotic cell death by cleaving gasdermin D (Aglietti and Dueber, 2017. Trends Immunol 38: 261-271). This releases the gasdermin D N-terminal domain, causing it to form cytotoxic pores in the plasma membrane of cells. To test if our caspase-1 variants (FIG. 1) induce cell death, B16F10 cells were transfected with the corresponding plasmids together with a GFP-encoding plasmid (SEQ ID NO: 13). Two days after transfection, wild-type caspase-1 (CASP1_WT) and the active site mutant (CASP1_C285G) had induced little to no cell death (<20% 7-AAD+ cells) compared to the negative control (SEQ ID NO: 20), while the N-terminal domain of GSDMD (SEQ ID NO: 14-15) killed virtually all (>90%) cells (FIG. 2). In contrast with wild-type and point-mutated caspase-1, the 'reshuffled' caspase-1 (CASP1_RV and CASP1_RV2) variants killed the large majority of the B16F10 cells. In addition, most of the dead cells expressed GFP, suggesting that inclusion of active caspase-1 in a genetic vaccine does not prevent the expression of antigen encoded by a DNA vaccine. Thus, in contrast with an earlier report indicating that active caspase-1 requires the CARD domain (Boucher et al., 2018. J Exp Med 215: 827-840), the novel CARD-less 'reshuffled' caspase-1 constructs of the present invention were shown to be constitutively active.

Constitutively Active Caspase-1 Variants CASP1_RV and CASP1_RV2 Induce IL-1β Secretion One of the hallmarks of pyroptosis is the secretion of IL-1β, a pyrogenic cytokine. This cytokine is produced as a cytosolic precursor (pro-IL-1β) and its release requires cleavage by caspase-1 of both pro-IL-1β and gasdermin D (Evavold et al., 2018. Immunity 48: 35-44; Heilig et al., 2018. Eur J Immunol 48: 584-592; Monteleone et al., 2018. Cell Rep 24: 1425-1433). Indeed, the active caspase-1 variants CASP1_RV and CASP1_RV2, but not CASP1_WT and CASP1_C285G, induced IL-1β release from B16-F10 cells co-transfected with pro-IL-1β (SEQ ID NO: 21, FIG. 3). Similarly, caspase-1 dimers, either induced by AP1903 (iCASP1) or constitutive (dCASP1), also yielded IL-1β secretion in this assay.

CASP1_RV2 Improves T Cell Responses and Anti-Tumour Immunity

As the constitutively active forms of caspase-1 (CASP1_RV and CASP1_RV2) induced cell death and were able to induce processing and secretion of IL-1β, we next tested their potential as a genetic adjuvant. To this end, mice were vaccinated with a 1:1 mix of a plasmid coding for a polyepitope vaccine (SEQ ID NO: 23) and a plasmid encoding a genetic adjuvant. The polyepitope vaccine included the ovalbumin-derived CD8+ T cell epitope SIINFEKL, that is recognised by specific T cells when bound to H-2Kb MHC class I molecule. Since CASP1_RV2 was slightly more active than CASP1_RV (FIG. 2-3), the former was used. Shortly after vaccination, CASP1_RV2, but not reference adjuvant CSF2, significantly increased the frequency of SIINFEKL-specific T cells (FIG. 4A) found in blood, while at later time points the adjuvant effects of CASP1_RV2 and CSF2 were similar (FIG. 4B, C).

Intriguingly, challenging the mice with B16-OVA resulted in a massive increase in specific T cell immunity in the CASP1_RV2-adjuvanted group compared to mice that had not received an adjuvant, much greater than for CSF2 (SEQ ID NO: 24, FIG. 4D). This may suggest that this adjuvant works particularly well in heterologous prime-boost regimens (Kardani et al., 2016, Vaccine 34: 413-423).

In mock-vaccinated mice, B16-OVA tumours invariably grew out within three weeks after injection (FIG. 4E). Although the polyepitope vaccine significantly delayed tumour growth, most of the mice eventually did develop a tumour. In contrast, the majority of CASP1_RV2 adjuvanted mice remained tumour-free. Thus, a new constitutively active form of caspase-1 significantly improved both T-cell immunity and tumour protection.

Constitutively Active Forms of RIG-I and GSDMD do not Improve T Cell Immunity

Caspase-1 is a central part of the inflammasome pathway. Therefore, we reasoned that other components of this pathway should be also be able to act as genetic adjuvants. To test this idea, we generated a constitutively active version of Ddx58, also known as RIG-I (SEQ ID NO: 19), and of Gsdmdc1, also known as GSDMD (SEQ ID NO: 14), by removing their C-terminal inhibitory domains. RIG-I can act upstream of caspase-1 to promote IL-1β processing and release (Poeck et al. 2010, Nature Immunology 11: 63-69), and GSDMD is a downstream target of caspase-1 responsible for membrane disruption. These constructs both induced cell death (FIG. 2). In addition, and in contrast with all other constructs tested, transfection of B16F10 cells with the RIG-I construct resulted in production of IFNβ and IL-6 (data not shown). Surprisingly, however, when tested for their adjuvant activity in combination with the polyepitope vaccine, only the active caspase-1 construct improved T cell responses (FIG. 5).

Example 2

Materials and Methods
DNA Constructs

Expression constructs containing DNA coding for mediators of pyroptosis (Table 1 and Table 4) were generated by Gibson assembly. Briefly, (fragments of) Casp1, Gsdmdc1, Il1b, (Mus musculus), IL1B, GSDMD (Homo sapiens) were amplified from D1 (a dendritic cell line of C57BL/6 origin, see Winzler et al., 1997. J Exp Med 185: 317-328) or 293 cDNA, or from synthetic, codon-optimised DNA (CASP1; Integrated DNA Technologies, Coralville, IA, USA) and cloned into vector pD2610-v10 (ATUM, Newark, CA, USA) using a Gibson Assembly Cloning Kit (New England Biolabs, Ipswich, MA, USA). Small alterations in these constructs (e.g. modifications at the N-terminus or linker sequence, single amino acid substitutions) were introduced using dedicated primers and Gibson assembly. All plasmids were grown using E. coli strain DH5a and purified using a Macherey-Nagel (Dueren, Germany) Endotoxin-Free (EF) plasmid purification kit.
Cell Lines B16-F10, a melanoma cell line of C57BL/6 origin, was maintained in culture medium consisting of IMDM (ThermoFisher-Gibco, Waltham, MA, USA) supplemented with 8% fetal calf serum (Sigma-Aldrich, Zwijndrecht, the Netherlands) in the presence of L-glutamine, penicillin and streptomycin (all from ThermoFisher-Gibco) in a humidified CO2-incubator (37° C., 5% CO2). 293, an epithelial cell line derived from human embryonic kidney cell (ATCC CRL-1573), was cultured under the same conditions.
Transfections B16-F10 cells (2,000 cells/well) or 293 cells (20,000 cells/well) were plated in a 96-well flat bottom plate in 100 μl culture medium. One day later, they were transfected by the addition of 10 μl (20-40 ng) DNA complexed with Saint-DNA (Synvolux products, Leiden, the Netherlands), a cationic lipid-based transfection reagent. Two days after transfection, cell death and/or the release of DAMPS were analysed by LDH assays or ELISA.
IL-1β ELISA To measure IL-1β, cellular supernatants were centrifuged to remove cell debris and analysed by sandwich ELISA, using protocols provided by the supplier (Biolegend, San Diego, CA). Briefly, 96-well plates were coated with capture antibody overnight. After washing away unbound antibody (4 washing steps), 50-1000-fold diluted supernatant was added (and, for reference, titrated recombinant IL-1β) was added and incubated for 2 h at room temperature while shaking. After 4 washing steps, biotinylated detection antibody was added and incubated for 1 h at RT, followed by another 4 wash steps and a 30-minute incubation with streptavidin-HRP. After washing away strep-HRP, TMB substrate solution was added. Absorbance at 450 nm and 570 nm was read on a Tecan Infinite F50 (Tecan Group Ltd, Männedorf, Switzerland).
LDH Assay The LDH-Glo Cytotoxicity assay (Promega, Madison, WI, USA) was used to measure LDH activity in culture supernatants. In this assay, LDH released from damaged cells catalyzes the oxidation of lactate with concomitant reduction of NAD+ to NADH. Reductase uses NADH and reductase substrate to generate luciferin, which is converted to a bioluminescent signal by Ultra-Glo™ rLuciferase. The luminescent signal generated is proportional to the amount of LDH present. Briefly, 10 ul culture supernatant was diluted with 90 ul LDH storage buffer (200 mM Tris-HCl (pH 7.3), 10% Glycerol, 1% BSA). After another 10-fold dilution in LDH storage buffer, 50 ul 100-fold diluted supernatant was mixed with 50 ul LDH Detection Reagent and incubated at room temperature in the dark, followed by luminescence readings at 30 and 60 minutes on a Tecan Infinite F50 (Tecan Group Ltd, Männedorf, Switzerland). Data were represented as Relative Light Units (RLU).
Results
Murine CASP1_RV2 Functionality Depends on Presence N-Terminal IDL Sequence Our initial design of the constitutively active murine inflammatory caspase-1 (CASP1_RV, SEQ ID NO: 3) was led by the design of constitutively active versions of human apoptosis-inducing human executioner caspase-3 and -6 (Srinivasula et al., 1998. J Biol Chem 273: 10107-11). In the design of active caspase-3, for example, the N-terminal p20 and C-terminal p10 domains were swapped and separated by a short (8 AA) caspase-3 cleavage site. A part of the sequence upstream of p10, including several p20 amino acids, was also moved by this swap, the N-terminus of resulting active caspase began with four p20 amino acids, followed by the small (6 AA) p20-p10 interdomain linker and p10 (Srinivasula et al., 1998. J Biol Chem 273: 10107-11). Accordingly, the N-terminus of murine CASP1_RV began with five p20 amino acids and the IDL. As removal of the p20 remnant in CASP1_RV2 (SEQ ID NO: 4) appeared to increase activity compared to CASP1_RV (SEQ ID: 3, FIGS. 2-3), we tested an additional variant CASP1_RV2_NTR (SEQ ID NO: 38) lacking the IDL altogether. Testing these three CASP1_RV variants progressively lacking more of this N-terminus showed that removal of the N-terminal p20 remnant in CASP1_RV2 increased, but further removal of the IDL in CASP1_RV2_NTR decreased the activity of CASP1_RV (FIG. 6). In other words, the most active CASP1_RV2 variant retained most of the, highly negatively charged, IDL sequence SEEDFLTDAIFEDD at its N-terminus. Compared to wild-type murine caspase-1 (CASP1_WT), CASP1_RV2 was approximately 30-fold more potent in in vitro assays (FIG. 7). Thus, despite crucial differences between human caspase-3 and mouse caspase-1, such as the presence of a CARD domain in caspase-1 and a difference in activation mechanism, the Srinivasula-approach indeed generated constitutively active mouse caspase-1.
Human CASP1_RV2 Functionality Relies on Absence N-Terminal IDL Sequence The design of a constitutively active human caspase-1 variant (hCASP1_RV2, SEQ ID NO: 35) was based on murine CASP1_RV2, and therefore also began with 14 amino acids of the interdomain linker (IDL): GNLSLPTTEEFEDD. However, hCASP1_RV2 was not significantly more active than wild-type human caspase-1 (hCASP1_WT, FIG. 8). Thus, in contrast with mouse caspase-1, following the Srinivasula-approach did not significantly increase the activity of human caspase-1. Surprisingly, in striking contrast with murine CASP1_RV2 (FIG. 6) and despite its distance from the enzymatically active site (Yang et al., 2018. Proc Natl Acad Sci USA 115: 6792-6797), removing all N-terminal residues upstream of p10 (hCASP1_RV2_NTR, SEQ ID NO: 49) did greatly increase its activity (FIG. 8).

Reduction of p10-p20 Linker Size Further Increases Constitutively Active Human Caspase-1 Potency Next, we turned our attention to the intervening sequence between p10 and p20. Removing aspartic acid protease sites in this region of mouse and human CASP1_RV2 [SEQ ID NOs 40-43, 45-47] did not significantly affect their ability to process pro-IL1β, suggesting that autoproteolysis did not contribute to its activity (data not shown). Rather, this region appeared to serve merely as a flexible linker. Crystal structures of caspase-1 in its active conformation (Yang et al., 2018. Proc Natl Acad Sci USA 115: 6792-6797) indicated that the distance between the C-terminus of the p10 domain and the N-terminus of the p20 domain is rather small (FIG. 9). In fact, we discovered that reducing the size of the linker to 9 amino acids was not a neutral event, as we had expected, but surprisingly increased the activity of hCASP1_NTR (FIG. 8B). This was independent of the presence (AYVHDAPVR in hCASP1_NTR_CCS, SEQ ID NO: 51) or absence (GSGSGSGSG in hCASP1_NTR_GSL, SEQ ID NO:50) of an autoproteolytic target site in this smaller linker (FIG. 8B). Compared to wild-type human caspase-1, hCASP1_NTR_GSL (SEQ ID NO:50) was approximately 30-fold more potent in in vitro assays (FIG. 8). Thus, while the Srinivasula-approach did not significantly increase the activity of human caspase-1, removing N-terminal residues and, to a lesser extent, reducing linker size unexpectedly did yield a constitutively active human caspase-1.

TABLE 1

Pyroptosis-associated constructs. For a detailed description of caspase-1 constructs, see FIG. 1.

| Gene name | Construct | Modification | SEQ ID NO |
|---|---|---|---|
| *Mus musculus* | | | |
| Pycard | dCARD | ASC CARD domain + 2 C-terminal dimerisation domains | 31 |
| Casp 1 | CASP1_C285G | active site mutant | 2 |
| | CASP1_WT | wild-type (wt) | 1 |
| | CASP1_RV | p10 and p20 domain reversal | 3 |
| | CASP1_RV2 | p10 and p20 domain reversal | 4 |
| | dCASP1 | wt + 2 N-terminal dimerisation domains | 12 |
| | iCASP1 | wt + 2 N-terminal AP1903-inducible dimerisation domains | 8 |
| Gsdmdc1 | GSDMD_WT_FLAG | wild-type (+FLAG) | 32 |
| | GSDMD_NTER | N-terminal fragment | 14 |
| | GSDMD_NTER_FLAG | N-terminal fragment (+FLAG) | 15 |
| Il1b | IL1B_WT | mature IL-1β (IFNβ signal peptide) | 17 |
| | IL1B_FL | wild-type pro-IL1β | 21 |
| | IL1B_CALRSP | mature IL-1β (Calreticulin signal peptide) | 33 |
| Il18 | IL18_WT | mature IL-18 (IFNβ signal peptide) | 34 |
| *Homo sapiens* | | | |
| CASP1 | hCASP1_RV2 | human version CASP1_RV2 | 35 |
| IL1B | hIL1B_SP | human mature IL-1β (IFNβ SP) | 36 |
| | hIL1B_FL | human wild-type pro-IL1β | 37 |

TABLE 2

Amino acid sequences.

| SEQ ID NO | Gene | Construct | AA sequence |
|---|---|---|---|
| 1 | Casp1 | CASP1_WT | MADKILRAKRKQFINSVSIGTINGLLDELLEKRVLNQEEMDKIKLANITAMDKARDLCDHVSKKGPQASQIFITYICN EDCYLAGILELQSAPSAETFVATEDSKGGHPSSSETKEEQNKEDGTFPGLTGTLKFCPLEKAQKLWKENPSEIYPIMN TTTRTRLALIICNTEFQHLSPRVGAQVDLREMKLLLEDLGYTVKVKENLTALEMVKEVKEFAACPEHKTSDSTFLVFM SHGIQEGICGTTYSNEVSDILKVDTIFQMMNTLKCPSLKDKPKVIIIQACRGEKQGVVLLKDSVRDSEEDFLTDAIFE DDGIKKAHIEKDFIAFCSSTPDNVSWRHPVRGSLFIESLIKHMKEYAWSCDLEDIFRKVRFSFEQPEFRLQMPTADRV TLTKRFYLFPGH |
| 2 | Casp1 | CASP1_C285G | MADKILRAKRKQFINSVSIGTINGLLDELLEKRVLNQEEMDKIKLANITAMDKARDLCDHVSKKGPQASQIFITYICN EDCYLAGILELQSAPSAETFVATEDSKGGHPSSSETKEEQNKEDGTFPGLTGTLKFCPLEKAQKLWKENPSEIYPIMN TTTRTRLALIICNTEFQHLSPRVGAQVDLREMKLLLEDLGYTVKVKENLTALEMVKEVKEFAACPEHKTSDSTFLVFM SHGIQEGICGTTYSNEVSDILKVDTIFQMMNTLKCPSLKDKPKVIIIQAGRGEKQGVVLLKDSVRDSEEDFLTDAIFE DDGIKKAHIEKDFIAFCSSTPDNVSWRHPVRGSLFIESLIKHMKEYAWSCDLEDIFRKVRFSFEQPEFRLQMPTADRV TLTKRFYLFPGH |
| 3 | Casp1 | CASP1_RV | MVLLKDSVRDSEEDFLTDAIFEDDGIKKAHIEKDFIAFCSSTPDNVSWRHPVRGSLFIESLIKHMKEYAWSCDLEDIF RKVRFSFEQPEFRLQMPTADRVTLTKRFYLFPGHLLVCDVPIRAPSAETFVATEDSKGGHPSSSETKEEQNKEDGTFP GLTGTLKFCPLEKAQKLWKENPSEIYPIMNTTTRTRLALIICNTEFQHLSPRVGAQVDLREMKLLLEDLGYTVKVKEN LTALEMVKEVKEFAACPEHKTSDSTFLVFMSHGIQEGICGTTYSNEVSDILKVDTIFQMMNTLKCPSLKDKPKVIIIQ ACRGEKQGVVLLKD |
| 4 | Casp1 | CASP1_RV2 | MSEEDFLTDAIFEDDGIKKAHIEKDFIAFCSSTPDNVSWRHPVRGSLFIESLIKHMKEYAWSCDLEDIFRKVRFSFEQ PEFRLQMPTADRVTLTKRFYLFPGHLLVCDVPIRAPSAETFVATEDSKGGHPSSSETKEEQNKEDGTFPGLTGTLKFC PLEKAQKLWKENPSEIYPIMNTTTRTRLALIICNTEFQHLSPRVGAQVDLREMKLLLEDLGYTVKVKENLTALEMVKE VKEFAACPEHKTSDSTFLVFMSHGIQEGICGTTYSNEVSDILKVDTIFQMMNTLKCPSLKDKPKVIIIQACRGEKQGV VLLKD |

TABLE 2-continued

Amino acid sequences.

| SEQ ID NO | Gene | Construct | AA sequence |
|---|---|---|---|
| 5 | Casp1 | S, p10 (AA315-402) | GIKKAH IEKDFIAFCS STPDNVSWRH PVRGSLFIES LIKHMKEYAW SCDLEDIFRK VRFSFEQPEF RLQMPTADRV TLTKRFYLFP GH |
| 6 | Casp1 | CARD-L linker (AA92-118) | APSAETFVA TEDSKGGHPS SSETKEEQ |
| 7 | Il1b | Il1b caspase-1 cleavage site | LLVCDVPIR |
| 8 | Casp1 | iCASP1 | MGSRGVQVETISPGDGRTFPKRGQTCVVHYTGMLEDGKKVDSSRDRNKPFKFMLGKQEVIRGWEEGVAQMSVGQRAKL TISPDYAYGATGHPGIIPPHATLVFDVELLKLETRGVQVETISPGDGRTFPKRGQTCVVHYTGMLEDGKKVDSSRDRN KPFKFMLGKQEVIRGWEEGVAQMSVGQRAKLTISPDYAYGATGHPGIIPPHATLVFDVELLKLESGGGSAPSAETFVA TEDSKGGHPSSSETKEEQNKEDGTFPGLTGTLKFCPLEKAQKLWKENPSEIYPIMNTTTRTRLALIICNTEFQHLSPR VGAQVDLREMKLLLEDLGYTVKVKENLTALEMVKEVKEFAACPEHKTSDSTFLVFMSHGIQEGICGTTYSNEVSDILK VDTIFQMMNTLKCPSLKDKPKVIIIQACRGEKQGVVLLKDSVRDSEEDFLTDAIFEDDGIKKAHIEKDFIAFCSSTPD NVSWRHPVRGSLFIESLIKHMKEYAWSCDLEDIFRKVRFSFEQPEFRLQMPTADRVTLTKRFYLFPGH |
| 9 | n.a. | SGGGS linker | SGGGS |
| 10 | n.a. | F36V-FKBP | MGSRGVQVET ISPGDGRTFP KRGQTCVVHY TGMLEDGKKV DSSRDRNKPF KFMLGKQEVI RGWEEGVAQM SVGQRAKLTI SPDYAYGATG HPGIIPPHAT LVFDVELLKL ETRGVQVETI SPGDGRTFPK RGQTCVVHYT GMLEDGKKVD SSRDRNKPFK FMLGKQEVIR GWEEGVAQMS VGQRAKLTIS PDYAYGATGH PGIIPPHATL VFDVELLKLE |
| 11 | n.a. | F36M-FKBP | MGVQVET ISPGDGRTFP KRGQTCVVHY TGMLEDGKKM DSSRDRNKPF KFMLGKQEVI RGWEEGVAQM SVGQRAKLTI SPDYAYGATG HPGIIPPHAT LVFDVELLKL ETRGVQVETI SPGDGRTFPK RGQTCVVHYT GMLEDGKKMD SSRDRNKPFK FMLGKQEVIR GWEEGVAQMS VGQRAKLTIS PDYAYGATGH PGIIPPHATL VFDVELLKLE |
| 12 | Casp1 | dCASP1 | MGVQVETISPGDGRTFPKRGQTCVVHYTGMLEDGKKMDSSRDRNKPFKFMLGKQEVIRGWEEGVAQMSVGQRAKLTIS PDYAYGATGHPGIIPPHATLVFDVELLKLETRGVQVETISPGDGRTFPKRGQTCVVHYTGMLEDGKKMDSSRDRNKPF KFMLGKQEVIRGWEEGVAQMSVGQRAKLTISPDYAYGATGHPGIIPPHATLVFDVELLKLESGGGSAPSAETFVATED SKGGHPSSSETKEEQNKEDGTFPGLTGTLKFCPLEKAQKLWKENPSETYPIMNTTTRTRLALIICNTEFQHLSPRVGA QVDLREMKLLLEDLGYTVKVKENLTALEMVKEVKEFAACPEHKTSDSTFLVFMSHGIQEGICGTTYSNEVSDILKVDT IFQMMNTLKCPSLKDKPKVIIIQACRGEKQGVVLLKDSVRDSEEDFLTDAIFEDDGIKKAHIEKDFIAFCSSTPDNVS WRHPVRGSLFIESLIKHMKEYAWSCDLEDIFRKVRFSFEQPEFRLQMPTADRVTLTKRFYLFPGH |
| 13 | n.a. | dasher GFP | MTALTEGAKLFEKEIPYITELEGDVEGMKFIIKGEGTGDATTGTIKAKYICTTGDLPVPWATLVSTLSYGVQCFAKYP SHIKDFFKSAMPEGYTQERTISFEGDGVYKTRAMVTYERGSIYNRVTLTGENFKKDGHILRKNVAFQCPPSILYILPD TVNNGIRVEFNQAYDIEGVTEKLVTKCSQMNRPLAGSAAVHIPRYHHITYHTKLSKDRDERRDHMCLVEVVKAVDLDT YQ |
| 14 | Gsdmdc1 | GSDMD_NTER | MPSAFEKVVKNVIKEVSGSRGDLIPVDSLRNSTSFRPYCLLNRKFSSSRFWKPRYSCVNLSIKDILEPSAPEPEPECF GSFKVSDVVDGNIQGRVMLSGMGEGKISGGAAVSDSSSASMNVCILRVTQKTWETMQHERHLQQPENKILQQLRSRGD DLFVVTEVLQTKEEVQITEVHSQEGSGQFTLPGALCLKGEGKGHQSRKKMVTIPAGSILAFRVAQLLIGSKWDILLVS DEKQRTFEPSSGDRKAVGQRHHGLNVLAALCSIGKQLSLLSD |
| 15 | Gsdmdc1 | GSDMD_NTER_FLAG | MPSAFEKVVKNVIKEVSGSRGDLIPVDSLRNSTSFRPYCLLNRKFSSSRFWKPRYSCVNLSIKDILEPSAPEPEPECF GSFKVSDVVDGNIQGRVMLSGMGEGKISGGAAVSDSSSASMNVCILRVTQKTWETMQHERHLQQPENKILQQLRSRGD DLFVVTEVLQTKEEVQITEVHSQEGSGQFTLPGALCLKGEGKGHQSRKKMVTIPAGSILAFRVAQLLIGSKWDILLVS DEKQRTFEPSSGDRKAVGQRHHGLNVLAALCSIGKQLSLLSDDYKDDDK |
| 16 | Mlkl | MLKL_FLAG_MT | MDKLGQIIKLGQLIYEQCEKMKYCRKQCQRLGNRVHGLLQPLQRLQAQGKKNLPDDITAALGRFDEVLKEANQQIEKF SKKSHIWKPVSVGNDKILFHEVNEKLRDVWEELLLLLQVYHWNTVSDVSQPASWQQDERDQAEEDGNENMKVILMQLQ ISVEEINKTLKQCSLKPTQEIPQDLQTIKEIPKEHLGPPWTKLKTSKMSTIYRGEYHRSPVTIKVFNNPQAESVGIVRF TFNDEIKTMKKFDSPNILRIFGICIDQTVKPPEFSIVMEYCELGTLRELLDREKDLTMSVRSLLVLRAARGLYRLHHS ETLHRNISSSSFLVAGGYQVKLAGFELSKTANSISRTAKSTKAERSSSTIYVSPERLKNPFCLYDIKAEIYSFGIVLW EIATGKIPFEGCDSKKIRELVAEDKKQEPVGQDCPELLREIINECRAHEPSQRPSVDGILERLSAVEESTDKKVDYKD DDDK |
| 17 | Il1b | IL1B_WT | MNNRWILHAAFLLCFSTTALSVPIRQLHYRLRDEQQKSLVLSDPYELKALHLNGQNINQQVIFSMSFVQGEPSNDKIP VALGLKGKNLYLSCVMKDGTPTLQLESVDPKQYPKKKMEKRFVFNKIEVKSKVEFESAEFPNWYISTSQAEHKPVFLG NNSGQDIIDFTMESVSS |
| 18 | Ifnb | IFNB_WT | MNNRWILHAAFLLCFSTTALSINYKQLQLQERTNIRKCQELLEQLNGKINLTYRADFKIPMEMTEKMQKSYTAFAIQE MLQNVFLVFRNNFSSTGWNETIVVRLLDELHQQTVFLKTVLEEKQEERTWEMSSTALHLKSYYWRVQRYLKLMKYNS YAWMVVRAEIFRNFLIIRRLTRNFQN |

TABLE 2-continued

Amino acid sequences.

| SEQ ID NO | Gene | Construct | AA sequence |
|---|---|---|---|
| 19 | Ddx58 | FLAG_RIGI_NTER | MDYKDDDDKTAEQRQNLQAFRDYIKKILDPTYILSYMSSWLEDEEVQYIQAEKNNKGPMEAASLFLQYLLKLQSEGWF QAFLDALYHAGYCGLCEAIESWDFQKIEKLEEHRLLLRRLEPEFKATVDPNDILSELSECLINQECEEIRQIRDTKGR MAGAEKMAECLIRSDKENWPKVLQLALEKDNSKFSELWIVDKGFKRAESKADEDDGAEASSIQIFIQEEPECQNLSQN PGPPSEASSNNLHSPLKPRNYQLELALPAKKGKNTIICAPTGCGKTFVSLLICEHHLK |
| 20 | Reps1 | Reps1 | MKKVVVNGRVLELFRAAQLANDVVLQIMELCGATRLGYFGR |
| 21 | Il1b | IL1B_FL | MATVPELNCEMPPFDSDENDLFFEVDGPQKMKGCFQTFDLGCPDESIQLQISQQHINKSFRQAVSLIVAVEKLWQLPV SFPWTFQDEDMSTFFSFIFEEEPILCDSWDDDDNLLVCDVPIRQLHYRLRDEQQKSLVLSDPYELKAHLNGQNINQQ VIFSMSFVQGEPSNDKIPVALGLKGKNLYLSCVMKDGTPTLQLESVDPKQYPKKKMEKRFVFNKIEVKSKVEFESAEF PNWYISTSQAEHKPVFLGNNSGQDIIDFTMESVSS |
| 22 | Il1b | IL1B_WT | MNNRWILHAAFLLCFSTTALSVPIRQLHYRLRDEQQKSLVLSDPYELKAHLNGQNINQQVIFSMSFVQGEPSNDKIP VALGLKGKNLYLSCVMKDGTPTLQLESVDPKQYPKKKMEKRFVFNKIEVKSKVEFESAEFPNWYISTSQAEHKPVFLG NNSGQDIIDFTMESVSS |
| 23 | n.a. | polyepitope vaccine | MAEAGQSLVISASIIVFNLLELEGDYRDDHIFSLYFMAAAKVVVNGRVLELFRAAQLANDVVLQIMELCGATRLGAAA DIPTGIPVHLELASMTNMELMSSIVHQQVFPTVASAAAGISSAESLKISQAVHAAHAEINEAGREVVGSAEAGAAALL PDEVSGLEQLESIINFEKLTEWTSSNVMEERKI |
| 24 | Csf2 | CSF2 | MWLQNLLFLGIVVYSLSAPTRSPITVTRPWKHVEAIKEALNLLDDMPVTLNEEVEVVSNEFSFKKLTCVQTRLKIFEQ GLRGNFTKLKGALNMTASYYQTYCPPTPETDCETQVTTYADFIDSLKTFLTDIPFECKKPGQK |
| 25 | Dpagt1 | Dpagt1 | EAGQSLVISASIIVFNLLELEGDYRDDHIFSLYFM |
| 26 | Reps1 | Reps1 | KVVVNGRVLELFRAAQLANDVVLQIMELCGATRLG |
| 27 | Adpgk | Adpgk | DIPTGIPVHLELASMTNMELMSSIVHQQVFPTVAS |
| 28 | n.a. | OT-II | GISSAESLKISQAVHAAHAEINEAGREVVGSAEAG |
| 29 | n.a. | OT-I | LLPDEVSGLEQLESIINFEKLTEWTSSNVMEERKI |
| 30 | n.a. | spacer | AAA |
| 31 | Pycard | dCARD | MGSTARTGHFVDQHRQALIARVTEVDGVLDALHGSVLTEGQYQAVRAETTSQDKMRKLFSFVPSWNLTCKDSLLQALK EIHPYLVMDLEQSGGGGSGVQVETISPGDGRTFPKRGQTCVVHYTGMLEDGKKMDSSRDRNKPFKFMLGKQEVIRGWE EGVAQMSVGQRAKLTISPDYAYGATGHPGIIPPHATLVFDVELLKLETRGVQVETISPGDGRTFPKRGQTCVVHYTGM LEDGKKMDSSRDRNKPFKFMLGKQEVIRGWEEGVAQMSVGQRAKLTISPDYAYGATGHPGIIPPHATLVFDVELLKLE |
| 32 | Gsdmdc1 | GSDMD_WT_FLAG | MPSAFEKVVKNVIKEVSGSRGDLIPVDSLRNSTSFRPYCLLNRKFSSSRFWKPRYSCVNLSIKDILEPSAPEPEPECF GSFKVSDVVDGNIQGRVMLSGMGEGKISGGAAVSDSSSASMNVCILRVTQKTWETMQHERHLQQPENKILQQLRSRGD DLFVVTEVLQTKEEVQITEVHSQEGSGQFTLPGALCLKGEGKGHQSRKKMVTIPAGSILAFRVAQLLIGSKWDILLVS DEKQRTFEPSSGDRKAVGQRHHGLNVLAALCSIGKQLSLLSDGIDEEELIEAADFQGLYAEVKACSSELESLEMELRQ QILVNIGKILQDQPSMEALEASLGQGLCSGGQVEPLDGPAGCILECLVLDSGELVPELAAPIFYLLGALAVLSETQQQ LLAKALETTVLSKQLELVKHVLEQSTPWQEQSSVSLPTVLLGDCWDEKNPTWVLLEECGLRLQVESPQVHWEPTSLIP TSALYASLFLLSSLGQKPCDYKDDDDK |
| 33 | IL1b | IL1B_CALRSP | MGLLSVPLLLGLLGLAAADPAVPIRQLHYRLRDEQQKSLVLSDPYELKAHLNGQNINQQVIFSMSFVQGEPSNDKIP VALGLKGKNLYLSCVMKDGTPTLQLESVDPKQYPKKKMEKRFVFNKIEVKSKVEFESAEFPNWYISTSQAEHKPVFLG NNSGQDIIDFTMESVSS |
| 34 | IL1b | IL18_WT | MNNRWILHAAFLLCFSTTALSNFGRLHCTTAVIRNINDQVLFVDKRQPVFEDMTDIDQSASEPQTRLIIYMYKDSEVR GLAVTLSVKDSKMSTLSCKNKIISFEEMDPPENIDDIQSDLIFFQKRVPGHNKMEFESSLYEGHFLACQKEDDAFKLI LKKKDENGDKSVMFTLTNLHQS |
| 35 | CASP1 | hCASP_RV2 | MGNLSLPTTEEFEDDAIKKAHIEKDFIAFCSSTPDNVSWRHPTMGSVFIGRLIEHMQEYACSCDVEEIFRKVRFSFEQ PDGRAQMPTTERVTLTRCFYLFPGHAYVHDAPVRDQTSGNYLNMQDSQGVLSSFPAPQAVQDNPAMPTSSGSEGNVKL CSLEEAQRIWKQKSAEIYPIMDKSSRTRLALIICNEEFDSIPRRTGAEVDITGMTMLLQNLGYSVDVKKNLTASDMTT ELEAFAHRPEHKTSDSTFLVFMSHGIREGICGKKHSEQVPDILQLNAIFNMLNTKNCPSLKDKPKVIIIQACRGDSPG VVWFKD |
| 36 | IL1B | hIL1B_SP | MTNKCLLQIALLLCFSTTALSAPVRSLNCTLRDSQQKSLVMSGPYELKAHLQGQDMEQQVVFSMSFVQGEESNDKIP VALGLKEKNLYLSCVLKDDKPTLQLESVDPKNYPKKKMEKRFVFNKIEINNKLEFESAQFPNWYISTSQAENMPVFLG GTKGGQDITDFTMQFVSS |
| 37 | IL1B | hIL1B_FL | MAEVPKLASEMMAYYSGNEDDLFFEADGPKQMKCSFQDLDLCPLDGGIQLRISDHHYSKGFRQAASVVVAMDKLRKML VPCPQTFQENDLSTFFPFIFEEEPIFFDTWDNEAYVHDAPVRSLNCTLRDSQQKSLVMSGPYELKAHLQGQDMEQQV VFSMSFVQGEESNDKIPVALGLKEKNLYLSCVLKDDKPTLQLESVDPKNYPKKKMEKRFVFNKIEINNKLEFESAQFP NWYISTSQAENMPVFLGGTKGGQDITDFTMQFVSS |

TABLE 2-continued

Amino acid sequences.

| SEQ ID NO | Gene | Construct | AA sequence |
|---|---|---|---|
| 38 | Casp1 | CASP1_RV2_NTR | MGIKKAHIEKDFIAFCSSTPDNVSWRHPVRGSLFIESLIKHMKEYAWSCDLEDIFRKVRFSFEQPEFRLQMPTADRVTLTKRFYLFPGHLLVCDVPTRAPSAETFVATEDSKGGHPSSSETKEEQNKEDGTFPGLTGTLKFCPLEKAQKLWKENPSEIYPIMNTTTRTRLALIICNTEFQHLSPRVGAQVDLREMKLLLEDLGYTVKVKENLTALEMVKEVKEFAACPEHKTSDSTFLVFMSHGIQEGICGTTYSNEVSDILKVDTIFQMMNTLKCPSLKDKPKVIIIQACRGEKQGVVLLKD |
| 39 | Casp1 | CASP1_RV2_C305G | MSEEDFLTDAIFEDDGIKKAHIEKDFIAFCSSTPDNVSWRHPVRGSLFIESLIKHMKEYAWSCDLEDIFRKVRFSFEQPEFRLQMPTADRVTLTKRFYLFPGHLLVCDVPTRAPSAETFVATEDSKGGHPSSSETKEEQNKEDGTFPGLTGTLKFCPLEKAQKLWKENPSEIYPIMNTTTRTRLALIICNTEFQHLSPRVGAQVDLREMKLLLEDLGYTVKVKENLTALEMVKEVKEFAACPEHKTSDSTFLVFMSHGIQEGICGTTYSNEVSDILKVDTIFQMMNTLKCPSLKDKPKVIIIQAGRGEKQGVVLLKD |
| 40 | Casp1 | CASP1_RV2_D108A | MSEEDFLTDAIFEDDGIKKAHIEKDFIAFCSSTPDNVSWRHPVRGSLFIESLIKHMKEYAWSCDLEDIFRKVRFSFEQPEFRLQMPTADRVTLTKRFYLFPGHLLVCAVPTRAPSAETFVATEDSKGGHPSSSETKEEQNKEDGTFPGLTGTLKFCPLEKAQKLWKENPSEIYPIMNTTTRTRLALIICNTEFQHLSPRVGAQVDLREMKLLLEDLGYTVKVKENLTALEMVKEVKEFAACPEHKTSDSTFLVFMSHGIQEGICGTTYSNEVSDILKVDTIFQMMNTLKCPSLKDKPKVIIIQACRGEKQGVVLLKD |
| 41 | Casp1 | CASP1_RV2_D124A | MSEEDFLTDAIFEDDGIKKAHIEKDFIAFCSSTPDNVSWRHPVRGSLFIESLIKHMKEYAWSCDLEDIFRKVRFSFEQPEFRLQMPTADRVTLTKRFYLFPGHLLVCDVPTRAPSAETFVATEASKGGHPSSSETKEEQNKEDGTFPGLTGTLKFCPLEKAQKLWKENPSEIYPIMNTTTRTRLALIICNTEFQHLSPRVGAQVDLREMKLLLEDLGYTVKVKENLTALEMVKEVKEFAACPEHKTSDSTFLVFMSHGIQEGICGTTYSNEVSDILKVDTIFQMMNTLKCPSLKDKPKVIIIQACRGEKQGVVLLKD |
| 42 | Casp1 | CASP1_RV2_D143A | MSEEDFLTDAIFEDDGIKKAHIEKDFIAFCSSTPDNVSWRHPVRGSLFIESLIKHMKEYAWSCDLEDIFRKVRFSFEQPEFRLQMPTADRVTLTKRFYLFPGHLLVCDVPTRAPSAETFVATEDSKGGHPSSSETKEEQNKEAGTFPGLTGTLKFCPLEKAQKLWKENPSEIYPIMNTTTRTRLALIICNTEFQHLSPRVGAQVDLREMKLLLEDLGYTVKVKENLTALEMVKEVKEFAACPEHKTSDSTFLVFMSHGIQEGICGTTYSNEVSDILKVDTIFQMMNTLKCPSLKDKPKVIIIQACRGEKQGVVLLKD |
| 43 | Casp1 | CASP1_RV2_D108A_D124A_D143A | MSEEDFLTDAIFEDDGIKKAHIEKDFIAFCSSTPDNVSWRHPVRGSLFIESLIKHMKEYAWSCDLEDIFRKVRFSFEQPEFRLQMPTADRVTLTKRFYLFPGHLLVCAVPTRAPSAETFVATEASKGGHPSSSETKEEQNKEAGTFPGLTGTLKFCPLEKAQKLWKENPSEIYPIMNTTTRTRLALIICNTEFQHLSPRVGAQVDLREMKLLLEDLGYTVKVKENLTALEMVKEVKEFAACPEHKTSDSTFLVFMSHGIQEGICGTTYSNEVSDILKVDTIFQMMNTLKCPSLKDKPKVIIIQACRGEKQGVVLLKD |
| 44 | CASP1 | hCASP1_RV2_C306G | MGNLSLPTTEEFEDDAIKKAHIEKDFIAFCSSTPDNVSWRHPTMGSVFIGRLIEHMQEYACSCDVEEIFRKVRFSFEQPDGRAQMPTTERVTLTRCFYLFPGHAYVHDAPVRDQTSGNYLNMQDSQGVLSSFPAPQAVQDNPAMPTSSGSEGNVKLCSLEEAQRIWKQKSAEIYPIMDKSSRTRLALIICNEEFDSIPRRTGAEVDITGMTMLLQNLGYSVDVKKNLTASDMTTELEAFAHRPEHKTSDSTFLVFMSHGIREGICGKKHSEQVPDILQLNAIFNMLNTKNCPSLKDKPKVIIIQAGRGDSPGVVWFKD |
| 45 | CASP1 | hCASP1_RV2_D108A | MGNLSLPTTEEFEDDAIKKAHIEKDFIAFCSSTPDNVSWRHPTMGSVFIGRLIEHMQEYACSCDVEEIFRKVRFSFEQPDGRAQMPTTERVTLTRCFYLFPGHAYVHAAPVRDQTSGNYLNMQDSQGVLSSFPAPQAVQDNPAMPTSSGSEGNVKLCSLEEAQRIWKQKSAEIYPIMDKSSRTRLALIICNEEFDSIPRRTGAEVDITGMTMLLQNLGYSVDVKKNLTASDMTTELEAFAHRPEHKTSDSTFLVFMSHGIREGICGKKHSEQVPDILQLNAIFNMLNTKNCPSLKDKPKVIIIQACRGDSPGVVWFKD |
| 46 | CASP1 | hCASP1_RV2_D140A | MGNLSLPTTEEFEDDAIKKAHIEKDFIAFCSSTPDNVSWRHPTMGSVFIGRLIEHMQEYACSCDVEEIFRKVRFSFEQPDGRAQMPTTERVTLTRCFYLFPGHAYVHDAPVRDQTSGNYLNMQDSQGVLSSFPAPQAVQANPAMPTSSGSEGNVKLCSLEEAQRIWKQKSAEIYPIMDKSSRTRLALIICNEEFDSIPRRTGAEVDITGMTMLLQNLGYSVDVKKNLTASDMTTELEAFAHRPEHKTSDSTFLVFMSHGIREGICGKKHSEQVPDILQLNAIFNMLNTKNCPSLKDKPKVIIIQACRGDSPGVVWFKD |
| 47 | CASP1 | hCASP1_RV2_D124A | MGNLSLPTTEEFEDDAIKKAHIEKDFIAFCSSTPDNVSWRHPTMGSVFIGRLIEHMQEYACSCDVEEIFRKVRFSFEQPDGRAQMPTTERVTLTRCFYLFPGHAYVHDAPVRDQTSGNYLNMQASQGVLSSFPAPQAVQDNPAMPTSSGSEGNVKLCSLEEAQRIWKQKSAEIYPIMDKSSRTRLALIICNEEFDSIPRRTGAEVDITGMTMLLQNLGYSVDVKKNLTASDMTTELEAFAHRPEHKTSDSTFLVFMSHGIREGICGKKHSEQVPDILQLNAIFNMLNTKNCPSLKDKPKVIIIQACRGDSPGVVWFKD |
| 48 | CASP1 | hCASP1_RV2_NTR2 | MEEFEDDAIKKAHIEKDFIAFCSSTPDNVSWRHPTMGSVFIGRLIEHMQEYACSCDVEEIFRKVRFSFEQPDGRAQMPTTERVTLTRCFYLFPGHAYVHDAPVRDQTSGNYLNMQDSQGVLSSFPAPQAVQDNPAMPTSSGSEGNVKLCSLEEAQRIWKQKSAEIYPIMDKSSRTRLALIICNEEFDSIPRRTGAEVDITGMTMLLQNLGYSVDVKKNLTASDMTTELEAFAHRPEHKTSDSTFLVFMSHGIREGICGKKHSEQVPDILQLNAIFNMLNTKNCPSLKDKPKVIIIQACRGDSPGVVWFKD |
| 49 | CASP1 | hCASP1_RV2_NTR | MAIKKAHIEKDFIAFCSSTPDNVSWRHPTMGSVFIGRLIEHMQEYACSCDVEEIFRKVRFSFEQPDGRAQMPTTERVTLTRCFYLFPGHAYVHDAPVRDQTSGNYLNMQDSQGVLSSFPAPQAVQDNPAMPTSSGSEGNVKLCSLEEAQRIWKQKSAEIYPIMDKSSRTRLALIICNEEFDSIPRRTGAEVDITGMTMLLQNLGYSVDVKKNLTASDMTTELEAFAHRPEHKTSDSTFLVFMSHGIREGICGKKHSEQVPDILQLNAIFNMLNTKNCPSLKDKPKVIIIQACRGDSPGVVWFKD |
| 50 | CASP1 | hCASP1_RV2_NTR_GSL | MAIKKAHIEKDFIAFCSSTPDNVSWRHPTMGSVFIGRLIEHMQEYACSCDVEEIFRKVRFSFEQPDGRAQMPTTERVTLTRCFYLFPGHGSGSGSGSGNPAMPTSSGSEGNVKLCSLEEAQRIWKQKSAEIYPIMDKSSRTRLALIICNEEFDSIPRRTGAEVDITGMTMLLQNLGYSVDVKKNLTASDMTTELEAFAHRPEHKTSDSTFLVFMSHGIREGICGKKHSEQVPDILQLNAIFNMLNTKNCPSLKDKPKVIIIQACRGDSPGVVWFKD |

TABLE 2-continued

Amino acid sequences.

| SEQ ID NO | Gene | Construct | AA sequence |
|---|---|---|---|
| 51 | CASP1 | hCASP1_RV2_NTR_CCS | MAIKKAHIEKDFIAFCSSTPDNVSWRHPTMGSVFIGRLIEHMQEYACSCDVEEIFRKVRFSFEQPDGRAQMPTTERVT LTRCFYLFPGHAYVHDAPVRNPAMPTSSGSEGNVKLCSLEEAQRIWKQKSAEIYPIMDKSSRTRLALIICNEEFDSIP RRTGAEVDITGMTMLLQNLGYSVDVKKNLTASDMTTELEAFAHRPEHKTSDSTFLVFMSHGIREGICGKKHSEQVPDI LQLNAIFNMLNTKNCPSLKDKPKVIIIQACRGDSPGVVWFKD |
| 52 | CASP1 | hCASP1_WT | MADKVLKEKRKLFIRSMGEGTINGLLDELLQTRVLNKEEMEKVKRENATVMDKTRALIDSVIPKGAQACQICITYICE EDSYLAGTLGLSADQTSGNYLNMQDSQGVLSSFPAPQAVQDNPAMPTSSGSEGNVKLCSLEEAQRIWKQKSAEIYPIM DKSSRTRLALIICNEEFDSIPRRTGAEVDITGMTMLLQNLGYSVDVKKNLTASDMTTELEAFAHRPEHKTSDSTFLVF MSHGIREGICGKKHSEQVPDILQLNAIFNMLNTKNCPSLKDKPKVIIIQACRGDSPGVVWFKDSVGVSGNLSLPTTEE FEDDAIKKAHIEKDFIAFCSSTPDNVSWRHPTMGSVFIGRLIEHMQEYACSCDVEEIFRKVRFSFEQPDGRAQMPTTE RVTLTRCFYLFPGH |
| 53 | GSDMD | hGSDMD_WT_FLAG | MGSAFERVVRRVVQELDHGGEFIPVTSLQSSTGFQPYCLVVRKPSSSWFWKPRYKCVNLSIKDILEPDAAEPDVQRGR SFHFYDAMDGQIQGSVELAAPGQAKIAGGAAVSDSSSTSMNVYSLSVDPNTWQTLLHERHLRQPEHKVLQQLRSRGDN VYVVTEVLQTQKEVEVTRTHKREGSGRFSLPGATCLQGEGQGHLSQKKTVTIPSGSTLAFRVAQLVIDSDLDVLLFPD KKQRTFQPPATGHKRSTSEGAWPQLPSGLSMMRCLHNFLTDGVPAEGAFTEDFQGLRAEVETISKELELLDRELCQLL LEGLEGVLRDQLALRALEEALEQGQSLGPVEPLDGPAGAVLECLVLSSGMLVPELAIPVVYLLGALTMLSETQHKLLA EALESQTLLGPLELVGSLLEQSAPWQERSTMSLPPGLLGNSWGEGAPAWVLLDECGLELGEDTPHVCWEPQAQGRMCA LYASLALLSGLSQEPHDYKDDDDK |
| 54 | CASP1 | hCASP1_CARD | MADKVLKEKRKLFIRSMGEGTINGLLDELLQTRVLNKEEMEKVKRENATVMDKTRALIDSVIPKGAQACQICITYICE EDSYLAGTLGLSAD |
| 55 | CASP1 | hCASP1_CDL | QTSGNYLNMQDSQGVLSSFPAPQAVQD |
| 56 | CASP1 | hCASP1_p20 | NPAMPTSSGSEGNVKLCSLEEAQRIWKQKSAEIYPIMDKSSRTRLALIICNEEFDSIPRRTGAEVDITGMTMLLQNLG YSVDVKKNLTASDMITELEAFAHRPEHKTSDSTFLVFMSHGIREGICGKKHSEQVPDILQLNAIFNMLNTKNCPSLKD KPKVIIIQACRGDSPGVVWFKD |
| 57 | CASP1 | hCASP1_IDL | SVGVSGNLSLPTTEEFEDD |
| 58 | CASP1 | hCASP1_p10 | AIKKAHIEKDFIAFCSSTPDNVSWRHPTMGSVFIGRLIEHMQEYACSCDVEEIFRKVRFSFEQPDGRAQMPTTERVTL TRCFYLFPGH |

TABLE 3

Overview of co-stimulatory molecules.

| Nr. | Type | Name | Human protein name |
|---|---|---|---|
| 1 | cytokine | CSF1 | Macrophage colony-stimulating factor 1 |
| 2 | cytokine | CSF2 | Granulocyte-macrophage colony-stimulating factor |
| 3 | cytokine | TNF | Tumor necrosis factor |
| 4 | cytokine | IFNβ | Interferon beta |
| 5 | cytokine | IFNγ | Interferon gamma |
| 6 | cytokine | Flt3L | Fms-related tyrosine kinase 3 ligand |
| 7 | cytokine | IL1β | Interleukin-1 beta |
| 8 | cytokine | IL2 | Interleukin-2 |
| 9 | cytokine | IL4 | Interleukin-4 |
| 10 | cytokine | IL6 | Interleukin-6 |
| 11 | cytokine | IL7 | Interleukin-7 |
| 12 | cytokine | IL10 | Interleukin-10 |
| 13 | cytokine | IL12 | Interleukin-12 |
| 14 | cytokine | IL15 | Interleukin-15 |
| 15 | cytokine | IL18 | Interleukin-18 |
| 16 | cytokine | IL21 | Interleukin-21 |
| 17 | cytokine | IL23 | Interleukin-23 |
| 18 | cytokine | IL27 | Interleukin-27 |
| 19 | cytokine | IL35 | Interleukin-35 |
| 20 | chemokine | MIP1α | C-C motif chemokine 3 |
| 21 | chemokine | MIP1β | C-C motif chemokine 4 |
| 22 | chemokine | MIP3α | C-C motif chemokine 20 |
| 23 | chemokine | MIP3β | C-C motif chemokine 19 |
| 24 | chemokine | RANTES | C-C motif chemokine 5 |
| 25 | chemokine | MCP-1 | C-C motif chemokine 2 |
| 26 | chemokine | MCP-2 | C-C motif chemokine 8 |
| 27 | chemokine | MCP-3 | C-C motif chemokine 7 |
| 28 | chemokine | MCP-4 | C-C motif chemokine 13 |
| 29 | chemokine | GCP-2 | C-X-C motif chemokine 6 |
| 30 | chemokine | NAP-2 | Platelet basic protein |
| 31 | chemokine | IL-8 | Interleukin-8 |
| 33 | transmembrane protein (soluble version) | CD40L | CD40 ligand |
| 34 | transmembrane protein (soluble version) | OX40 | Tumor necrosis factor receptor superfamily member 4 |

TABLE 4

Caspase-1 constructs. For a detailed description of caspase-1 constructs, also see FIG. 6.

| Gene name | Construct | Modification | SEQ ID NO |
|---|---|---|---|
| *Mus musculus* | | | |
| Casp 1 | CASP1_RV2_C305G | CASP1_RV2, active site mutant | 39 |
| | CASP1_RV2_NTR | CASP1_RV2, no extension N-terminal to p10 | 38 |
| *Homo sapiens* | | | |
| CASP1 | hCASP1_WT | wild-type (wt) | 52 |
| | hCASP1_RV2_C305G | hCASP1_RV2, active site mutant | 44 |

TABLE 4-continued

Caspase-1 constructs. For a detailed description of caspase-1 constructs, also see FIG. 6.

| Gene name | Construct | Modification | SEQ ID NO |
|---|---|---|---|
| | hCASP1_RV2_NTR2 | hCASP1_RV2, small (6 AA) N-terminal IDL extension | 48 |
| | hCASP1_RV2_NTR | hCASP1_RV2, no N-terminal IDL extension | 49 |
| | hCASP1_RV2_NTR_CCS | hCASP1_RV2_NTR, short p10-p20 linker AYVHDAPVR | 51 |
| | hCASP1_RV2_NTR_GSL | hCASP1_RV2_NTR, short p10-p20 linker GSGSGSGSG | 50 |
| hGSDMD_WT_FLAG | | wild-type, FLAG-tagged | 53 |

The invention claimed is:

1. A constitutively active pro-inflammatory caspase-1, comprising swapped p10 and p20 domains.

2. The constitutively active pro-inflammatory caspase according to claim 1, which lacks a caspase-recruitment domain (CARD).

3. The constitutively active pro-inflammatory caspase according to claim 1, in which a glycine corresponding to G403 (SEQ ID NO:52) is located at a distance from 0 to 40 amino acids residues from a cysteine corresponding to C136 (SEQ ID NO:52).

4. The constitutively active pro-inflammatory caspase according to claim 1, lacking a p20-p10 interdomain linker (IDL).

5. A method of stimulating an immune response in an individual in need thereof, comprising administering said constitutively active pro-inflammatory caspase of claim 1 to the individual.

6. The method according to claim 5, wherein said immune response is directed against a tumour or infection that is present in the individual.

7. The method according to claim 5, wherein said caspase is administered into a tumour of the individual.

8. The method according to claim 5, wherein said caspase is administered systemically as an adjuvant of a vaccine.

9. The method according to claim 5, wherein said caspase is administered in combination with one or more accessory molecules, a further immune stimulating molecule, or a combination thereof.

10. The method according to claim 9, wherein said accessory molecule is selected from the group consisting of macrophage colony-stimulating factor 1, granulocyte-macrophage colony-stimulating factor, tumor necrosis factor, interferon beta, interferon gamma, Fms-related tyrosine kinase 3 ligand, intereukin-1 beta, interleukin-2, interleukin-4, interleukin-6, interleukin-7, interleukin-10, interleukin-12, interleukin-15, interleukin-18, interleukin-21, interleukin-23, interleukin-27, interleukin-35, C—C motif chemokine 3, C—C motif chemokine 4, C—C motif chemokine 20, C—C motif chemokine 19, C—C motif chemokine 5, C—C motif chemokine 2, C—C motif chemokine 8, C—C motif chemokine 7, C—C motif chemokine 13, C—X—C motif chemokine 6, platelet basic protein, interleukin-8, CD40 ligand and tumor necrosis factor receptor superfamily member 4.

11. The method according to claim 9, wherein said accessory molecule is interleukin-12 (IL-12), granulocyte-macrophage colony-stimulating factor (CSF2), or a combination thereof.

12. An immune-stimulating composition, comprising the constitutively active pro-inflammatory caspase according to claim 1 and a pharmacologically acceptable excipient.

13. The immune-stimulating composition according to claim 12, further comprising at least one antigen or at least one RNA or DNA nucleic acid sequence encoding an antigen.

14. The immune-stimulating composition according to claim 12, further comprising: (i) an accessory immune stimulating molecule, (ii) an immune stimulating molecule, or a combination of (i) and (ii).

15. The method of stimulating an immune response in an individual according to claim 5, wherein said constitutively active pro-inflammatory caspase is provided as an immune-stimulating composition comprising the caspase and a pharmacologically acceptable excipient.

16. The constitutively active pro-inflammatory caspase of claim 1, wherein the swapped p10 and p20 domains are connected by a protease cleavable site.

17. The constitutively active pro-inflammatory caspase of claim 1, which is a human caspase.

18. The method according to claim 5, wherein said caspase is a human caspase.

19. The method according to claim 15, wherein said caspase is a human caspase.

20. The immune-stimulating composition according to claim 12, wherein said caspase is a human caspase.

21. An expression construct encoding the constitutively active pro-inflammatory caspase of claim 1.

22. The expression construct according to claim 21, wherein said caspase is a human caspase.

* * * * *